US009849289B2

(12) United States Patent
Mashiach et al.

(10) Patent No.: US 9,849,289 B2
(45) Date of Patent: *Dec. 26, 2017

(54) DEVICE AND METHOD FOR SNORING DETECTION AND CONTROL

(71) Applicant: Nyxoah SA, Mont-St-Guibert (BE)

(72) Inventors: Adi Mashiach, Tel Aviv (IL); Carsten Mueller, St. Ingbert (DE)

(73) Assignee: NYXOAH SA, Mont-St-Guibert (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/306,916

(22) Filed: Jun. 17, 2014

(65) Prior Publication Data

US 2014/0358189 A1 Dec. 4, 2014

Related U.S. Application Data

(63) Continuation-in-part of application No. 14/041,598, filed on Sep. 30, 2013, now Pat. No. 9,409,013, which
(Continued)

(51) Int. Cl.
*A61N 1/05* (2006.01)
*A61N 1/36* (2006.01)
(Continued)

(52) U.S. Cl.
CPC .......... *A61N 1/3611* (2013.01); *A61B 5/0031* (2013.01); *A61B 5/08* (2013.01);
(Continued)

(58) Field of Classification Search
CPC . A61N 1/3605; A61N 1/3611; A61N 1/37211
(Continued)

(56) References Cited

U.S. PATENT DOCUMENTS 5,540,732 A 7/1996 Testerman
5,540,733 A 7/1996 Testerman et al.
(Continued)

FOREIGN PATENT DOCUMENTS

DE 10003338 A1 11/2000
DE 69526767 T2 1/2003
(Continued)

OTHER PUBLICATIONS

"Definition of Snoring". Merriam-Webster Dictionary. Retrieved Feb. 25, 2015. http://www.merriam-webster.com/medlineplus/snoring.*
(Continued)

*Primary Examiner* — Michael Carey
(74) *Attorney, Agent, or Firm* — Finnegan, Henderson, Farabow, Garrett & Dunner, LLP

(57) ABSTRACT

A device for the treatment of snoring is provided. The device may include a flexible substrate configured for removable attachment to a subject's skin, a primary antenna disposed on the flexible substrate, an interface configured to receive a feedback signal that varies based upon a breathing pattern of the subject; and at least one processing device. The processing device may be configured to analyze the feedback signal and determine whether the subject is snoring based on the analysis of the feedback signal, and if snoring is detected, cause a hypoglossal nerve modulation control signal to be applied to the primary antenna in order to wirelessly transmit the hypoglossal nerve modulation control signal to a secondary antenna associated with an implant unit configured for location in a body of the subject.

10 Claims, 25 Drawing Sheets

Related U.S. Application Data is a continuation-in-part of application No. 13/629,690, filed on Sep. 28, 2012, now Pat. No. 9,403,009, and a continuation-in-part of application No. 13/629,694, filed on Sep. 28, 2012, now Pat. No. 8,577,472, and a continuation-in-part of application No. 13/629,701, filed on Sep. 28, 2012, now Pat. No. 8,588,941, and a continuation-in-part of application No. 13/629,712, filed on Sep. 28, 2012, now Pat. No. 9,314,613, and a continuation-in-part of application No. 13/629,730, filed on Sep. 28, 2012, now Pat. No. 8,577,465, and a continuation-in-part of application No. 13/629,741, filed on Sep. 28, 2012, now Pat. No. 8,577,466, and a continuation-in-part of application No. 13/629,748, filed on Sep. 28, 2012, now Pat. No. 8,700,183, and a continuation-in-part of application No. 13/629,757, filed on Sep. 28, 2012, now Pat. No. 9,302,093, and a continuation-in-part of application No. 13/630,392, filed on Sep. 28, 2012, now Pat. No. 8,644,957, and a continuation-in-part of application No. 13/629,762, filed on Sep. 28, 2012, now Pat. No. 8,577,467, and a continuation-in-part of application No. 13/629,793, filed on Sep. 28, 2012, now Pat. No. 8,577,468, and a continuation-in-part of application No. 13/629,819, filed on Sep. 28, 2012, now Pat. No. 8,718,776, and a continuation-in-part of application No. 13/629,686, filed on Sep. 28, 2012, now Pat. No. 8,577,464, which is a continuation-in-part of application No. 12/642,866, filed on Dec. 21, 2009, now Pat. No. 8,585,617, and a continuation-in-part of application No. 12/581,907, filed on Oct. 20, 2009, said application No. 14/041,598 is a continuation-in-part of application No. 13/629,721, filed on Sep. 28, 2012, now Pat. No. 8,574,164, which is a continuation-in-part of application No. 12/642,866, and a continuation-in-part of application No. 12/581,907, said application No. 14/041,598 is a continuation-in-part of application No. 13/629,725, filed on Sep. 28, 2012, now Pat. No. 8,577,478.

(60) Provisional application No. 61/541,651, filed on Sep. 30, 2011, provisional application No. 61/657,424, filed on Jun. 8, 2012, provisional application No. 61/836,089, filed on Jun. 17, 2013.

(51) Int. Cl.

| | | |
|---|---|---|
| *A61N 1/375* | (2006.01) | |
| *A61N 1/378* | (2006.01) | |
| *A61N 2/00* | (2006.01) | |
| *A61B 5/11* | (2006.01) | |
| *A61B 5/113* | (2006.01) | |
| *A61F 5/56* | (2006.01) | |
| *A61N 1/372* | (2006.01) | |
| *A61B 5/08* | (2006.01) | |
| *A61B 5/00* | (2006.01) | |
| *A61N 2/02* | (2006.01) | |
| *A61B 5/0488* | (2006.01) | |

(52) U.S. Cl.
CPC ............ *A61B 5/11* (2013.01); *A61B 5/113* (2013.01); *A61B 5/4818* (2013.01); *A61B 5/682* (2013.01); *A61F 5/566* (2013.01); *A61N 1/0514* (2013.01); *A61N 1/0526* (2013.01); *A61N 1/0553* (2013.01); *A61N 1/3601* (2013.01); *A61N 1/36003* (2013.01); *A61N 1/3606* (2013.01); *A61N 1/36057* (2013.01); *A61N 1/36135* (2013.01); *A61N 1/36139* (2013.01); *A61N 1/36146* (2013.01); *A61N 1/3756* (2013.01); *A61N 1/3787* (2013.01); *A61N 1/37223* (2013.01); *A61N 1/37229* (2013.01); *A61N 2/006* (2013.01); *A61B 5/0488* (2013.01); *A61B 5/4519* (2013.01); *A61B 5/6822* (2013.01); *A61B 5/6833* (2013.01); *A61B 5/6876* (2013.01); *A61B 2560/0219* (2013.01); *A61B 2562/164* (2013.01); *A61N 1/36075* (2013.01); *A61N 1/36117* (2013.01); *A61N 2/02* (2013.01)

(58) Field of Classification Search
USPC .................. 607/42, 60, 61, 65, 134, 152
See application file for complete search history.

(56) References Cited

U.S. PATENT DOCUMENTS

| | | | |
|---|---|---|---|
| 5,546,952 | A | 8/1996 | Erickson |
| 5,549,655 | A | 8/1996 | Erickson |
| 5,591,216 | A | 1/1997 | Testerman et al. |
| 5,690,693 | A | 11/1997 | Wang et al. |
| 5,702,431 | A | 12/1997 | Wang et al. |
| 5,725,564 | A | 3/1998 | Freed et al. |
| 5,741,316 | A | 4/1998 | Chen et al. |
| 5,871,512 | A | 2/1999 | Hemming et al. |
| 5,873,898 | A | 2/1999 | Hemming et al. |
| 5,891,185 | A | 4/1999 | Freed et al. |
| 5,945,762 | A | 8/1999 | Chen et al. |
| 5,948,006 | A | 9/1999 | Mann |
| 5,987,359 | A | 11/1999 | Freed et al. |
| 6,009,878 | A | 1/2000 | Weijand et al. |
| 6,038,480 | A | 3/2000 | Hrdlicka et al. |
| 6,051,017 | A | 4/2000 | Loeb et al. |
| 6,058,330 | A | 5/2000 | Borza |
| 6,092,531 | A | 7/2000 | Chen et al. |
| 6,104,958 | A | 8/2000 | Freed et al. |
| 6,132,384 | A | 10/2000 | Christopherson et al. |
| 6,134,473 | A | 10/2000 | Hemming et al. |
| 6,144,881 | A | 11/2000 | Hemming et al. |
| 6,163,724 | A | 12/2000 | Hemming et al. |
| 6,175,764 | B1 | 1/2001 | Loeb et al. |
| 6,181,965 | B1 | 1/2001 | Loeb et al. |
| 6,185,455 | B1 | 2/2001 | Loeb et al. |
| 6,198,970 | B1 | 3/2001 | Freed et al. |
| 6,212,431 | B1 | 4/2001 | Hahn et al. |
| 6,214,032 | B1 | 4/2001 | Loeb et al. |
| 6,240,316 | B1 | 5/2001 | Richmond et al. |
| 6,240,318 | B1 | 5/2001 | Phillips |
| 6,251,126 | B1 | 6/2001 | Ottenhoff et al. |
| 6,269,269 | B1 | 7/2001 | Ottenhoff et al. |
| 6,275,737 | B1 | 8/2001 | Mann |
| 6,281,611 | B1 | 8/2001 | Chen et al. |
| 6,305,381 | B1 | 10/2001 | Weijand et al. |
| 6,324,430 | B1 | 11/2001 | Zarinetchi et al. |
| 6,324,431 | B1 | 11/2001 | Zarinetchi et al. |
| 6,331,744 | B1 | 12/2001 | Chen et al. |
| 6,344,021 | B1 | 2/2002 | Juster et al. |
| 6,345,202 | B2 | 2/2002 | Richmond et al. |
| 6,358,281 | B1 | 3/2002 | Berrang et al. |
| 6,389,318 | B1 | 5/2002 | Zarinetchi et al. |
| 6,430,444 | B1 | 8/2002 | Borza |
| 6,473,653 | B1 | 10/2002 | Schallhorn et al. |
| 6,477,425 | B1 | 11/2002 | Nowick et al. |
| 6,496,733 | B1 | 12/2002 | Zarinetchi et al. |
| 6,572,543 | B1 | 6/2003 | Christopherson et al. |
| 6,574,507 | B1 | 6/2003 | Bonnet |
| 6,587,725 | B1 | 7/2003 | Durand et al. |
| 6,622,049 | B2 | 9/2003 | Penner et al. |
| 6,628,989 | B1 | 9/2003 | Penner et al. |
| 6,636,767 | B1 | 10/2003 | Knudson et al. |
| 6,648,914 | B2 | 11/2003 | Berrang et al. |
| 6,657,351 | B2 | 12/2003 | Chen et al. |
| 6,684,105 | B2 | 1/2004 | Cohen et al. |
| 6,704,602 | B2 | 3/2004 | Berg et al. |

(56) References Cited

U.S. PATENT DOCUMENTS

| | | |
|---|---|---|
| 6,735,475 B1 | 5/2004 | Whitehurst et al. |
| 6,736,771 B2 | 5/2004 | Sokolich et al. |
| 6,738,671 B2 | 5/2004 | Christopherson et al. |
| 6,764,446 B2 | 7/2004 | Wolinsky et al. |
| 6,770,022 B2 | 8/2004 | Mechlenburg et al. |
| 6,788,975 B1 | 9/2004 | Whitehurst et al. |
| 6,839,594 B2 | 1/2005 | Cohen et al. |
| 6,845,271 B2 | 1/2005 | Fang et al. |
| 6,850,803 B1 | 2/2005 | Jimenez et al. |
| 6,892,098 B2 | 5/2005 | Ayal et al. |
| 6,907,295 B2 | 6/2005 | Gross et al. |
| 6,928,324 B2 | 8/2005 | Park et al. |
| 6,937,891 B2 | 8/2005 | Leinders et al. |
| 7,024,248 B2 | 4/2006 | Penner et al. |
| 7,027,860 B2 | 4/2006 | Bruninga et al. |
| 7,039,468 B2 | 5/2006 | Freed et al. |
| 7,054,691 B1 | 5/2006 | Kuzma et al. |
| 7,103,408 B2 | 9/2006 | Haller et al. |
| 7,120,992 B2 | 10/2006 | He et al. |
| 7,132,173 B2 | 11/2006 | Daulton |
| 7,146,221 B2 | 12/2006 | Krulevitch et al. |
| 7,149,586 B2 | 12/2006 | Greenberg et al. |
| 7,155,278 B2 | 12/2006 | King et al. |
| 7,167,737 B2 | 1/2007 | Fujii et al. |
| 7,177,698 B2 | 2/2007 | Klosterman et al. |
| 7,181,287 B2 | 2/2007 | Greenberg |
| 7,198,603 B2 | 4/2007 | Penner et al. |
| 7,209,790 B2 | 4/2007 | Thompson et al. |
| 7,212,862 B2 | 5/2007 | Park et al |
| 7,225,032 B2 | 5/2007 | Schmeling et al. |
| 7,257,438 B2 | 8/2007 | Kinast |
| 7,263,403 B2 | 8/2007 | Greenberg et al. |
| 7,273,457 B2 | 9/2007 | Penner |
| 7,277,749 B2 | 10/2007 | Gordon et al. |
| 7,280,873 B2 | 10/2007 | Freed et al. |
| 7,283,874 B2 | 10/2007 | Penner |
| 7,286,881 B2 | 10/2007 | Schommer et al. |
| 7,289,855 B2 | 10/2007 | Nghiem et al. |
| 7,308,316 B2 | 12/2007 | Schommer |
| 7,321,793 B2 | 1/2008 | Ben Ezra et al. |
| 7,324,853 B2 | 1/2008 | Ayal et al. |
| 7,338,522 B2 | 3/2008 | Greenberg et al. |
| 7,346,398 B2 | 3/2008 | Gross et al. |
| 7,351,921 B1 | 4/2008 | Haller et al. |
| 7,367,935 B2 | 5/2008 | Mechlenburg et al. |
| 7,392,091 B2 | 6/2008 | Bruinsma |
| 7,392,092 B2 | 6/2008 | Li et al. |
| 7,409,245 B1 | 8/2008 | Larson et al. |
| 7,428,438 B2 | 9/2008 | Parramon et al. |
| 7,437,193 B2 | 10/2008 | Parramon et al. |
| 7,447,551 B2 | 11/2008 | Kuo et al. |
| 7,482,783 B2 | 1/2009 | Schommer |
| 7,483,750 B2 | 1/2009 | Greenberg et al. |
| 7,489,966 B2 | 2/2009 | Leinders et al. |
| 7,493,172 B2 | 2/2009 | Whitehurst et al. |
| 7,499,754 B2 | 3/2009 | Greenberg et al. |
| 7,502,652 B2 | 3/2009 | Gaunt et al. |
| 7,512,443 B2 | 3/2009 | Phillips et al. |
| 7,527,621 B2 | 5/2009 | Greenberg et al. |
| 7,555,345 B2 | 6/2009 | Wahlstrand et al. |
| 7,561,922 B2 | 7/2009 | Cohen et al. |
| 7,587,241 B2 | 9/2009 | Parramon et al. |
| 7,599,744 B2 | 10/2009 | Giordano et al. |
| 7,610,065 B2 | 10/2009 | Vallapureddy et al. |
| 7,610,103 B2 | 10/2009 | Whitehurst et al. |
| 7,617,001 B2 | 11/2009 | Penner et al. |
| 7,628,750 B2 | 12/2009 | Cohen et al. |
| 7,630,771 B2 | 12/2009 | Cauller |
| 7,631,424 B2 | 12/2009 | Greenberg et al. |
| 7,634,317 B2 | 12/2009 | Ben-David et al. |
| 7,636,602 B2 | 12/2009 | Baru Fassio et al. |
| 7,640,061 B2 | 12/2009 | He et al. |
| 7,641,619 B2 | 1/2010 | Penner |
| 7,647,112 B2 | 1/2010 | Tracey et al. |
| 7,660,632 B2 | 2/2010 | Kirby et al. |
| 7,668,580 B2 | 2/2010 | Shin et al. |
| 7,668,602 B2 | 2/2010 | Ben-David et al. |
| 7,672,728 B2 | 3/2010 | Libbus et al. |
| 7,680,538 B2 | 3/2010 | Durand et al. |
| 7,684,866 B2 | 3/2010 | Fowler et al. |
| 7,711,435 B2 | 5/2010 | Schommer |
| 7,720,547 B2 | 5/2010 | Denker et al. |
| 7,725,195 B2 * | 5/2010 | Lima et al. .................... 607/60 |
| 7,734,355 B2 | 6/2010 | Cohen et al. |
| 7,756,587 B2 | 7/2010 | Penner et al. |
| 7,766,216 B2 | 8/2010 | Daulton |
| 7,769,461 B2 | 8/2010 | Whitehurst et al. |
| 7,774,069 B2 | 8/2010 | Olson et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,781,683 B2 | 8/2010 | Haller et al. |
| 7,797,050 B2 | 9/2010 | Libbus et al. |
| 7,805,203 B2 | 9/2010 | Ben-David et al. |
| 7,809,442 B2 | 10/2010 | Bolea et al. |
| 7,810,233 B2 | 10/2010 | Krulevitch et al. |
| 7,822,480 B2 | 10/2010 | Park et al. |
| 7,831,308 B2 | 11/2010 | Rezai et al. |
| 7,836,888 B2 | 11/2010 | Hegde et al. |
| 7,844,346 B2 | 11/2010 | Cohen et al. |
| 7,845,357 B2 | 12/2010 | Buscemi et al. |
| 7,881,800 B2 | 2/2011 | Daly et al. |
| 7,882,842 B2 | 2/2011 | Bhat et al. |
| 7,885,709 B2 | 2/2011 | Ben-David |
| 7,885,711 B2 | 2/2011 | Ben-Ezra et al. |
| 7,887,493 B2 | 2/2011 | Stahmann et al. |
| 7,890,178 B2 | 2/2011 | Testerman et al. |
| 7,890,185 B2 | 2/2011 | Cohen et al. |
| 7,890,193 B2 | 2/2011 | Tingey |
| 7,894,909 B2 | 2/2011 | Greenberg et al. |
| 7,904,151 B2 | 3/2011 | Ben-David et al. |
| 7,904,163 B2 | 3/2011 | Greenberg et al. |
| 7,904,167 B2 | 3/2011 | Klosterman et al. |
| 7,904,176 B2 | 3/2011 | Ben-Ezra et al. |
| 7,908,008 B2 | 3/2011 | Ben-David et al. |
| 7,909,037 B2 | 3/2011 | Hegde et al. |
| 7,909,038 B2 | 3/2011 | Hegde et al. |
| 7,925,356 B2 | 4/2011 | Li et al. |
| 7,930,031 B2 | 4/2011 | Penner |
| RE42,378 E | 5/2011 | Wolinsky et al. |
| 7,937,159 B2 | 5/2011 | Lima et al. |
| 7,945,334 B2 | 5/2011 | Jimenez et al. |
| 7,970,479 B2 | 6/2011 | Goroszeniuk |
| 7,974,693 B2 | 7/2011 | Ben-David et al. |
| 7,979,126 B2 | 7/2011 | Payne et al. |
| 7,979,128 B2 | 7/2011 | Tehrani et al. |
| 7,979,137 B2 | 7/2011 | Tracey et al. |
| 7,980,248 B2 | 7/2011 | Hegde et al. |
| 7,991,478 B2 | 8/2011 | Greenberg et al. |
| 8,005,542 B2 | 8/2011 | Ben-Ezra et al. |
| 8,005,545 B2 | 8/2011 | Ben-David et al. |
| 8,010,205 B2 | 8/2011 | Rahman et al. |
| 8,014,878 B2 | 9/2011 | Greenberg et al. |
| 8,024,044 B2 | 9/2011 | Kirby et al. |
| 8,024,047 B2 | 9/2011 | Olson et al. |
| 8,027,735 B1 | 9/2011 | Tziviskos et al. |
| 8,032,227 B2 | 10/2011 | Parramon et al. |
| 8,035,255 B2 | 10/2011 | Kurs et al. |
| 8,036,745 B2 | 10/2011 | Ben-David et al. |
| 8,036,752 B2 | 10/2011 | Greenberg et al. |
| 8,060,197 B2 | 11/2011 | Ben-David et al. |
| 8,060,211 B2 | 11/2011 | Greenberg et al. |
| 8,065,021 B2 | 11/2011 | Gross et al. |
| 8,074,655 B2 | 12/2011 | Sanders |
| 8,078,284 B2 | 12/2011 | Greenberg et al. |
| 8,086,318 B2 | 12/2011 | Strother et al. |
| 8,115,618 B2 | 2/2012 | Robertson et al. |
| 8,116,881 B2 | 2/2012 | Cohen et al. |
| 8,122,596 B2 | 2/2012 | Krulevitch et al. |
| 8,126,562 B2 | 2/2012 | Fowler et al. |
| 8,127,424 B2 | 3/2012 | Haller et al. |
| 8,131,375 B2 | 3/2012 | Greenberg et al. |
| 8,140,167 B2 | 3/2012 | Donders et al. |
| 8,160,696 B2 | 4/2012 | Bendett et al. |

(56) References Cited

U.S. PATENT DOCUMENTS

| | | |
|---|---|---|
| 8,165,695 B2 | 4/2012 | DiUbaldi et al. |
| 8,170,680 B2 | 5/2012 | Ameri |
| 8,170,681 B2 | 5/2012 | Jimenez et al. |
| 8,174,460 B2 | 5/2012 | Larson et al. |
| 8,175,714 B2 | 5/2012 | Greenberg et al. |
| 8,175,716 B2 | 5/2012 | Rahman et al. |
| 8,180,460 B2 | 5/2012 | Nevsmith et al. |
| 8,185,212 B2 | 5/2012 | Carbunaru et al. |
| 8,204,591 B2 | 6/2012 | Ben-David et al. |
| 8,214,009 B2 | 7/2012 | Shin et al. |
| 8,214,045 B2 | 7/2012 | Kronich et al. |
| 8,220,467 B2 | 7/2012 | Sanders |
| 8,224,444 B2 | 7/2012 | Ben-David et al. |
| 8,224,449 B2 | 7/2012 | Carbunaru et al. |
| 8,229,567 B2 | 7/2012 | Phillips et al. |
| 8,238,975 B2 | 8/2012 | Vallapureddy et al. |
| 8,241,950 B2 | 8/2012 | Pellinen et al. |
| 8,249,713 B2 | 8/2012 | Fang et al. |
| 8,249,723 B2 | 8/2012 | McCreery |
| 8,256,425 B2 | 9/2012 | Bagley et al. |
| 8,260,432 B2 | 9/2012 | DiGiore et al. |
| 8,260,439 B2 | 9/2012 | Diubaldi et al. |
| 8,265,763 B2 | 9/2012 | Fahey |
| 8,265,770 B2 | 9/2012 | Toy et al. |
| 8,285,381 B2 | 10/2012 | Fahey |
| 8,295,936 B2 | 10/2012 | Wahlstrand et al. |
| 8,301,261 B2 | 10/2012 | Bruinsma |
| 8,311,645 B2 | 11/2012 | Bolea et al. |
| 8,336,553 B2 | 12/2012 | Bhat et al. |
| 8,352,026 B2 | 1/2013 | DiUbaldi |
| 8,359,108 B2 | 1/2013 | McCreery |
| 8,369,957 B2 | 2/2013 | Greenberg et al. |
| 8,381,735 B2 | 2/2013 | Buscemi et al. |
| 8,386,046 B2 | 2/2013 | Tesfayesus et al. |
| 8,386,048 B2 | 2/2013 | McClure et al. |
| 8,386,056 B2 | 2/2013 | Ben David et al. |
| 8,391,991 B2 | 3/2013 | Rahman et al. |
| 8,406,886 B2 | 3/2013 | Gaunt et al. |
| 8,408,213 B2 | 4/2013 | Sanders |
| 8,417,343 B2 | 4/2013 | Bolea et al. |
| 8,428,725 B2 | 4/2013 | Meadows et al. |
| 8,428,727 B2 | 4/2013 | Bolea et al. |
| 8,428,746 B2 | 4/2013 | DiGiore et al. |
| 8,433,403 B2 | 4/2013 | Fahey |
| 8,447,410 B2 | 5/2013 | Greenberg et al. |
| 8,457,758 B2 | 6/2013 | Olson et al. |
| 8,463,383 B2 | 6/2013 | Sakai et al. |
| 8,463,394 B2 | 6/2013 | Forsell |
| 8,463,395 B2 | 6/2013 | Forsell |
| 8,473,025 B2 | 6/2013 | Shin et al. |
| 8,489,200 B2 | 7/2013 | Zarinetchi et al. |
| 8,494,641 B2 | 7/2013 | Boling et al. |
| 8,494,655 B2 | 7/2013 | Ayal et al. |
| 8,498,712 B2 | 7/2013 | Bolea et al. |
| 8,498,716 B2 | 7/2013 | Chen et al. |
| 8,509,909 B2 | 8/2013 | Figueiredo et al. |
| 8,509,911 B2 | 8/2013 | Li et al. |
| 8,510,939 B2 | 8/2013 | Greenberg et al. |
| 8,515,544 B2 | 8/2013 | Daly et al. |
| 8,532,787 B2 | 9/2013 | Lambert et al. |
| 8,538,503 B2 | 9/2013 | Kumar et al. |
| 8,540,631 B2 | 9/2013 | Penner et al. |
| 8,540,632 B2 | 9/2013 | Robertson et al. |
| 8,543,216 B2 | 9/2013 | Carbunaru et al. |
| 8,560,046 B2 | 10/2013 | Kumar et al. |
| 8,565,896 B2 | 10/2013 | Ben-David et al. |
| 8,571,651 B2 | 10/2013 | Ben-Ezra et al. |
| 8,571,653 B2 | 10/2013 | Ben-David et al. |
| 8,571,679 B2 | 10/2013 | Parramon et al. |
| 8,577,460 B2 | 11/2013 | Penner |
| 8,577,478 B2 * | 11/2013 | Mashiach ............ A61N 1/0551 607/134 |
| 8,578,937 B2 | 11/2013 | Bhat et al. |
| 8,583,256 B2 | 11/2013 | Tracey et al. |
| 8,588,901 B2 | 11/2013 | Fahey |
| 8,588,924 B2 | 11/2013 | Dion |
| 8,588,930 B2 | 11/2013 | DiUbaldi et al. |
| 8,600,517 B2 | 12/2013 | Forsell |
| 8,612,013 B2 | 12/2013 | Forsell |
| 8,612,014 B2 | 12/2013 | Rahman et al. |
| 8,615,294 B2 | 12/2013 | Ben-David et al. |
| 8,620,437 B2 | 12/2013 | Wahlstrand et al. |
| 8,620,447 B2 | 12/2013 | D'Ambrosio et al. |
| 8,626,302 B2 | 1/2014 | Bennett et al. |
| 8,626,304 B2 | 1/2014 | Bolea et al. |
| 8,639,344 B2 | 1/2014 | Greenberg et al. |
| 8,639,354 B2 | 1/2014 | Bolea et al. |
| 8,644,939 B2 | 2/2014 | Wilson et al. |
| 8,655,451 B2 | 2/2014 | Klosterman et al. |
| 8,657,756 B2 | 2/2014 | Stahmann et al. |
| 8,658,465 B2 | 2/2014 | Pellinen et al. |
| 8,668,643 B2 | 3/2014 | Kinast |
| 8,670,835 B2 | 3/2014 | Park et al. |
| 8,676,332 B2 | 3/2014 | Fahey |
| 8,700,177 B2 | 4/2014 | Strother et al. |
| 8,703,537 B2 | 4/2014 | Pellinen et al. |
| 8,718,758 B2 | 5/2014 | Wagner et al. |
| 8,718,783 B2 | 5/2014 | Bolea et al. |
| 8,718,791 B2 | 5/2014 | Ben-David et al. |
| 8,725,271 B2 | 5/2014 | Ayal et al. |
| 8,738,148 B2 | 5/2014 | Olson et al. |
| 8,744,582 B2 | 6/2014 | Wahlstrand et al. |
| 8,744,589 B2 | 6/2014 | Bolea et al. |
| 8,751,003 B2 | 6/2014 | DiUbaldi et al. |
| 8,751,005 B2 | 6/2014 | Meadows et al. |
| 8,774,943 B2 | 7/2014 | McCreery |
| 8,788,046 B2 | 7/2014 | Bennett et al. |
| 8,788,047 B2 | 7/2014 | Bennett et al. |
| 8,788,048 B2 | 7/2014 | Bennett et al. |
| 8,798,763 B2 | 8/2014 | Forsell |
| 8,813,753 B2 | 8/2014 | Bhat et al. |
| 8,825,173 B2 | 9/2014 | Forsell |
| 8,855,771 B2 | 10/2014 | Tesfayesus et al. |
| 8,862,232 B2 | 10/2014 | Zarinetchi et al. |
| 8,880,184 B2 | 11/2014 | Phillips et al. |
| 8,886,304 B2 | 11/2014 | Wagner et al. |
| 8,886,322 B2 | 11/2014 | Meadows et al. |
| 8,886,325 B2 | 11/2014 | Boling et al. |
| 8,886,329 B2 | 11/2014 | Greenberg et al. |
| 8,886,337 B2 | 11/2014 | Bennett et al. |
| 8,892,200 B2 | 11/2014 | Wagner et al. |
| 8,892,205 B2 | 11/2014 | Miller, III et al. |
| 8,892,210 B2 | 11/2014 | Fahey |
| 8,897,871 B2 | 11/2014 | Wagner et al. |
| 8,903,495 B2 | 12/2014 | Greenberg et al. |
| 8,903,502 B2 | 12/2014 | Perryman et al. |
| 8,914,129 B2 | 12/2014 | Parramon et al. |
| 8,925,551 B2 | 1/2015 | Sanders |
| 8,929,979 B2 | 1/2015 | Wagner et al. |
| 8,929,986 B2 | 1/2015 | Parker et al. |
| 8,934,972 B2 | 1/2015 | Penner |
| 8,954,153 B2 | 2/2015 | Boggs, II |
| 8,965,523 B2 | 2/2015 | Forsell |
| 8,965,525 B2 | 2/2015 | Forsell |
| 8,965,535 B2 | 2/2015 | Dunlay et al. |
| 8,972,021 B2 | 3/2015 | Edgell et al. |
| 8,977,354 B2 | 3/2015 | Wagner et al. |
| 8,983,611 B2 | 3/2015 | Mokelke et al. |
| 9,002,451 B2 | 4/2015 | Staunton et al. |
| 9,026,222 B2 | 5/2015 | Forsell |
| 9,031,654 B2 | 5/2015 | Meadows et al. |
| 9,042,991 B2 | 5/2015 | Reed et al. |
| 9,061,134 B2 | 6/2015 | Askin, III et al. |
| 9,061,162 B2 * | 6/2015 | Mashiach ............ A61N 1/3756 |
| 9,072,886 B2 | 7/2015 | Gaunt et al. |
| 9,079,041 B2 | 7/2015 | Park et al. |
| 9,079,043 B2 | 7/2015 | Stark et al. |
| 9,089,690 B2 | 7/2015 | Greenberg et al. |
| 9,113,838 B2 | 8/2015 | Tesfayesus et al. |
| 9,125,290 B2 | 9/2015 | Greenberg et al. |
| 9,126,039 B2 | 9/2015 | Fahey |
| 9,149,228 B2 | 10/2015 | Kinast |
| 9,149,386 B2 | 10/2015 | Fahey et al. |
| 9,149,628 B2 | 10/2015 | Wahlstrand et al. |

(56) References Cited

U.S. PATENT DOCUMENTS

| | | |
|---|---|---|
| 9,162,071 B2 | 10/2015 | Parramon et al. |
| 9,186,496 B2 | 11/2015 | Greenberg et al. |
| 9,186,511 B2 | 11/2015 | Bolea |
| 9,205,258 B2 | 12/2015 | Simon et al. |
| 9,205,262 B2 | 12/2015 | Bolea et al. |
| 9,227,076 B2 | 1/2016 | Sharma et al. |
| 9,233,258 B2 | 1/2016 | Simon et al. |
| 9,241,649 B2 | 1/2016 | Kumar et al. |
| 9,242,106 B2 | 1/2016 | Klosterman et al. |
| 9,248,289 B2 | 2/2016 | Bennett et al. |
| 9,272,081 B2 | 3/2016 | Cameron et al. |
| 9,289,142 B2 | 3/2016 | Kong et al. |
| 9,302,104 B2 | 4/2016 | Fahey |
| 9,308,370 B2 | 4/2016 | Lima et al. |
| 9,314,615 B2 | 4/2016 | Neysmith et al. |
| 9,314,618 B2 | 4/2016 | Imran et al. |
| 9,314,641 B2 | 4/2016 | Meadows et al. |
| 9,320,895 B2 | 4/2016 | Wagner et al. |
| 9,320,908 B2 | 4/2016 | Fletcher et al. |
| 9,339,647 B2 | 5/2016 | Strother et al. |
| 9,339,651 B2 | 5/2016 | Meadows et al. |
| 2002/0010495 A1 | 1/2002 | Freed et al. |
| 2002/0038138 A1 | 3/2002 | Zarinetchi et al. |
| 2002/0055763 A1 | 5/2002 | Zarinetchi et al. |
| 2002/0058971 A1 | 5/2002 | Zarinetchi et al. |
| 2002/0077572 A1 | 6/2002 | Fang et al. |
| 2002/0177884 A1 | 11/2002 | Ahn et al. |
| 2002/0188333 A1 | 12/2002 | Nowick et al. |
| 2003/0030342 A1 | 2/2003 | Chen et al. |
| 2003/0093128 A1 | 5/2003 | Freed et al. |
| 2003/0097165 A1 | 5/2003 | Krulevitch et al. |
| 2004/0064166 A1 | 4/2004 | Thompson et al. |
| 2004/0073272 A1 | 4/2004 | Knudson et al. |
| 2004/0098068 A1 | 5/2004 | Carbunaru et al. |
| 2004/0172104 A1 | 9/2004 | Berg et al. |
| 2004/0236387 A1 | 11/2004 | Fang et al. |
| 2005/0065553 A1 | 3/2005 | Ben Ezra et al. |
| 2005/0085874 A1 | 4/2005 | Davis et al. |
| 2005/0102006 A1 | 5/2005 | Whitehurst et al. |
| 2005/0177067 A1 | 8/2005 | Tracey et al. |
| 2005/0267547 A1 | 12/2005 | Knudson et al. |
| 2005/0283202 A1 | 12/2005 | Gellman |
| 2005/0288743 A1 | 12/2005 | Ahn et al. |
| 2006/0009816 A1 | 1/2006 | Fang et al. |
| 2006/0064140 A1 | 3/2006 | Whitehurst et al. |
| 2006/0090762 A1 | 5/2006 | Hegde et al. |
| 2006/0116739 A1 | 6/2006 | Betser et al. |
| 2006/0190056 A1 | 8/2006 | Fowler et al. |
| 2006/0270968 A1 | 11/2006 | Greenberg et al. |
| 2007/0055324 A1 | 3/2007 | Thompson et al. |
| 2007/0144535 A1 | 6/2007 | Hegde et al. |
| 2007/0233204 A1 | 10/2007 | Lima et al. |
| 2007/0261701 A1 | 11/2007 | Sanders |
| 2008/0046016 A1 | 2/2008 | Ben-David et al. |
| 2008/0047566 A1 | 2/2008 | Hegde et al. |
| 2008/0057179 A1 | 3/2008 | Greenberg et al. |
| 2008/0058898 A1 | 3/2008 | Greenberg et al. |
| 2008/0064946 A1 | 3/2008 | Greenberg et al. |
| 2008/0078411 A1 | 4/2008 | Buscemi et al. |
| 2008/0078412 A1 | 4/2008 | Buscemi et al. |
| 2008/0091241 A1 | 4/2008 | Ben-Ezra et al. |
| 2008/0091245 A1 | 4/2008 | Ben-Ezra et al. |
| 2008/0103407 A1* | 5/2008 | Bolea et al. .................. 600/529 |
| 2008/0109045 A1 | 5/2008 | Gross et al. |
| 2008/0119898 A1 | 5/2008 | Ben-David et al. |
| 2008/0125819 A1 | 5/2008 | Ben-David et al. |
| 2008/0125827 A1 | 5/2008 | Ben-David et al. |
| 2008/0132964 A1 | 6/2008 | Cohen et al. |
| 2008/0147137 A1 | 6/2008 | Cohen et al. |
| 2008/0177351 A1 | 7/2008 | Fang et al. |
| 2008/0300657 A1 | 12/2008 | Stultz |
| 2009/0005845 A1 | 1/2009 | David et al. |
| 2009/0038623 A1 | 2/2009 | Farbarik et al. |
| 2009/0069866 A1 | 3/2009 | Farbarik et al. |
| 2009/0078275 A1 | 3/2009 | Hegde et al. |
| 2009/0173351 A1 | 7/2009 | Sahin et al. |
| 2009/0240314 A1 | 9/2009 | Kong et al. |
| 2010/0010603 A1 | 1/2010 | Ben-David et al. |
| 2010/0016929 A1 | 1/2010 | Prochazka |
| 2010/0063568 A1 | 3/2010 | Staunton et al. |
| 2010/0069994 A1 | 3/2010 | Cauller |
| 2010/0087896 A1* | 4/2010 | McCreery .................. 607/62 |
| 2010/0131029 A1 | 5/2010 | Durand et al. |
| 2010/0152809 A1 | 6/2010 | Boggs, II |
| 2010/0174341 A1 | 7/2010 | Bolea et al. |
| 2010/0198103 A1 | 8/2010 | Meadows et al. |
| 2010/0217353 A1 | 8/2010 | Forsell |
| 2010/0241195 A1 | 9/2010 | Meadows et al. |
| 2010/0319711 A1 | 12/2010 | Hegde et al. |
| 2011/0009920 A1 | 1/2011 | Whitehurst et al. |
| 2011/0071591 A1 | 3/2011 | Bolea et al. |
| 2011/0112601 A1 | 5/2011 | Meadows et al. |
| 2011/0152706 A1 | 6/2011 | Christopherson et al. |
| 2011/0160794 A1 | 6/2011 | Bolea et al. |
| 2011/0172733 A1 | 7/2011 | Lima et al. |
| 2011/0202119 A1 | 8/2011 | Ni et al. |
| 2011/0213438 A1 | 9/2011 | Lima et al. |
| 2011/0240037 A1 | 10/2011 | Hegde et al. |
| 2011/0245734 A1 | 10/2011 | Wagner et al. |
| 2011/0265322 A1 | 11/2011 | Greenberg et al. |
| 2011/0275927 A1 | 11/2011 | Wagner et al. |
| 2012/0022609 A1 | 1/2012 | Bolea et al. |
| 2012/0065701 A1 | 3/2012 | Cauller |
| 2012/0109020 A1 | 5/2012 | Wagner et al. |
| 2012/0192874 A1 | 8/2012 | Bolea et al. |
| 2012/0227748 A1 | 9/2012 | Sanders |
| 2012/0286582 A1 | 11/2012 | Kim et al. |
| 2012/0290055 A1 | 11/2012 | Boggs, II |
| 2012/0303080 A1 | 11/2012 | Ben-David et al. |
| 2013/0002423 A1 | 1/2013 | Robertson et al. |
| 2013/0110195 A1 | 5/2013 | Fletcher et al. |
| 2013/0116745 A1 | 5/2013 | Fletcher et al. |
| 2013/0165996 A1 | 6/2013 | Meadows et al. |
| 2013/0197615 A1 | 8/2013 | Rundle et al. |
| 2013/0213404 A1 | 8/2013 | Leibitzki et al. |
| 2013/0218251 A1 | 8/2013 | Penner |
| 2013/0238044 A1 | 9/2013 | Penner |
| 2013/0238066 A1 | 9/2013 | Boggs, II et al. |
| 2013/0274842 A1 | 10/2013 | Gaunt et al. |
| 2013/0338452 A1 | 12/2013 | Robertson et al. |
| 2014/0012342 A1 | 1/2014 | Penner et al. |
| 2014/0046407 A1 | 2/2014 | Ben-Ezra et al. |
| 2014/0058495 A1 | 2/2014 | Sakai et al. |
| 2014/0121741 A1 | 5/2014 | Bennett et al. |
| 2014/0152246 A1 | 6/2014 | Forsell |
| 2014/0155959 A1 | 6/2014 | Forsell |
| 2014/0163661 A1 | 6/2014 | Ben-David et al. |
| 2014/0207220 A1 | 7/2014 | Boling et al. |
| 2014/0214135 A1 | 7/2014 | Ben-David et al. |
| 2014/0249361 A1 | 9/2014 | DiUbaldi et al. |
| 2014/0323839 A1 | 10/2014 | McCreery |
| 2014/0330340 A1 | 11/2014 | Bennett et al. |
| 2014/0330356 A1 | 11/2014 | Bennett et al. |
| 2014/0378740 A1 | 12/2014 | Wagner et al. |
| 2015/0025613 A1 | 1/2015 | Nyberg, II et al. |
| 2015/0039055 A1 | 2/2015 | Wagner et al. |
| 2015/0039067 A1 | 2/2015 | Greenberg et al. |
| 2015/0051678 A1 | 2/2015 | Reed et al. |
| 2015/0066106 A1 | 3/2015 | Greenberg et al. |
| 2015/0105702 A1 | 4/2015 | Wagner et al. |
| 2015/0105840 A1 | 4/2015 | Boggs, II |
| 2015/0119629 A1 | 4/2015 | Wagner et al. |
| 2015/0134037 A1 | 5/2015 | Bennett et al. |
| 2015/0142075 A1 | 5/2015 | Miller, III et al. |
| 2015/0142120 A1 | 5/2015 | Papay |
| 2015/0148713 A1 | 5/2015 | Wagner et al. |
| 2015/0151123 A1 | 6/2015 | Wagner et al. |
| 2015/0174409 A1 | 6/2015 | Parker et al. |
| 2015/0264816 A1 | 9/2015 | Askin, III et al. |
| 2015/0321004 A1 | 11/2015 | Reed et al. |
| 2015/0321008 A1 | 11/2015 | Tesfayesus et al. |
| 2015/0321018 A1 | 11/2015 | Fletcher et al. |
| 2015/0328455 A1 | 11/2015 | Meadows et al. |
| 2015/0374985 A1 | 12/2015 | Fahey |

(56) References Cited

U.S. PATENT DOCUMENTS

| | | |
|---|---|---|
| 2015/0374998 A1 | 12/2015 | Fletcher et al. |
| 2016/0001079 A1 | 1/2016 | Fletcher et al. |
| 2016/0008608 A1 | 1/2016 | Boling et al. |
| 2016/0022481 A1 | 1/2016 | Fahey et al. |
| 2016/0030746 A1 | 2/2016 | Reed et al. |
| 2016/0059011 A1 | 3/2016 | Bolea et al. |
| 2016/0067396 A1 | 3/2016 | Stark et al. |
| 2016/0089540 A1 | 3/2016 | Bolea |
| 2016/0114174 A1 | 4/2016 | Colvin et al. |
| 2016/0114175 A1 | 4/2016 | Colvin et al. |
| 2016/0114177 A1 | 4/2016 | Colvin et al. |
| 2016/0135746 A1 | 5/2016 | Kumar et al. |
| 2016/0144180 A1 | 5/2016 | Simon et al. |

FOREIGN PATENT DOCUMENTS

| | | |
|---|---|---|
| DE | 69529951 T2 | 2/2004 |
| DE | 69722782 T2 | 2/2004 |
| DE | 69629238 T2 | 5/2004 |
| DE | 69532514 T2 | 10/2004 |
| DE | 69730842 T2 | 9/2005 |
| DE | 69927438 T2 | 6/2006 |
| DE | 69928748 T2 | 6/2006 |
| DE | 69636883 T2 | 10/2007 |
| DE | 60315327 T2 | 1/2008 |
| DE | 69535686 T2 | 1/2009 |
| DE | 112008001669 T5 | 5/2010 |
| DE | 202007019439 U1 | 9/2012 |
| EP | 0702977 B1 | 3/1996 |
| EP | 0706808 B1 | 4/1996 |
| EP | 0743076 B1 | 11/1996 |
| EP | 0814868 B1 | 1/1998 |
| EP | 0970713 B1 | 1/2000 |
| EP | 0998328 B1 | 5/2000 |
| EP | 1052935 B1 | 11/2000 |
| EP | 1175919 B1 | 1/2002 |
| EP | 1277491 B1 | 1/2003 |
| EP | 1306104 B1 | 5/2003 |
| EP | 1331969 B1 | 8/2003 |
| EP | 1389079 B1 | 2/2004 |
| EP | 1429837 B1 | 6/2004 |
| EP | 1446188 B1 | 8/2004 |
| EP | 1494753 B1 | 1/2005 |
| EP | 1507473 B1 | 2/2005 |
| EP | 1524007 A1 | 4/2005 |
| EP | 1545693 B1 | 6/2005 |
| EP | 1554012 B1 | 7/2005 |
| EP | 1608432 B1 | 12/2005 |
| EP | 1609502 A1 | 12/2005 |
| EP | 1613396 B1 | 1/2006 |
| EP | 1648559 B1 | 4/2006 |
| EP | 1675648 B1 | 7/2006 |
| EP | 1676526 B1 | 7/2006 |
| EP | 1682222 B1 | 7/2006 |
| EP | 1706178 B1 | 10/2006 |
| EP | 1750801 B1 | 2/2007 |
| EP | 1776922 A1 | 4/2007 |
| EP | 1861162 B1 | 12/2007 |
| EP | 1874397 A2 | 1/2008 |
| EP | 1897586 B1 | 3/2008 |
| EP | 1904153 B1 | 4/2008 |
| EP | 1907048 A2 | 4/2008 |
| EP | 1981583 B1 | 10/2008 |
| EP | 1981589 B1 | 10/2008 |
| EP | 2036588 B1 | 3/2009 |
| EP | 2040790 B1 | 4/2009 |
| EP | 2089100 B1 | 8/2009 |
| EP | 2116274 B1 | 11/2009 |
| EP | 2143465 B1 | 1/2010 |
| EP | 2167187 A2 | 3/2010 |
| EP | 2228095 A3 | 9/2010 |
| EP | 2243509 A1 | 10/2010 |
| EP | 2266164 B1 | 12/2010 |
| EP | 2272562 A1 | 1/2011 |
| EP | 2286871 B1 | 2/2011 |
| EP | 2289596 B1 | 3/2011 |
| EP | 2298408 A2 | 3/2011 |
| EP | 2310088 B1 | 4/2011 |
| EP | 2318088 B1 | 5/2011 |
| EP | 2380625 A1 | 10/2011 |
| EP | 2383015 A1 | 11/2011 |
| EP | 2462982 A1 | 6/2012 |
| EP | 2468358 B1 | 6/2012 |
| EP | 2476458 B1 | 7/2012 |
| EP | 2478931 B1 | 7/2012 |
| EP | 2550992 B1 | 1/2013 |
| EP | 2462983 A1 | 6/2013 |
| EP | 2617396 A2 | 7/2013 |
| EP | 2617457 A2 | 7/2013 |
| EP | 2617460 A2 | 7/2013 |
| EP | 2667933 B1 | 12/2013 |
| EP | 2905051 A1 | 8/2015 |
| EP | 2907542 A1 | 8/2015 |
| EP | 2932998 A1 | 10/2015 |
| EP | 2965782 A1 | 1/2016 |
| EP | 3002035 A1 | 4/2016 |
| EP | 2211977 A1 | 6/2016 |
| WO | WO 96/40367 | 12/1996 |
| WO | WO 97/37720 | 10/1997 |
| WO | WO 97/49454 | 12/1997 |
| WO | WO 98/11942 | 3/1998 |
| WO | WO 98/24510 | 6/1998 |
| WO | WO 99/39769 | 8/1999 |
| WO | WO 99/62594 | 12/1999 |
| WO | WO 00/02212 | 1/2000 |
| WO | WO 00/24456 | 5/2000 |
| WO | WO 01/39830 | 6/2001 |
| WO | WO 01/78216 | 10/2001 |
| WO | WO 03/009749 | 2/2003 |
| WO | WO 03/061335 | 7/2003 |
| WO | WO 03/066153 | 8/2003 |
| WO | WO 03/099377 | 12/2003 |
| WO | WO 2004/002572 | 1/2004 |
| WO | WO 2004/008954 | 1/2004 |
| WO | WO 2004/028624 | 4/2004 |
| WO | WO 2004/064729 | 8/2004 |
| WO | WO 2004/103455 | 12/2004 |
| WO | WO 2004/110549 | 12/2004 |
| WO | WO 2004/110550 | 12/2004 |
| WO | WO 2005/011805 | 2/2005 |
| WO | WO 2005/037370 | 4/2005 |
| WO | WO 2005/077276 | 8/2005 |
| WO | WO 2005/082452 | 9/2005 |
| WO | WO 2006/093964 | 9/2006 |
| WO | WO 2006/132810 | 12/2006 |
| WO | WO 2007/035361 | 3/2007 |
| WO | WO 2007/035774 | 3/2007 |
| WO | WO 2007/081714 | 7/2007 |
| WO | WO 2007/090047 | 8/2007 |
| WO | WO 2007/092865 | 8/2007 |
| WO | WO 2007/098202 | 8/2007 |
| WO | WO 2007/120305 | 10/2007 |
| WO | WO 2007/149571 | 12/2007 |
| WO | WO 2008/005903 | 1/2008 |
| WO | WO 2008/014028 | 1/2008 |
| WO | WO 2008/016802 | 2/2008 |
| WO | WO 2008/039921 | 4/2008 |
| WO | WO 2008/042058 | 4/2008 |
| WO | WO 2008/048724 | 4/2008 |
| WO | WO 2008/079700 | 7/2008 |
| WO | WO 2008/076646 | 8/2008 |
| WO | WO 2009/032625 | 3/2009 |
| WO | WO 2009/046044 | 4/2009 |
| WO | WO 2009/048580 | 4/2009 |
| WO | WO 2009/051536 | 4/2009 |
| WO | WO 2009/051538 | 4/2009 |
| WO | WO 2009/051539 | 4/2009 |
| WO | WO 2009/061537 | 5/2009 |
| WO | WO 2009/070086 | 6/2009 |
| WO | WO 2009/111012 | 9/2009 |
| WO | WO 2009/126354 | 10/2009 |
| WO | WO 2009/140636 | 11/2009 |
| WO | WO 2010/003106 | 1/2010 |
| WO | WO 2010/039853 | 4/2010 |

(56) References Cited

FOREIGN PATENT DOCUMENTS

| WO | WO 2010/042020 | 4/2010 |
| WO | WO 2010/042404 | 4/2010 |
| WO | WO 2010/096776 | 8/2010 |
| WO | WO 2011/060056 | 5/2011 |
| WO | WO 2011/139779 | 11/2011 |
| WO | WO 2011/143490 | 11/2011 |
| WO | WO 2012/030522 | 3/2012 |
| WO | WO 2012/055389 | 5/2012 |
| WO | WO 2013/067538 | 5/2013 |
| WO | WO 2013/078092 | 5/2013 |
| WO | WO 2013/086212 | 6/2013 |
| WO | WO 2013/147799 | 10/2013 |
| WO | WO 2013/173214 | 11/2013 |
| WO | WO 2013/188400 | 12/2013 |
| WO | WO 2014/004526 | 1/2014 |
| WO | WO 2014/179685 | 11/2014 |

OTHER PUBLICATIONS

International Search Report for PCT/IB2014/002291, dated Feb. 11, 2015, 3 pages.

\* cited by examiner

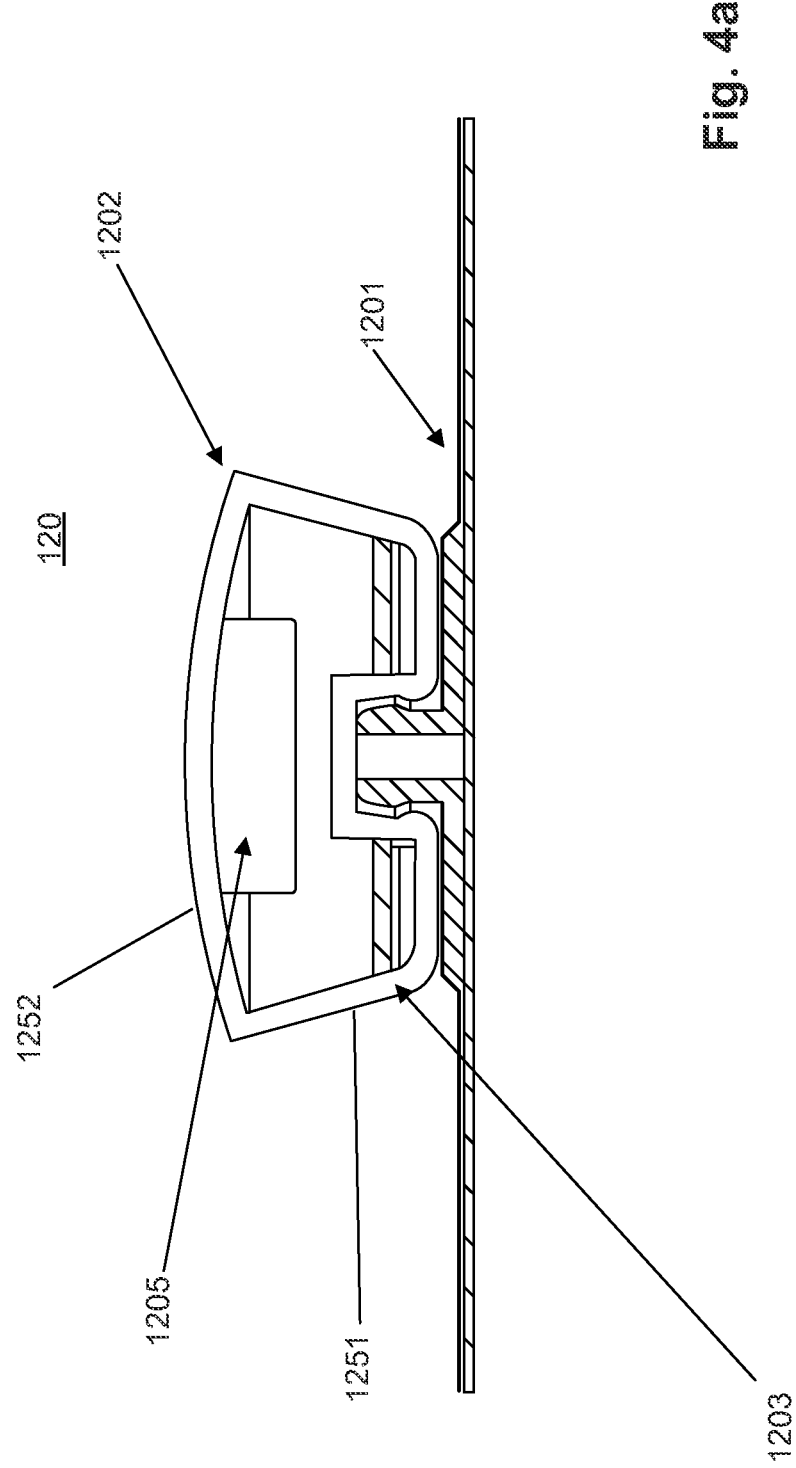

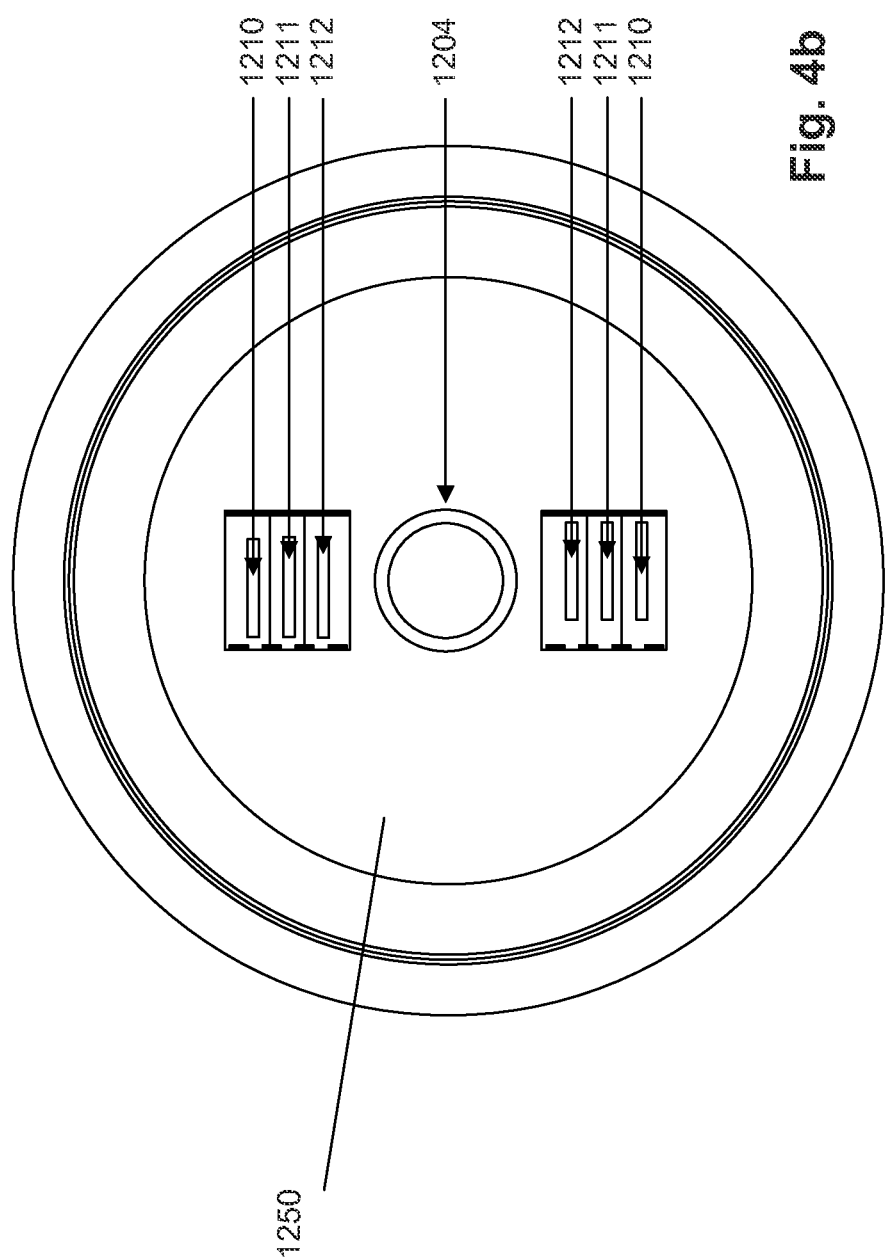

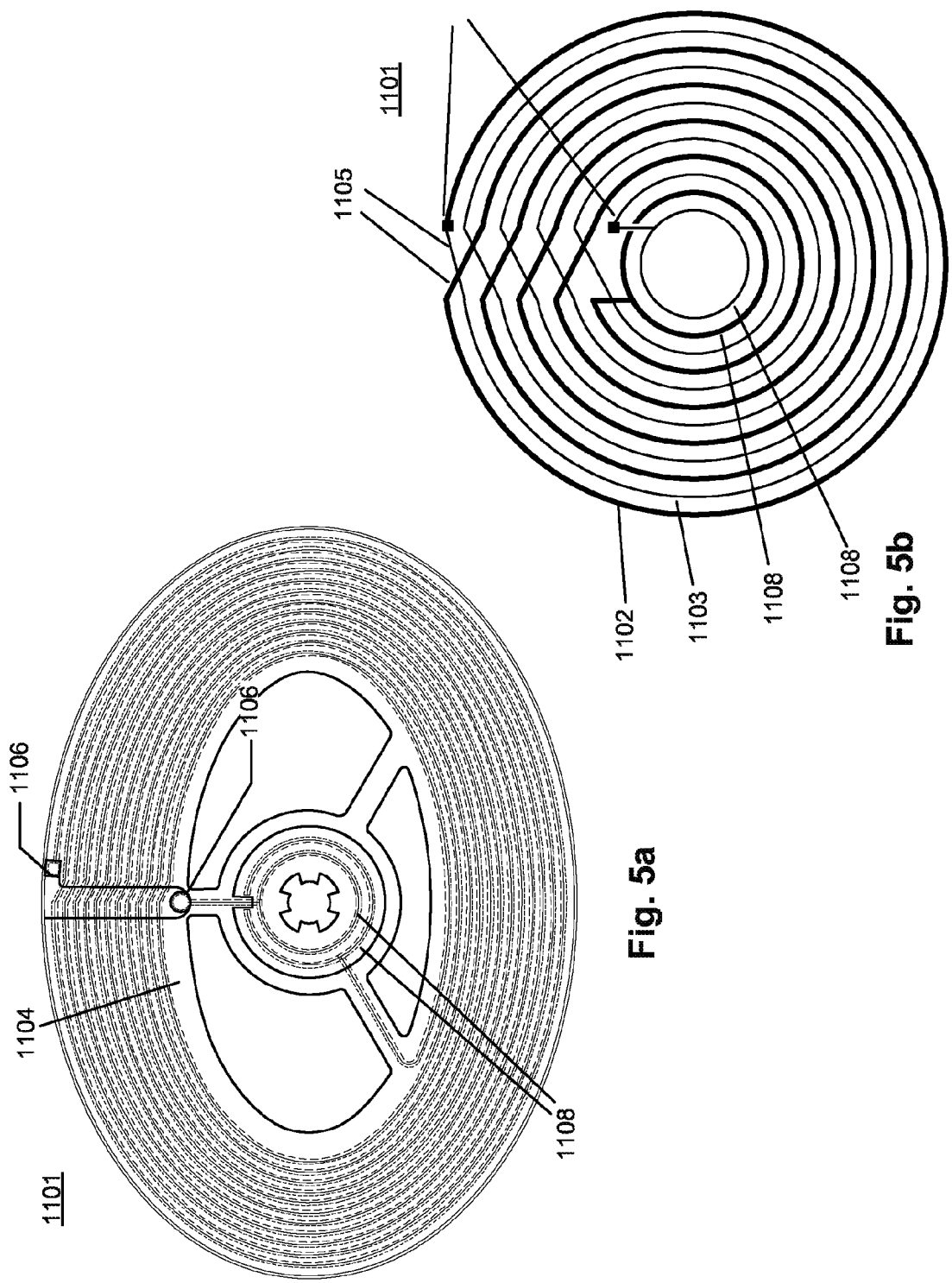

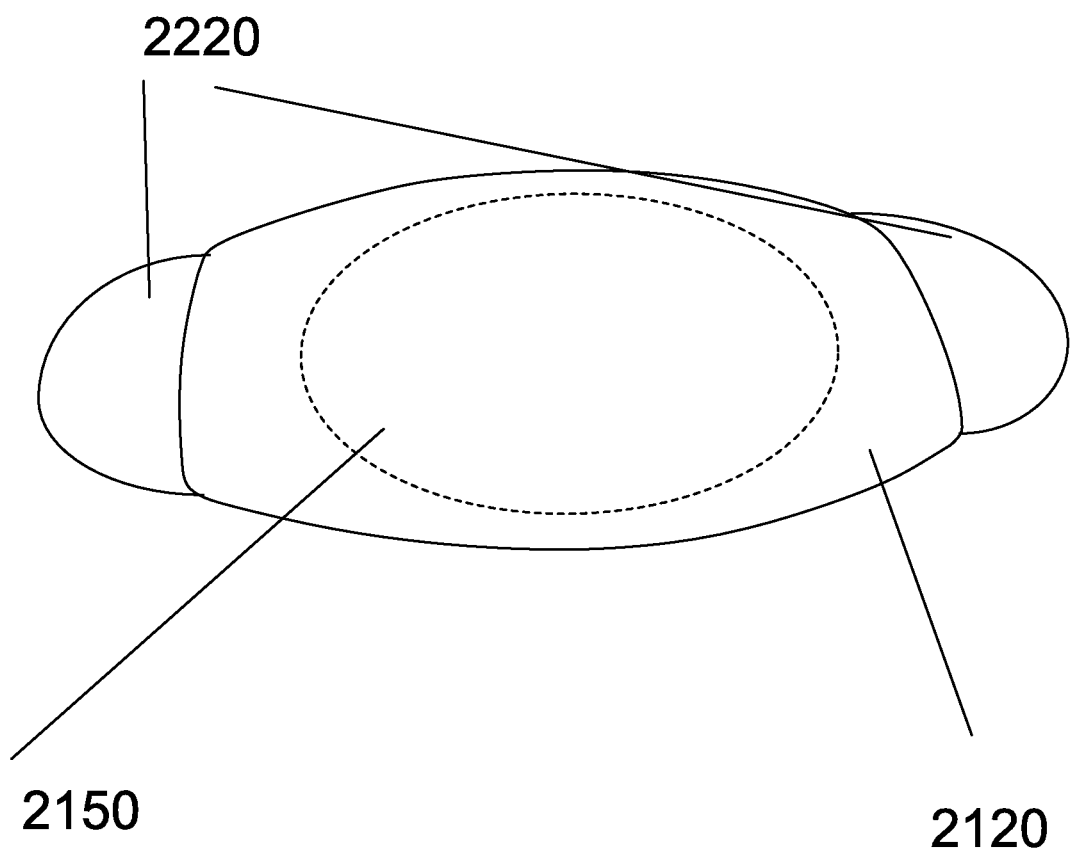
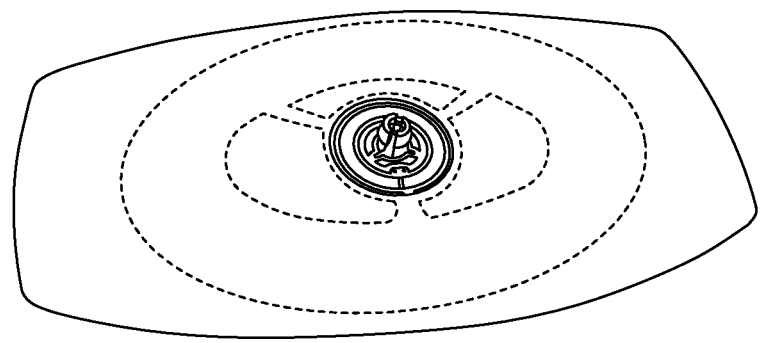
Fig. 7

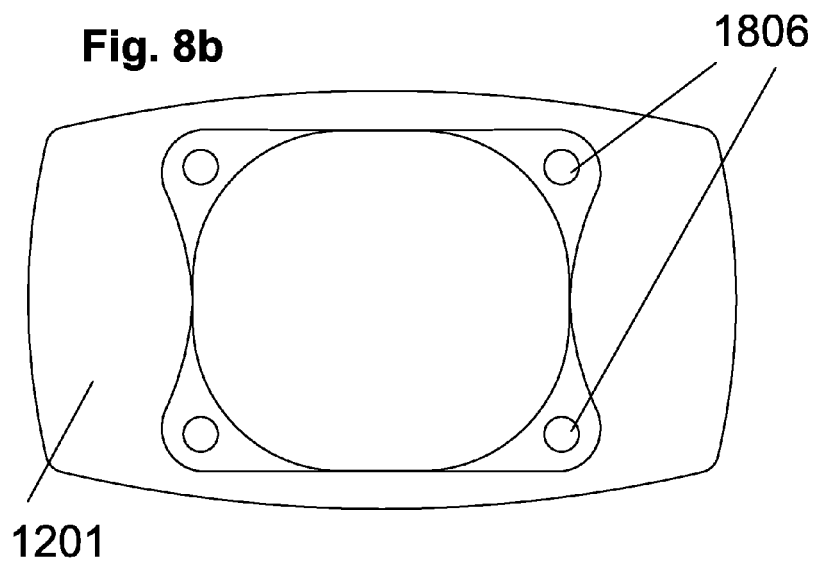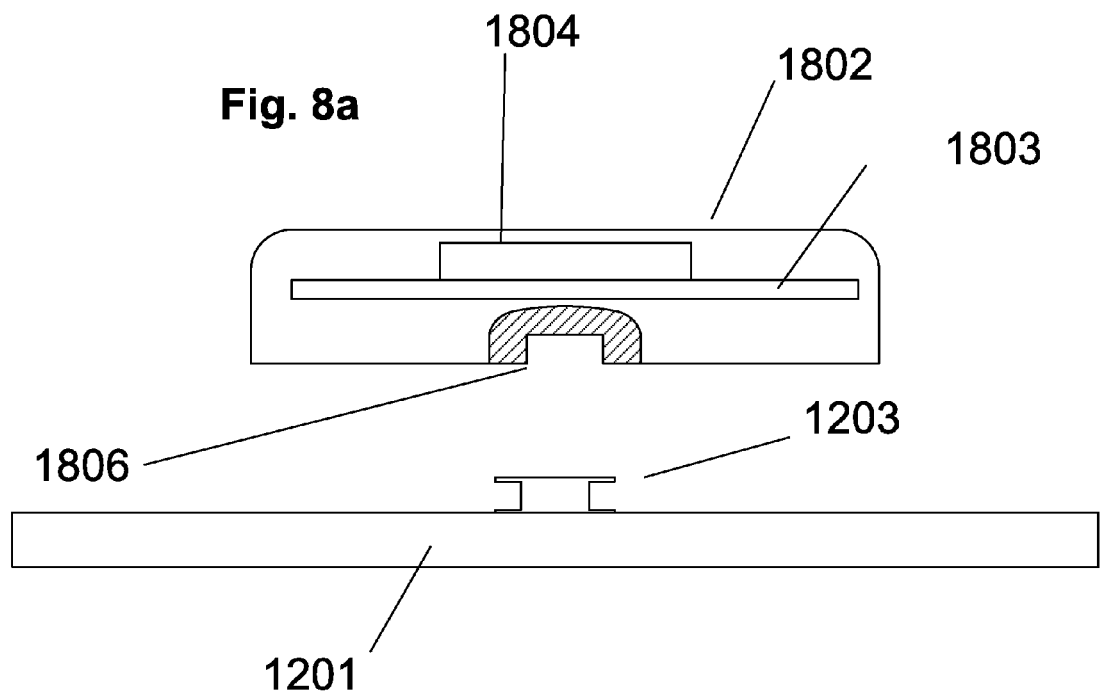

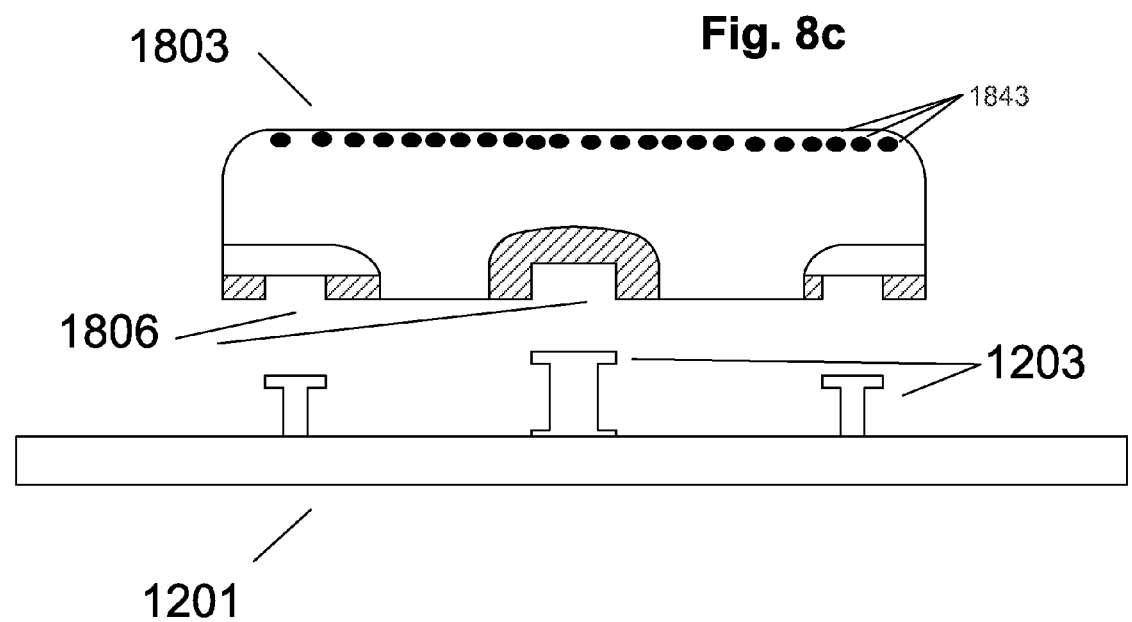
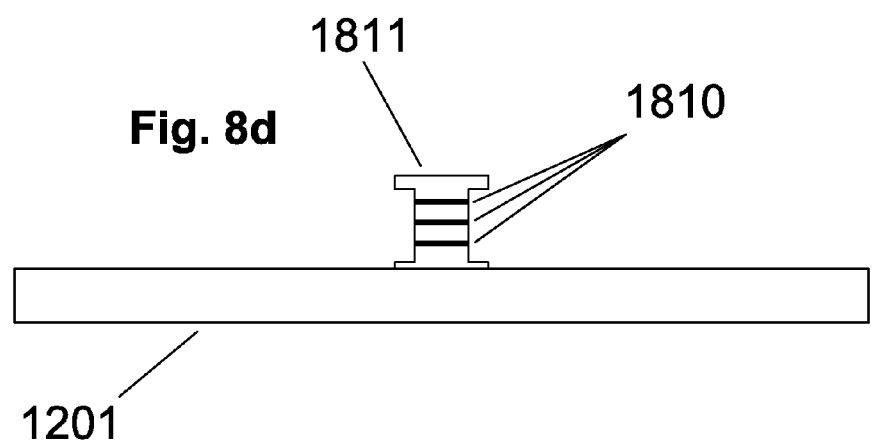

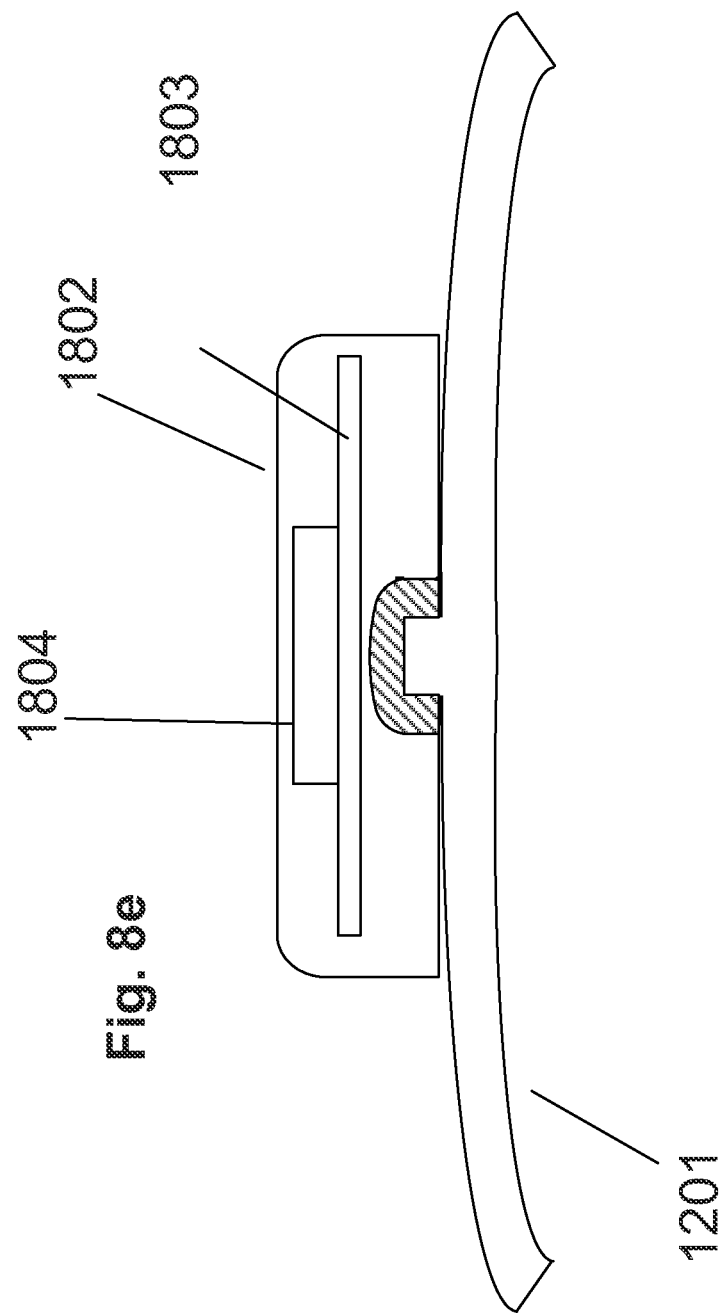

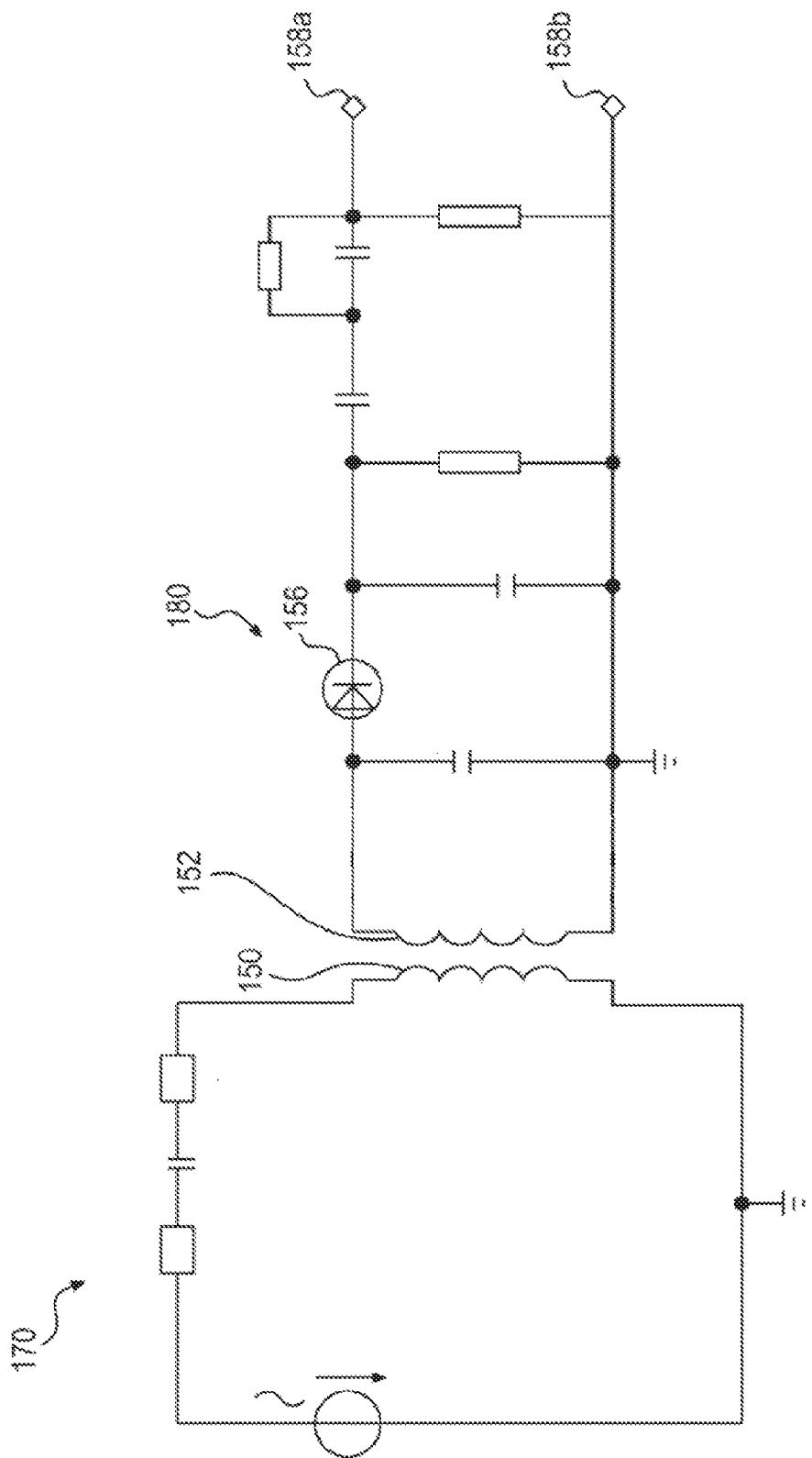

DEVICE AND METHOD FOR SNORING DETECTION AND CONTROL

RELATED APPLICATIONS

This application is a continuation-in-part application of application Ser. No. 14/041,598, filed Sep. 30, 2013 (pending), which is a continuation-in-part of application Ser. No. 13/629,690, filed on Sep. 28, 2012 (pending), application Ser. No. 13/629,694, filed on Sep. 28, 2012 (now U.S. Pat. No. 8,577,472), application Ser. No. 13/629,701, filed on Sep. 28, 2012 (now U.S. Pat. No. 8,588,941), application Ser. No. 13/629,712, filed on Sep. 28, 2012 (pending), application Ser. No. 13/629,725, filed on Sep. 28, 2012 (now U.S. Pat. No. 8,577,478), application Ser. No. 13/629,730, filed on Sep. 28, 2012 (now U.S. Pat. No. 8,577,465), application Ser. No. 13/629,741, filed on Sep. 28, 2012 (now U.S. Pat. No. 8,577,466), application Ser. No. 13/629,748, filed on Sep. 28, 2012 (now U.S. Pat. No. 8,700,183), application Ser. No. 13/629,757, filed on Sep. 28, 2012 (pending), application Ser. No. 13/629,762, filed on Sep. 28, 2012 (now U.S. Pat. No. 8,577,467), application Ser. No. 13/629,793, filed on Sep. 28, 2012 (now U.S. Pat. No. 8,577,468), application Ser. No. 13/629,819, filed on Sep. 28, 2012 now U.S. Pat. No. 8,718,776), application Ser. No. 13/630,392, filed on Sep. 28, 2012 (now U.S. Pat. No. 8,644,957), application Ser. No. 13/629,721, filed on Sep. 28, 2012 (now U.S. Pat. No. 8,574,164), and application Ser. No. 13/629,686, filed on Sep. 28, 2012 (now U.S. Pat. No. 8,577,464), each of which claims the benefit of priority under 35 U.S.C. §119(e) to U.S. Provisional Application No. 61/541,651, filed Sep. 30, 2011, and also to U.S. Provisional Application No. 61/657,424, filed Jun. 8, 2012. Additionally, application Ser. Nos. 13/629,686, and 13/629,721, are also continuations-in-part of both application Ser. No. 12/642,866, filed Dec. 21, 2009 (now U.S. Pat. No. 8,585,617), and of application Ser. No. 12/581,907, filed Oct. 20, 2009 (pending). This application also claims priority under 35 U.S.C. §119(e) to U.S. Provisional Application No. 61/836,089, filed Jun. 17, 2013. All of the above referenced applications are incorporated herein by reference in their entirety.

TECHNICAL FIELD

Embodiments of the present disclosure generally relate to devices and methods for modulating a nerve. More particularly, embodiments of the present disclosure relate to devices and methods for modulating a nerve through the delivery of energy via an implantable electrical modulator.

BACKGROUND

Neural modulation presents the opportunity to treat many physiological conditions and disorders by interacting with the body's own natural neural processes. Neural modulation includes inhibition (e.g. blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure. Neural modulation may provide the opportunity to treat several diseases or physiological conditions, a few examples of which are described in detail below.

Among the conditions to which neural modulation may be applied are sleep related breathing disorders, such as snoring and obstructive sleep apnea (OSA). OSA is a respiratory disorder characterized by recurrent episodes of partial or complete obstruction of the upper airway during sleep. During the sleep of a person without OSA, the pharyngeal muscles relax during sleep and gradually collapse, narrowing the airway. The airway narrowing limits the effectiveness of the sleeper's breathing, causing a rise in $CO_2$ levels in the blood. The increase in $CO_2$ results in the pharyngeal muscles contracting to open the airway to restore proper breathing. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In patients with OSA, the neuromuscular activity of the genioglossus muscle is decreased compared to normal individuals, accounting for insufficient response and contraction to open the airway as compared to a normal individual. This lack of response contributes to a partial or total airway obstruction, which significantly limits the effectiveness of the sleeper's breathing. In OSA patients, there are often several airway obstruction events during the night. Because of the obstruction, there is a gradual decrease of oxygen levels in the blood (hypoxemia). Hypoxemia leads to night time arousals, which may be registered by EEG, showing that the brain awakes from any stage of sleep to a short arousal. During the arousal, there is a conscious breath or gasp, which resolves the airway obstruction. An increase in sympathetic tone activity rate through the release of hormones such as epinephrine and noradrenaline also often occurs as a response to hypoxemia. As a result of the increase in sympathetic tone, the heart enlarges in an attempt to pump more blood and increase the blood pressure and heart rate, further arousing the patient. After the resolution of the apnea event, as the patient returns to sleep, the airway collapses again, leading to further arousals.

These repeated arousals, combined with repeated hypoxemia, leaves the patient sleep deprived, which leads to daytime somnolence and worsens cognitive function. This cycle can repeat itself up to hundreds of times per night in severe patients. Thus, the repeated fluctuations in and sympathetic tone and episodes of elevated blood pressure during the night evolve to high blood pressure through the entire day. Subsequently, high blood pressure and increased heart rate may cause other diseases.

Snoring in patients is frequently a result of a partially obstructed airway. Some patients experience relaxation of the pharyngeal muscles to a point that involves partial obstruction not significant enough to cause subsequent arousals during sleep. When the pharyngeal muscles relax and narrow the airway, air must travel through the airway at a higher velocity to maintain a similar volumetric flow rate. Higher velocity flows are more likely to be turbulent. These turbulent flows can cause vibrations in the tissue structure of the airway, producing an audible snoring effect. Snoring may have several adverse effects on both sufferers and those around them. Snoring may lead to hypopnea, a condition in which blood oxygen levels are decreased, resulting in shallower, less restful sleep. Snoring may also be associated with an increased risk of stroke and carotid artery atherosclerosis. Additionally, snoring may be detrimental to the sleep of those around the sufferer.

Efforts for treating both snoring and OSA include Continuous Positive Airway Pressure (CPAP) treatment, which requires the patient to wear a mask through which air is blown into the nostrils to keep the airway open. Other treatment options include the implantation of rigid inserts in the soft palate to provide structural support, tracheotomies, or tissue ablation.

Another condition to which neural modulation may be applied is the occurrence of migraine headaches. Pain sensation in the head is transmitted to the brain via the occipital nerve, specifically the greater occipital nerve, and the trigeminal nerve. When a subject experiences head pain, such as during a migraine headache, the inhibition of these nerves may serve to decrease or eliminate the sensation of pain.

Neural modulation may also be applied to hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g. through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

The foregoing are just a few examples of conditions to which neuromodulation may be of benefit, however embodiments of the invention described hereafter are not necessarily limited to treating only the above-described conditions.

SUMMARY

Some embodiments may include a device for the treatment of snoring. The device may include a flexible substrate configured for removable attachment to a subject's skin, a primary antenna disposed on the flexible substrate, an interface configured to receive a feedback signal that varies based upon a breathing pattern of the subject; and at least one processing device. The processing device may be configured to analyze the feedback signal and determine whether the subject is snoring based on the analysis of the feedback signal, and if snoring is detected, cause a hypoglossal nerve modulation control signal to be applied to the primary antenna in order to wirelessly transmit the hypoglossal nerve modulation control signal to a secondary antenna associated with an implant unit configured for location in a body of the subject.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIGS. 4a and 4b illustrate an exemplary embodiment of an external unit.

FIGS. 5a and 5b illustrate a double-layer crossover antenna.

FIG. 7 illustrates an embodiment of a carrier including removable tabs.

FIGS. 8a-f illustrate alternate embodiments of a carrier and electronics housing.

FIG. 14 illustrates circuitry of an implant unit and an external unit, according to an exemplary embodiment of the present disclosure.

DESCRIPTION OF EXEMPLARY EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to a device for modulating a nerve through the delivery of energy. Nerve modulation, or neural modulation, includes inhibition (e.g. blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may including providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied.

In patients that suffer from a sleep breathing disorder, for example, a primary target response of nerve stimulation may include contraction of a tongue muscle (e.g., the muscle) in order to move the tongue to a position that does not block the patient's airway. In the treatment of migraine headaches, nerve inhibition may be used to reduce or eliminate the sensation of pain. In the treatment of hypertension, neural modulation may be used to increase, decrease, eliminate or otherwise modify nerve signals generated by the body to regulate blood pressure.

While embodiments of the present disclosure may be disclosed for use in patients with specific conditions, the embodiments may be used in conjunction with any patient/portion of a body where nerve modulation may be desired. That is, in addition to use in patients with a sleep breathing disorder, migraine headaches, or hypertension, embodiments of the present disclosure may be used in many other areas, including, but not limited to: deep brain stimulation (e.g., treatment of epilepsy, Parkinson's, and depression); cardiac pace-making, stomach muscle stimulation (e.g., treatment of obesity), back pain, incontinence, menstrual pain, and/or any other condition that may be affected by neural modulation.

Figure 1:
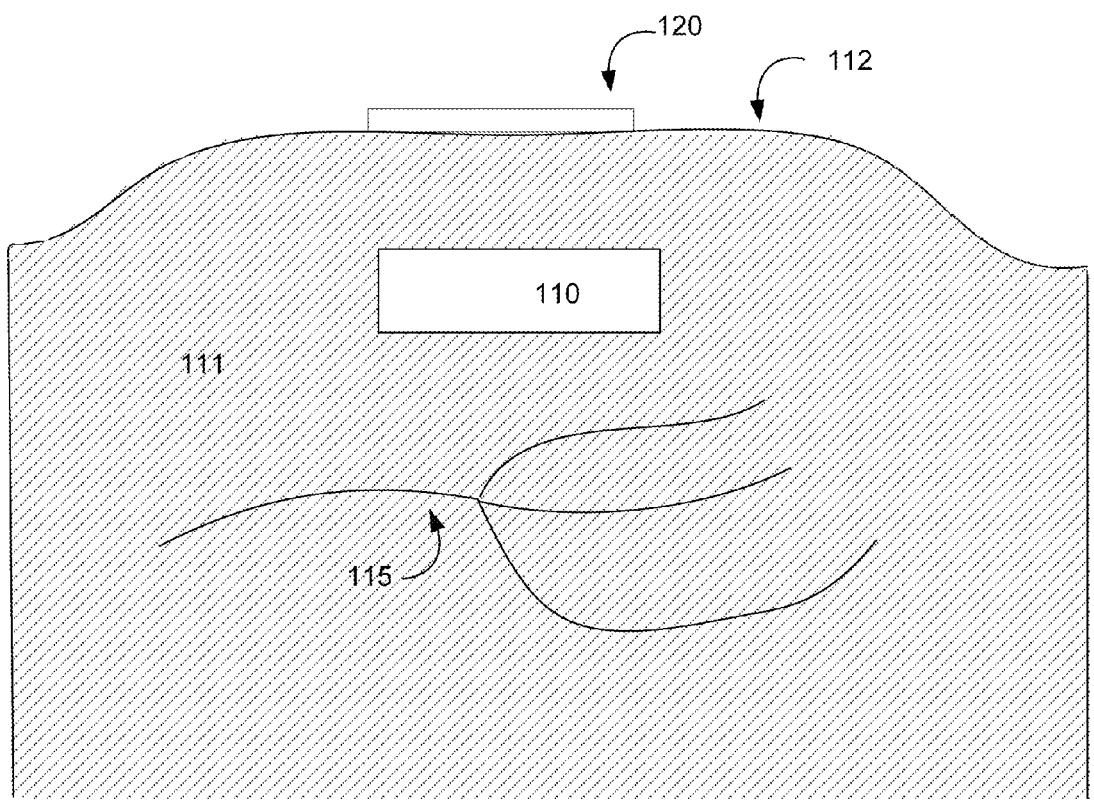
FIG. 1 schematically illustrates an implant unit and external unit, according to an exemplary embodiment of the present disclosure.

FIG. 1 illustrates an implant unit and external unit, according to an exemplary embodiment of the present disclosure. An implant unit 110, may be configured for implantation in a subject, in a location that permits it to modulate a nerve 115. The implant unit 110 may be located in a subject such that intervening tissue 111 exists between the implant unit 110 and the nerve 115. Intervening tissue may include muscle tissue, connective tissue, organ tissue, or any other type of biological tissue. Thus, location of implant unit 110 does not require contact with nerve 115 for effective neuromodulation. The implant unit 110 may also be located directly adjacent to nerve 115, such that no intervening tissue 111 exists.

In treating a sleep breathing disorder, implant unit 110 may be located on a genioglossus muscle of a patient. Such a location is suitable for modulation of the hypoglossal nerve, branches of which run inside the genioglossus muscle. Implant unit 110 may also be configured for placement in other locations. For example, migraine treatment may require subcutaneous implantation in the back of the neck, near the hairline of a subject, or behind the ear of a subject, to modulate the greater occipital nerve and/or the trigeminal nerve. Treating hypertension may require the implantation of a neuromodulation implant intravascularly inside the renal artery or renal vein (to modulate the parasympathetic renal nerves), either unilaterally or bilaterally, inside the carotid artery or jugular vein (to modulate the glossopharyngeal nerve through the carotid baroreceptors). Alternatively or additionally, treating hypertension may require the implantation of a neuromodulation implant subcutaneously, behind the ear or in the neck, for example, to directly modulate the glossopharyngeal nerve.

External unit 120 may be configured for location external to a patient, either directly contacting, or close to the skin 112 of the patient. External unit 120 may be configured to be affixed to the patient, for example, by adhering to the skin 112 of the patient, or through a band or other device configured to hold external unit 120 in place. Adherence to the skin of external unit 120 may occur such that it is in the vicinity of the location of implant unit 110.

Figure 2:
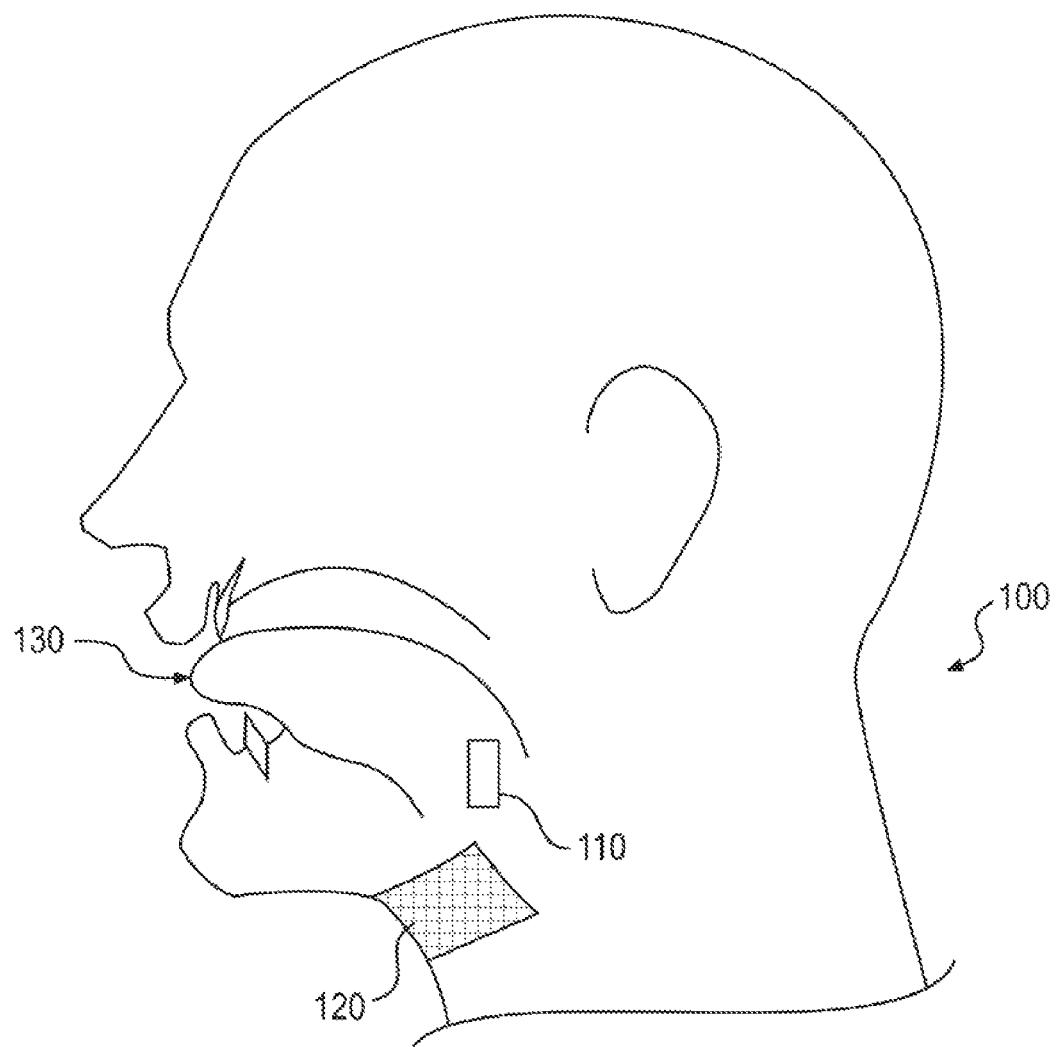
FIG. 2 is a partially cross-sectioned side view of a subject with an implant unit and external unit, according to an exemplary embodiment of the present disclosure.

FIG. 2 illustrates an exemplary embodiment of a neuromodulation system for delivering energy in a patient 100 with a sleep breathing disorder. The system may include an external unit 120 that may be configured for location external to the patient. As illustrated in FIG. 2, external unit 120 may be configured to be affixed to the patient 100. FIG. 2 illustrates that in a patient 100 with a sleep breathing disorder, the external unit 120 may be configured for placement underneath the patient's chin and/or on the front of patient's neck. The suitability of placement locations may be determined by communication between external unit 120 and implant unit 110, discussed in greater detail below. In alternate embodiments, for the treatment of conditions other than a sleep breathing disorder, the external unit may be configured to be affixed anywhere suitable on a patient, such as the back of a patient's neck, i.e. for communication with a migraine treatment implant unit, on the outer portion of a patient's abdomen, i.e. for communication with a stomach modulating implant unit, on a patient's back, i.e. for communication with a renal artery modulating implant unit, and/or on any other suitable external location on a patient's skin, depending on the requirements of a particular application.

External unit 120 may further be configured to be affixed to an alternative location proximate to the patient. For example, in one embodiment, the external unit may be configured to fixedly or removably adhere to a strap or a band that may be configured to wrap around a part of a patient's body. Alternatively, or in addition, the external unit may be configured to remain in a desired location external to the patient's body without adhering to that location.

The external unit 120 may include a housing. The housing may include any suitable container configured for retaining components. In addition, while the external unit is illustrated schematically in FIG. 2, the housing may be any suitable size and/or shape and may be rigid or flexible. Non-limiting examples of housings for the external unit 100 include one or more of patches, buttons, or other receptacles having varying shapes and dimensions and constructed of any suitable material. In one embodiment, for example, the housing may include a flexible material such that the external unit may be configured to conform to a desired location. For example, as illustrated in FIG. 2, the external unit may include a skin patch, which, in turn, may include a flexible substrate. The material of the flexible substrate may include, but is not limited to, plastic, silicone, woven natural fibers, and other suitable polymers, copolymers, and combinations thereof. Any portion of external unit 120 may be flexible or rigid, depending on the requirements of a particular application.

As previously discussed, in some embodiments external unit 120 may be configured to adhere to a desired location. Accordingly, in some embodiments, at least one side of the housing may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions.

Figure 3:
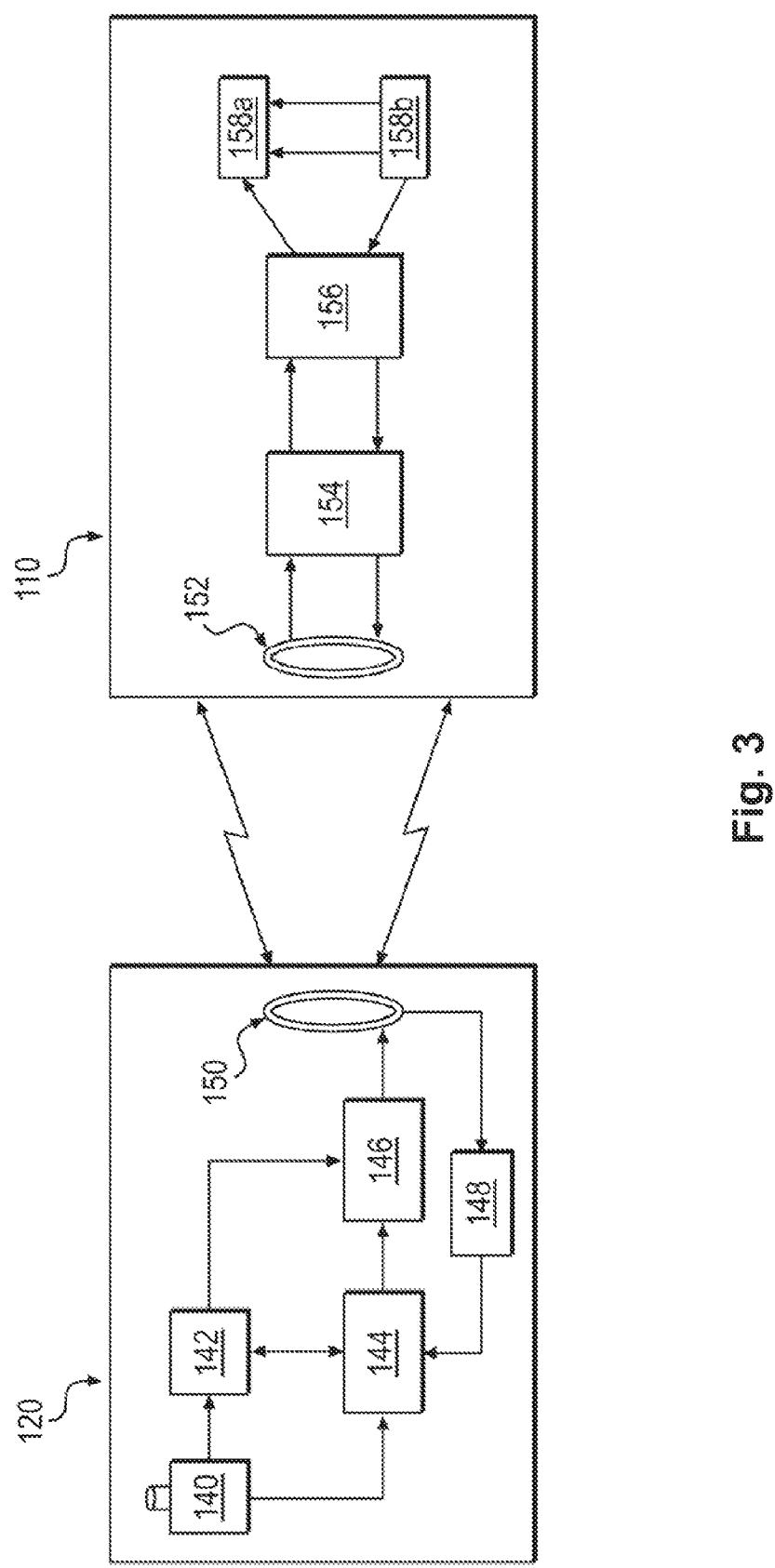
FIG. 3 schematically illustrates a system including an implant unit and an external unit, according to an exemplary embodiment of the present disclosure.

FIG. 3 schematically illustrates a system including external unit 120 and an implant unit 110. In some embodiments, internal unit 110 may be configured as a unit to be implanted into the body of a patient, and external unit 120 may be configured to send signals to and/or receive signals from implant unit 110.

As shown in FIG. 3, various components may be included within a housing of external unit 120 or otherwise associated with external unit 120. As illustrated in FIG. 3, at least one processor 144 may be associated with external unit 120. For example, the at least one processor 144 may be located within the housing of external unit 120. In alternative embodiments, the at least one processor may be configured for wired or wireless communication with the external unit from a location external to the housing.

The at least one processor may include any electric circuit that may be configured to perform a logic operation on at least one input variable. The at least one processor may therefore include one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

FIG. 3 illustrates that the external unit 120 may further be associated with a power source 140. The power source may be removably couplable to the external unit at an exterior location relative to external unit. Alternatively, as shown in FIG. 3, power source 140 may be permanently or removably coupled to a location within external unit 120. The power source may further include any suitable source of power configured to be in electrical communication with the processor. In one embodiment, for example the power source 140 may include a battery.

The power source may be configured to power various components within the external unit. As illustrated in FIG. 3, power source 140 may be configured to provide power to the processor 144. In addition, the power source 140 may be configured to provide power to a signal source 142. The signal source 142 may be in communication with the processor 144 and may include any device configured to generate a signal (e.g., a sinusoidal signal, square wave, triangle wave, microwave, radio-frequency (RF) signal, or any other type of electromagnetic signal). Signal source 142 may include, but is not limited to, a waveform generator that may be configured to generate alternating current (AC) signals and/or direct current (DC) signals. In one embodiment, for example, signal source 142 may be configured to generate an AC signal for transmission to one or more other components. Signal source 142 may be configured to generate a signal of any suitable frequency. In some embodiments, signal source 142 may be configured to generate a signal having a frequency of from about 6.5 MHz to about 13.6 MHz. In additional embodiments, signal source 142 may be configured to generate a signal having a frequency of from about 7.4 to about 8.8 MHz. In further embodiments, signal source 142 may generate a signal having a frequency as low as 90 kHz or as high as 28 MHz.

Signal source 142 may be configured for direct or indirect electrical communication with an amplifier 146. The amplifier may include any suitable device configured to amplify one or more signals generated from signal source 142. Amplifier 146 may include one or more of various types of amplification devices, including, for example, transistor based devices, operational amplifiers, RF amplifiers, power amplifiers, or any other type of device that can increase the gain associated one or more aspects of a signal. The amplifier may further be configured to output the amplified signals to one or more components within external unit 120.

External unit may 120 additionally include a memory unit 143. Processor 144 may communicate with memory unit 143, for example, to store and retrieve data. Stored and retrieved data may include, for example, information about therapy parameters and information about implant unit 110 and external unit 120. The use of memory unit 143 is explained in greater detail below. Memory unit 143 may be any suitable for of non-transient computer readable storage medium, External unit 120 may also include communications interface 145, which may be provided to permit external unit 120 to communicate with other devices, such as programming devices and data analysis device. Further details regarding communications interface 145 are included below.

The external unit may additionally include a primary antenna 150. The primary antenna may be configured as part of a circuit within external unit 120 and may be coupled either directly or indirectly to various components in external unit 120. For example, as shown in FIG. 3, primary antenna 150 may be configured for communication with the amplifier 146.

The primary antenna may include any conductive structure that may be configured to create an electromagnetic field. The primary antenna may further be of any suitable size, shape, and/or configuration. The size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. The primary antenna may include any suitable antenna known to those skilled in the art that may be configured to send and/or receive signals. Suitable antennas may include, but are not limited to, a long-wire antenna, a patch antenna, a helical antenna, etc. In one embodiment, for example, as illustrated in FIG. 3, primary antenna 150 may include a coil antenna. Such a coil antenna may be made from any suitable conductive material and may be configured to include any suitable arrangement of conductive coils (e.g., diameter, number of coils, layout of coils, etc.). A coil antenna suitable for use as primary antenna 150 may have a diameter of between about 1 cm and 10 cm, and may be circular or oval shaped. In some embodiments, a coil antenna may have a diameter between 5 cm and 7 cm, and may be oval shaped. A coil antenna suitable for use as primary antenna 150 may have any number of windings, e.g. 4, 8, 12, or more. A coil antenna suitable for use as primary antenna 150 may have a wire diameter between about 0.1 mm and 2 mm. These antenna parameters are exemplary only, and may be adjusted above or below the ranges given to achieve suitable results.

As noted, implant unit 110 may be configured to be implanted in a patient's body (e.g., beneath the patient's skin). FIG. 2 illustrates that the implant unit 110 may be configured to be implanted for modulation of a nerve associated with a muscle of the subject's tongue 130. Modulating a nerve associated with a muscle of the subject's tongue 130 may include stimulation to cause a muscle contraction. In further embodiments, the implant unit may be configured to be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e. the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

Implant unit 110 may be formed of any materials suitable for implantation into the body of a patient. In some embodiments, implant unit 110 may include a flexible carrier 161 (FIG. 4) including a flexible, biocompatible material. Such materials may include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a thickness suitable for implantation under a patient's skin. Implant 110 may have thickness of less than about 4 mm or less than about 2 mm.

Other components that may be included in or otherwise associated with the implant unit are illustrated in FIG. 3. For example, implant unit 110 may include a secondary antenna 152 mounted onto or integrated with flexible carrier 161. Similar to the primary antenna, the secondary antenna may include any suitable antenna known to those skilled in the art that may be configured to send and/or receive signals. The secondary antenna may include any suitable size, shape, and/or configuration. The size, shape and/or configuration may be determined by the size of the patient, the placement location of the implant unit, the amount of energy required to modulate the nerve, etc. Suitable antennas may include, but are not limited to, a long-wire antenna, a patch antenna, a helical antenna, etc. In some embodiments, for example, secondary antenna 152 may include a coil antenna having a circular shape (see also FIG. 10) or oval shape. Such a coil antenna may be made from any suitable conductive material and may be configured to include any suitable arrangement of conductive coils (e.g., diameter, number of coils, layout of coils, etc.). A coil antenna suitable for use as secondary antenna 152 may have a diameter of between about 5 mm and 30 mm, and may be circular or oval shaped. A coil antenna suitable for use as secondary antenna 152 may have any number of windings, e.g. 4, 15, 20, 30, or 50. A coil antenna suitable for use as secondary antenna 152 may have a wire diameter between about 0.01 mm and 1 mm. These antenna parameters are exemplary only, and may be adjusted above or below the ranges given to achieve suitable results.

FIGS. 4a and 4b illustrate an exemplary embodiment of external unit 120, including features that may be found in any combination in other embodiments. FIG. 4a illustrates a side view of external unit 120, depicting carrier 1201 and electronics housing 1202.

Carrier 1201 may include a skin patch configured for adherence to the skin of a subject, for example through adhesives of mechanical means. Carrier 1201 may be flexible or rigid, or may have flexible portions and rigid portions. Carrier 1201 and may include a primary antenna 150, for example, a double-layer crossover antenna 1101 such as that illustrated in FIGS. 5a and 5b. Carrier 1201 may also include power source 140, such as a paper battery, thin film battery, or other type of substantially flat and/or flexible battery. Carrier 1201 may also include any other type of battery or power source. Carrier 1201 may also include a connector 1203 configured for selectively or removably connecting carrier 1201 to electronics housing 1202. Connector 1203 may extend or protrude from carrier 1201. Connector 1203 may be configured to be received by a recess 1204 of electronics housing 1202 Connector 1203 may be configured as a non-pouch connector, configured to provide a selective connection to electronics housing 1204 without the substantial use of concave feature. Connector 1203 may include, for example a peg, and may have flexible arms. Connector 1203 may further include a magnetic connection, a velcro connection, and/or a snap dome connection. Connector 1203 may also include a locating feature, configured to locate electronics housing 1202 at a specific height, axial location, and/or axial orientation with respect to carrier 1201. A locating feature of connector 1203 may further include pegs, rings, boxes, ellipses, bumps, etc. Connector 1203 may be centered on carrier 1201, may be offset from the center by a predetermined amount, or may be provided at any other suitable location of carrier 1201. Multiple connectors 1203 may be provided on carrier 1201. Connector 1203 may be configured such that removal from electronics housing 1202 causes breakage of connector 1203. Such a feature may be desirable to prevent re-use of carrier 1201, which may lose some efficacy through continued use.

Direct contact between primary antenna 150 and the skin of a subject may result in alterations of the electrical properties of primary antenna 150. This may be due to two effects. First, the skin of a subject is a resistive volume conductor, and creating electrical contact between primary antenna 150 and the skin may result in the skin becoming part of an electric circuit including the primary antenna. Thus, when primary antenna 150 is energized, current may flow through the skin, altering the electrical properties of primary antenna 150. Second, when the subject sweats, the generated moisture may also act as a resistive conductor, creating electrical pathways that did not exist previously. These effects may occur even when there is no direct contact between the primary antenna 150 and the skin, for example, when an adhesive layer is interposed between the primary antenna 150 and the skin. Because many adhesives are not electrically insulating, and may absorb moisture from a subject's skin, these effects can occur without direct contact between the antenna and the skin. In some embodiments, processor 144 may be configured to detect the altered properties of primary antenna 150 and take these into account when generating modulation and sub-modulation control signals for transmission to an implant unit 110.

Figure 6A:
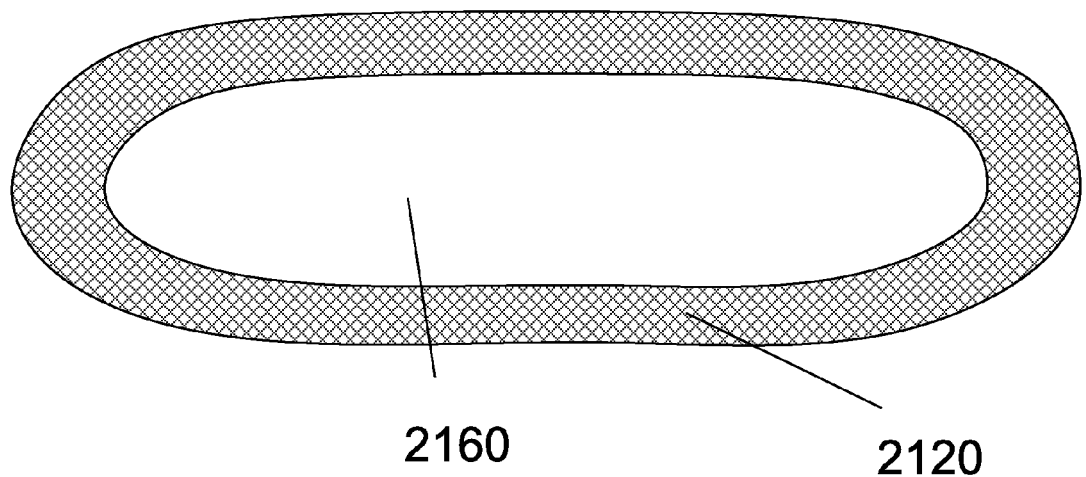
FIG. 6a illustrates an embodiment of a carrier as viewed from the bottom.
Figure 6B:
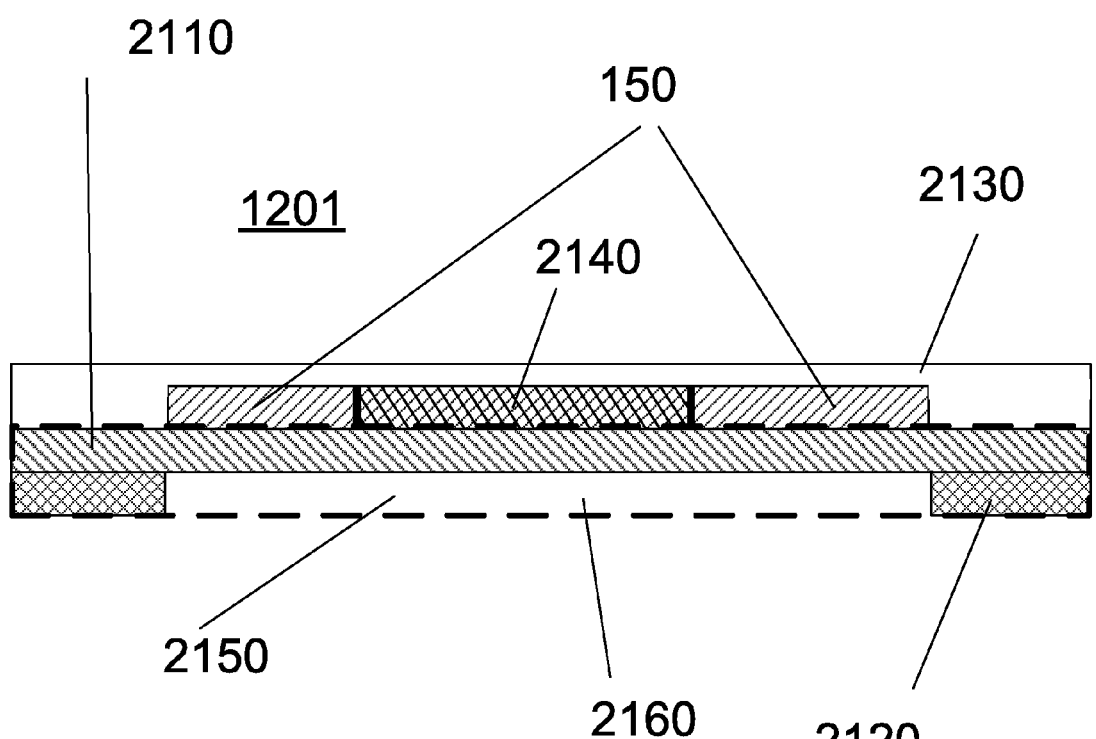
FIG. 6b illustrates an embodiment of a carrier in cross section.

In some embodiments, carrier 1201 may include a buffered antenna, as illustrated in FIGS. 6a-b and 22 (not drawn to scale), to counteract (e.g., reduce or eliminate) the above-described effects. FIG. 6a illustrates an embodiment of carrier 1201 as viewed from the bottom. FIG. 6b illustrates an embodiment of carrier 1201 in cross section. Carrier 1201 may include one or more structures for separating an antenna from the skin of a subject. In some embodiments, carrier 1201 may include a buffer layer 2150 that provides an air gap 2160 between the skin of a subject and the antenna. Carrier 1201 may also include a top layer 2130 and a top center region 2140.

As illustrated in FIGS. 6a-b, buffer layer 2150 may be disposed on the flexible carrier at a position so as to be between the antenna and the skin of the subject when carrier 1201 is in use. Buffer layer 2150 may include any suitable material or structure to provide or establish an air gap 2160 between the antenna 150 and the skin of the subject. As used herein, air gap 2160 may include any space, area, or region between the skin of the subject and antenna 150 not filled by a solid material. In some embodiments, buffer layer 2150 may include a single layer. In other embodiments, buffer layer 2150 may include multiple sub-layers (e.g., two, three, or more sub-layers). In still other embodiments, buffer layer 2150 may include an extension of one or more structures associated with carrier 1201 in order to move antenna 150 away from a subject's skin.

The air gap 2160 provided may be contiguous or may reside within or among various structures associated with buffer layer 2150. For example, in some embodiments, air gap 2160 may include a space or region free or relatively free of structures, such as air gap 2160 shown in FIG. 6b, which includes an air filled volume created between the skin of the subject and antenna 150 by the structure of buffer layer 2150. In other embodiments, air gap 2160 may be formed within or between structures associated with buffer layer 2150. For example, air gap 2160 may be formed by one or more porous materials, including open or close cell foams, fibrous mats, woven materials, fabrics, perforated sheet materials, meshes, or any other material or structure having air spaces within boundaries of the material or structure. Further, buffer layer 2150 may include dielectric materials, hydrophobic closed cell foams, open celled foams, cotton and other natural fibers, porous cellulose based materials, synthetic fibers, and any other material or structure suitable for establishing air gap 2160.

Air gap 2160 need not contain only air. Rather, other materials, fluids, or gases may be provided within air gap 2160. For example, in some cases, air gap 2160 may include carbon dioxide, nitrogen, argon, or any other suitable gases or materials.

FIGS. 6a and 6b provide a diagrammatic depiction of a carrier 1201 including an exemplary buffer layer 2150, consistent with the present disclosure. In the structure shown if FIGS. 6a and 6b, air gap 2160 is provided by a buffer layer 2150 having multiple sub-layers. Specifically, buffer layer 2150 may include a separation sub-layer 2110 and an adhesive sub-layer 2120. Separation sub-layer 2110, which may or may not be included in buffer layer 2150, may include any structure for isolating or otherwise separating antenna 150 from a surface of the subject's skin. In the embodiment shown in FIGS. 6a and 6b, air gap 2160 may be established through patterning of adhesive sub-layer 2120. For example, as shown, adhesive sub-layer 2120 may be disposed around a perimeter of separation sub-layer 2110, and air gap 2160 may be established in a region in the middle of adhesive sub-layer 2120. Of course, other configurations of adhesive sub-layer 2120 may also be possible. For example, air gap 2160 may be formed between any pattern of features associated with adhesive sub-layer 2120, including, for example, adhesive stripes, dots, meshes, etc. For example, adhesive sub-layer 2120 may include a series of discrete adhesive dots or lines, a mesh-pattern of adhesive material, or any other pattern suitable for establishing air gap 2160

While in some embodiments, air gap 2160 may be established by adhesive sub-layer 2120 or by any other sub-layer of buffer layer 2150, in other embodiments, air gap 2160 may be established by separation sub-layer 2110. In such embodiments, separation sub-layer 2110 may be made to include various patterns (e.g., perforations, meshes, islands, bumps, pillars, etc.) to provide air gap 2160. Separation sub-layer 2110 may also be formed of a various types of materials. For example, separation sub-layer 2110 may include open or closed cell foam, fabric, paper, perforated sheet materials, or any other material suitable for providing air gaps or spaces therewithin. Separation sub-layer 2110 may be formed of insulating material, such as a dielectric material.

In some embodiments, buffer layer 2150 may be formed by extensions of another layer (e.g., a top layer 2130) associated with carrier 1201. For example, top layer 2130 may include legs or extension portions that extend below antenna 150 such that when in use, antenna 150 is positioned at a location above the subject's skin.

Air gap 2160 may have any suitable dimensions. In some embodiments, air gap 2160 may be between 250 microns 1 mm in height. In other embodiments air gap 2160 may be between 1 mm and 5 mm in height.

The buffered antenna, as illustrated in FIGS. 6a and 6b may serve to electrically insulate and/or isolate primary antenna 150 from the skin and/or the sweat of a subject, thus eliminating or reducing the alterations to electrical properties of the antenna that may result from contact with the skin and/or sweat of the subject. A buffered antenna may be constructed with either or both of buffered layer 2110 and air gap 2160 disposed within window region 2150.

In some embodiments, carrier 1201 may be provided with removable tabs, as shown in FIG. 7 for altering a size of the carrier. Users of carrier 1201 differ significantly in size and shape. Some users may have larger neck and/or chin areas, some may have smaller. Some users may find require more adhesive area to maintain comfort during a therapeutic period. To accommodate various preferences, carrier 1201 may be provided with removable tabs 2220 at either end, wherein the tabs are provided with a perforated detachment portion where they connect to the carrier 1201. A user who desires the increased adhesive area may leave the tabs intact, while a user desiring a smaller adhesive area may tear the tabs 2220 along the perforated detachment portion to remove them. In alternative embodiments, tabs 2220 may be sized and shape to accommodate the thumbs of a user. In still other embodiments, non-removable tabs sized and shaped to accommodate the thumbs of a user may be provided. In some embodiments, removable tabs 2220 may be provided without adhesive, to be used during attachment of carrier 1201 and subsequently removed. Non-adhesive removable tabs 2220 may permit a user to hold carrier 1201 without accidentally sticking it to their fingers.

Returning now to FIGS. 4a and 4b, electronics housing 1202 is illustrated in side view in FIG. 4a and in a bottom view in FIG. 4b. Electronics housing 1202 may include electronics portion 1205, which may be arranged inside electronics housing 1202 in any manner that is suitable. Electronics portion 1205 may include various components, further discussed below, of external unit 120. For example, electronics portion 1205 may include any combination of at least one processor 144 associated with external unit 120, a power source 140, such as a battery, a primary antenna 152, and an electrical circuit 170. Electronics portion 1205 may also include any other component described herein as associated with external unit 120. Additional components may also be recognized by those of skill in the art.

Electronics housing 1202 may include a recess 1204 configured to receive connector 1203. Electronics housing 1202 may include at least one electrical connector 1210, 1211, 1212. Electrical connectors 1210, 1211, 1212 may be arranged with pairs of electrical contacts, as shown in FIG. 4b, or with any other number of electrical contacts. The pair of electrical contacts of each electrical connector 1210, 1211, 1212 may be continuously electrically connected with each other inside of housing 1202, such that the pair of electrical contacts represents a single connection point to a circuit. In such a configuration, it is only necessary that one of the electrical contacts within a pair be connected. Electrical connectors 1210, 1211, and 1212 may thus include redundant electrical contacts. The electrical contacts of each electrical connector 1210, 1211, 1212 may also represent opposite ends of a circuit, for example, the positive and negative ends of a battery charging circuit. In an exemplary embodiment, as shown in FIG. 4b, electrical connectors 1210, 1211, and 1212 are configured so as to maintain electrical contact with an exposed electrical contact portion 1108 independent of an axial orientation of electronics housing 1202. Connection between any or all of electrical connectors 1210, 1211, 1212 and exposed electrical contact portions 1108 may thus be established and maintained irrespective of relative axial positions of carrier 1201 and housing 1202. Thus, when connector 1203 is received by recess 1204, housing 1202 may rotate with respect to carrier 1201 without interrupting electrical contact between at least one of electrical connectors 1210, 1211, 1212 and exposed electrical contact portions 1108. Axial orientation independence may be achieved, for example, through the use of circular exposed electrical contact portions 1108 and each of a pair of contacts of electrical connectors 1210, 1211, 1212 disposed equidistant from a center of recess 1204 at a radius approximately equal to that of a corresponding exposed electrical contact portion 1108. In this fashion, even if exposed electrical contact portion 1108 includes a discontinuous circle, at least one electrical contact of electrical connectors 1210, 1211, and 1212 may make contact. In FIG. 4b, electrical connectors 1210, 1211, 1212 are illustrated as pairs of rectangular electrical contacts. Electrical connectors 1210, 1211, 1212, however, may include any number of contacts, be configured as continuous or discontinuous circles, or have any other suitable shape or configuration.

One exemplary embodiment may operate as follows. As shown in FIG. 4b, electronics housing 1202 may include more electrical connectors 1210, 1211, 1212, than a carrier 1201 includes exposed electrical contact portions 1108. In the illustrated embodiments, electronics housing 1202 includes three electrical connectors 1210, 1211, and 1212, while a double-layer crossover antenna 1101 includes two exposed electrical contact portions 1108. In such an embodiment, two electrical connectors 1211 and 1212 may be configured with continuously electrically connected electrical contacts, such that each connector makes contact with a different exposed electrical contact portion 1108, where the exposed electrical contact portions 1108 represent opposite ends of double layer crossover antenna 1101. Thus, antenna 1101 may be electrically connected to the electrical components contained in electronics portion 1205. When connected to carrier 1201 in this configuration, electrical connectors 1210 may not make contact with any electrodes. In this embodiment, electrical connectors 1210 may be reserved to function as opposite ends of a battery charging circuit, in order to charge a battery contained in electronics portion 1205 when electronics housing 1202 is not being used for therapy. A battery charger unit may be provided with a non-breakable connector similar to that of non-pouch connector 1203, and configured to engage with recess 1204. Upon engaging with recess 1204, electrode contacts of the battery charger unit may contact electrical connectors 1210 to charge a battery contained within electronics portion 1205.

In an additional embodiment consistent with the present disclosure, an activator chip may include electronics housing 1202. Processor 144 may be configured to activate when at least one of electrical connectors 1210, 1211, 1212 contact exposed electrical contact portions 1108 included in carrier 1201. In this manner, an electronics housing 1202 may be charged and left dormant for many days prior to activation. Simply connecting electronics housing 1202 to carrier 1201 (and inducing contact between an electrical connector 1210, 1211, 1212 and an electrode portion 1108) may cause the processor to activate. Upon activation, processor 144 may be configured to enter a specific mode of operation, such as a calibration mode (for calibrating the processor after placement of the carrier on the skin), a placement mode (for assisting a user to properly place the carrier on the skin), and/or a therapy mode (to begin a therapy session). The various modes of processor 144 may include waiting periods at the beginning, end, or at any time during. For example, a placement mode may include a waiting period at the end of the mode to provide a period during which a subject may fall asleep. A therapy mode may include a similar waiting period at the beginning of the mode. Additionally or alternatively, processor 144 may be configured to provide waiting periods separate from the described modes, in order to provide a desired temporal spacing between system activities.

In some embodiments, housing 1202 may include features to communicate with a user. For example, one or more LED lights and/or one or more audio devices may be provided. LEDs and audio devices may be provided to communicate various pieces of information to a user, such as low battery warnings, indications of activity, malfunction alerts, indications of connectivity (e.g. connections to electrical components on carrier 1201).

Another embodiment consistent with the present disclosure may include a flexible electronics housing 1802. FIGS. 8a-8f illustrates an embodiment including a flexible electronics housing 1802. Utilizing flexible electronics housing 1802 may provide benefits with respect to the size and shape of the electronics housing component. An electronics housing must be large enough to accommodate the various components contained inside, such as electronic circuitry and a battery. It may be beneficial to house the necessary components in a flexible electronics housing 1802 with increased lateral dimensions and decreased vertical dimensions, in order to create a more comfortable experience for a user. A lower profile flexible electronics housing 1802 may also be less likely to catch its edges on bedclothes during a sleeping period. Additionally, when increasing lateral dimensions, it may be beneficial for the housing to be flexible, so as to better conform to the body contour of the wearer. Flexible electronics housing 1802 may be achieved through the use of flexible components, such as a flexible circuit board 1803 accommodating processor 144. Flexible electronics housing 1802 may be between 10 and 50 mm in height, and may be at least three times wider in a lateral dimension than in a height dimension. In one embodiment, flexible electronics housing 1802 may be elliptical in shape, 14 mm high and having elliptical diameters of 40 mm and 50 mm.

Flexible electronics housing 1802 may further include all of the same functionality and components as described above with respect to electronics housing 1202, for example, battery 1804, electrical connectors 1805 (not shown), and recess 1806. Flexible electronics housing 1802 may also be configured to contain a primary antenna. Recess 1806 may be a connection portion configured to engage with a non-pouch connector 1203 of carrier 1201. Some embodiments may include a plurality of recesses 1806, for example, two or four recesses located near edges of the housing, as shown in FIG. 8b, or a centrally located recess and a plurality of recess located near edges of the housing, as shown in FIG. 8c. The flexibility of flexible electronics housing 1802 may permit the housing to better conform to the contours of a patient's body when secured via connector 1203 and carrier 1201. Flexible electronics housing 1802 may include a rigid portion 1807 in the center in which electrical connectors 1805 are located. Rigid portion 1807 may be substantially inflexible. Rigid portion 1807 may ensure that electrical connectors 1805 maintain contact with exposed electrical contact portions 1108 of carrier 1201. Rigid portion 1807 may also accommodate a rigid battery 1804, or any other component in the housing required to be rigid. In some embodiments, battery 1804 may provide the structure that ensures the rigidity of rigid portion 1807. Any combination of the components within flexible housing 1802 may be flexible and/or rigid as required.

Figure 8F:
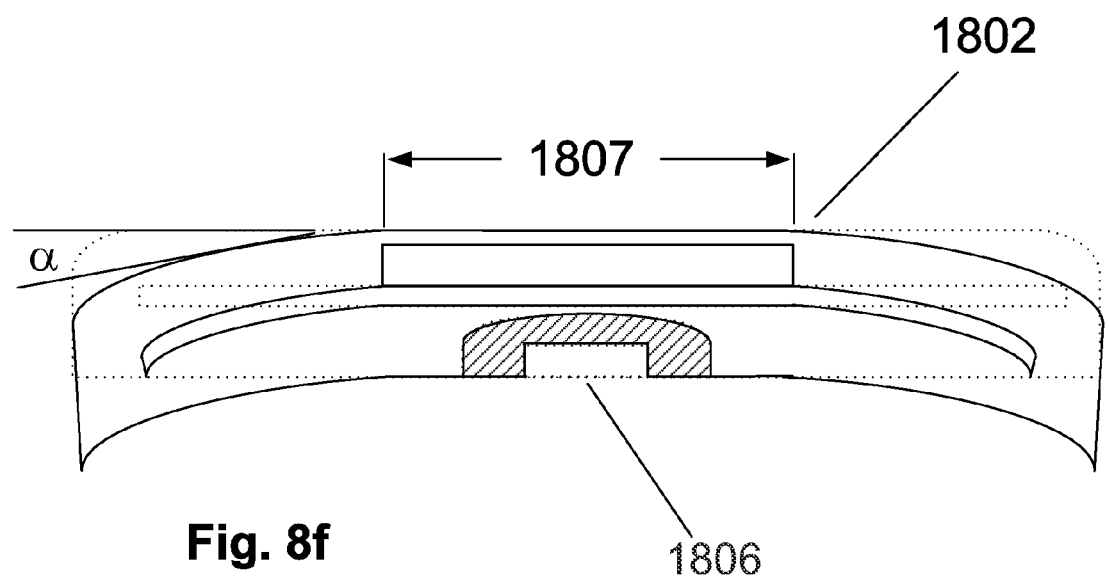

It is not necessary for flexible electronics housing 1802 to maintain contact with carrier 1201 in portions away from electrical connectors 1805 and exposed electrical contact portions 1108. For example, if carrier 1201 is contoured to a body of a subject, and bends away from flexible electronics housing 1802, electrical communication may be maintained through rigid portion 1807, as illustrated, for example, in FIG. 8e. In some embodiments, each end of flexible housing 1802 may be configured to flex as much as sixty degrees away from a flat plane. In embodiments that include rigid portion 1807, bending may begin at a portion immediately outside of rigid portion 1807. FIG. 8f illustrates a flexible housing 1802 including a rigid portion 1807 with flexed ends bent at an angle $\alpha$.

Flexible housing 1802 may be constructed of any suitable flexible material, such as, for example, silicone, PMMA, PEEK, polypropylene, and polystyrene. Flexible housing 1802 may be constructed from a top portion and a bottom portion, with the components being placed inside prior to sealing the top portion to the bottom portion. Flexible housing 1802 may also be constructed through overmolding techniques, wherein a flexible material is molded over and around the required interior components. Flexible housing 1802 may be manufactured with additives, for example to include particulate substances to provide color or ferrite substances, which may reflect and/or absorb a radiofrequency signal produced by a primary antenna contained within flexible housing 1802. A ferrite additive 1843 in flexible housing 1802 may increase the efficiency of the primary antenna and/or may reduce excess external transmissions by reflecting and/or absorbing the radiofrequency signal.

In some embodiments consistent with the present disclosure, electrical communication between carrier 1201 and an electronics housing may be made through electrical contacts 1810 located on a protruding non-pouch connector 1811, as illustrated in FIG. 8d. Electrical contacts 1810 may be disposed circumferentially on non-pouch connector 1811 and located at different heights. In such an embodiment, a connection portion of the electronics housing may be configured to receive electrical contacts configured in this fashion.

In many of the examples described above, external unit 120 includes an electronics housing and an adhesive carrier to which the housing may be releasably connected. The examples provided are intended to be exemplary only, and are not intended to limit the placement or location of any of the components described. Additional embodiments including the location of various components on either the housing or the carrier may be realized without departing from the scope of the invention. For example, in some embodiments, some or all of the required circuit component may be printed on the carrier. In some embodiments, the primary antenna may be contained within the housing. In some embodiments, a flexible battery, such as a paper battery, may be included on the carrier to replace or supplement a battery contained in the housing.

In some embodiments, external control unit 120 may be configured for remote monitoring and control. In such an embodiment, electronics housing 1202 may include, in addition to any or all of the elements discussed above, a communications interface 145, and memory unit 143. Communications interface 145 may include a transceiver, configured for both transmitting and receiving, a transmitter-receiver, a transmitter alone, and a receiver alone. Processor 144 may be configured to utilize communications interface 145 to communicate with a location remote from the control unit to transmit and/or receive information which may be retrieved from and/or stored in memory unit 143.

Processor 144 may be configured to cause application of a control signal to primary antenna 150. Processor 144 may further be configured to monitor a feedback signal indicative of a subject's breathing. Such a feedback signal may include a coupled feedback signal developed on the primary antenna 150 through wireless interaction with the secondary antenna 152. Further details regarding the coupled feedback signal are provided below. Processor 144 may then store information associated with or about both the control signal and the coupled feedback signal in the memory, and may utilize the communications interface 145 to transmit the stored information to a remote location. Processor 144 may also store information about the external unit, for example, information about battery depletion and energy expenditure. Processor 144 may also be configured to transmit collected information about the control signal, the feedback signal, and/or the external unit without first putting the information into storage. In such an embodiment, processor 144 may cause transmission of collected information via the communications interface 145 as that information is received. Thus, in some embodiments, external unit 120 may not require a memory.

In some embodiments, processor 144 may be configured to monitor a feedback signal provided by alternative means, such as electromyography electrodes, thermistors, accelerometers, microphones, piezoelectric sensors, etc., as previously described. Each of these means may provide a feedback signal that may be indicative of a subject's breathing. A thermistor, for example, may provide a signal that relates to a temperature of a subject's expired air, inspired air, or a subject's skin, which may be indicative of breathing. Electromyography electrodes may provide a feedback signal indicative of breathing based on the detection of muscle contractions. An accelerometer may provide a signal indicative of breathing by measuring a speed or rate at which parts of the subject's body, such as a chest or chin, moves. Microphones may be used to provide feedback signals, for example, by detecting acoustic variations coincident with a breathing pattern. Finally, piezoelectric sensors, for example, may be used to measure muscle movement.

The information associated with or about the control signal and the feedback signal may include information about a patient's therapy. Information about the control signal may include a complete history and/or any portion thereof of control signal transmissions caused by the processor. Information about the feedback signal may include a complete history and/or any portion thereof of feedback signals measured, such as a history of coupled feedback signals developed on primary antenna 150. Information associated with the feedback signal may include information about a usage period of the control unit, energy expenditure of the control unit, tongue movement, sleep disordered breathing occurrence, e.g. the occurrence of sleep apnea, hypopnea, and/or snoring, battery depletion of the control unit, and information about tongue movement in response to the modulation signal. Together, the collected information may represent a complete history of a patient's therapy session. The control signal information and feedback signal information may be stored in a synchronized fashion, to ensure that subsequent data processing can determine which portions of each signal occurred at the same time. A few examples of information that may be contained in control signal and feedback signal information are described below. As noted above, however, the memory may store complete information about control signal transmissions and feedback signals. Thus, the storage and/or transmission of any portion of these signals or any data describing them is also contemplated.

In some embodiments, information about the control signal may include summarizing information, for example a number of times or frequency with which the control signal was utilized to induce nerve modulation. Information about the control signal may include strength, duration, and other descriptive parameters of the control signal, at both modulation and sub-modulation levels. The information transmitted and received during communication with the remote location may include information about a coupled feedback signal. Information about the feedback signal may include information indicative of a patient's tongue movement or motion and information indicative of a frequency or duration of sleep disordered breathing events. In some embodiments, the stored information may be information that combines control signal information and feedback signal information, for example, information that describes a patient response to nerve modulation signals.

The stored information may be transmitted to a location remote from control unit 120 via a communications interface 145. Communications interface 145 may include a transceiver configured to send and receive information. The transceiver may utilize various transmission methods known in the art, for example wi-fi, Bluetooth, radio, RFID, smart chip or other near field communication device, and any other method capable of wirelessly transmitting information. Communications interface 145 or transceiver may also be configured to transmit the stored information through a wired electrical connection. The transmitted information may be received by a remote location. A remote location suitable for receipt of the transmitted information may function as a relay station, or may be a final destination. A final destination, for example, may include a centralized server location. External unit 120 may transmit the stored information to a relay station device which may then transmit the information to another relay station device or final destination. For example, a relay station device may include a patient's mobile device, smartphone, home computer, and/or a dedicated relay unit. A dedicated relay unit may include an antenna situated beneath a patient's pillow, for example to permit the transmission of a signal across a signal in circumstances where communications interface 145 may not be powerful enough or large enough to transmit a signal more than a few inches or feet. In some embodiments, a dedicated relay unit may also include a medical device console, described in greater detail below with respect to FIG. 9, configured to receive information transmitted by communications interface 145. The relay station device may receive the transmitted information and may store it prior to transmitting it, via, for example, any known communication technique, to a final destination. For example, the relay station may receive information from the external unit on a nightly basis, but only establish a connection with a final destination on a weekly basis. The relay station may also perform analysis on the received information prior to establishing a connection with a final destination. In some embodiments, a relay station device may relay received information immediately as it is received, or as soon as connection with the final destination can be established.

In some embodiments, external control unit 120 may be programmable and reprogrammable. For example, as described above, a memory included with external control unit 120 may store information associated with or about the control signal and the coupled feedback signal and may include information about therapy a patient has undergone. Further, a memory included with an external control unit 120 may be a programmable and/or reprogrammable memory configured to store information associated with at least one characteristic of sleep disordered breathing exhibited by a subject. Processor 144 may utilize the information associated with at least one characteristic of sleep disordered breathing to generate a hypoglossal nerve modulation control signal based on the information. That is, processor 144 may determine modulation parameters based on information about a patient's sleep disordered breathing characteristics. In some embodiments, such information may be determined by physicians, for example through the use of sleep lab equipment such as EKGs, EEGs, EMGs, breathing monitors, blood oxygen monitors, temperature monitors, brain activity monitors, cameras, accelerometers, electromyography equipment, and any other equipment useful for monitoring the sleep of a patient, and programmed into the memory. In some embodiments, such information may be determined by processor 144 by monitoring of the control signal and the coupled feedback signal.

As described above, external control unit 120 may include components that permit the recording, storage, reception, and transmission of information about a patient's sleep breathing patterns, about any therapy administered to the patient during sleep, and about the response of a patient's sleep breathing patterns to administered therapy. Such information may be stored for later transmission, may be transmitted as it is received or shortly thereafter, may be received and stored for later use, and/or may be utilized by processor 144 as it is received or shortly thereafter. This information may be generated by processor 144 through monitoring of a control signal transmitted to an implant unit 110 and a coupled feedback signal received therefrom and/or through other means described herein for processor 144 to collect feedback, such as electromyography electrodes, piezoelectric sensors, audio sensors, thermistors, and accelerometers.

This information may also be generated through various equipment at the disposal of physicians in, for example, a sleep lab. This stored information may be utilized, for example by processor 144 or by software running on a standard computer, to determine parameters of a hypoglossal nerve modulation control signal specific to a certain patient, based on the collected information. In an embodiment where parameters are determined by outside of external control unit 120, such parameters may be received by communications interface 145 of external control unit 120 as described above. Some examples describing the use of these capabilities is included below.

In an embodiment for determining initial modulation parameters for a patient, the above described system may operate as follows. After undergoing a surgical procedure to receive an implant unit 110, a patient may visit a sleep lab to determine initial modulation control signal parameters, such as pulse frequency, amplitude, train length, etc. Modulation control signal parameters may include pulse train parameters, described in greater detail below with respect to FIG. 17. A physician may use an endoscope to inspect an awake patient's airway during hypoglossal nerve modulation to determine that implant unit 110 is able to effectively cause airway dilation. Then, the patient may go to sleep in the sleep lab while being monitored by the physician. The patient's sleep may be monitored through a variety of tools available in a sleep lab, such as EKGs, EEGs, EMGs, breathing monitors, blood oxygen monitors, temperature monitors, brain activity monitors, cameras, electromyography electrodes, and any other equipment useful for monitoring the sleep of a patient. The monitoring equipment may be used to determine a patient's quality of sleep and to determine the onset of sleep disordered breathing. The physician may also monitor the patient's sleep through the use of external unit 120. Through a wireless or wired communication set up through communications interface 145 with processor 144, the physician may also monitor information gathered by external unit 120, e.g. modulation and sub-modulation control signals, feedback signals, battery levels, etc. Through communications interface 145, the physician may also control the modulation and sub-modulation signals generated by processor 144.

Thus, a physician may, through information gathered by sleep lab equipment and external unit 120, monitor a patient's sleep breathing patterns, including instances of sleep disordered breathing, and, in response to the monitored information, update the programming of processor 144 to optimize the therapy delivered to the patient in order to reduce instances of sleep disordered breathing. That is, processor 144 may be programmed to use a control signal that is tailored to cause optimum modulation, based on any or all of the information collected. In embodiments involving the application of a continuous modulation pulse train, such optimization may include selecting parameters, such as the frequency, amplitude, and duration of modulation pulses. For example, a physician observing a high frequency of sleep disordered breathing occurrences may adjust the parameters of a modulation pulse train until the sleep disordered breathing occurrences are reduced in number or stop altogether. The physician, thus, may be able to program processor 144 to effectively modulate the hypoglossal nerve to stop or minimize sleep disordered breathing without stimulating any more than necessary.

In some embodiments, the modulation pulse train may not be programmed with constant parameter values, but may be programmed to change during the course of an evening, or therapy period. Constant modulation signals, whether they are constant in amplitude, duration, and/or frequency of modulation pulses may result in diminishing sensitivity or response to modulation signals over time. For example, muscular contractions in response to a constant modulation signal may be reduced over time. Over the course of a therapy period, the muscular contractions resulting from a steady pulse train may be diminished, which may, in turn, cause an increase in sleep disordered breathing events. In order to counteract this effect, a pulse train may be dynamically modified during a therapy period via a plurality of predetermined alterations to the pulse train of a modulation control signal. For example, processor 144 may be programmed to alter at least one characteristic of the modulation pulse train, e.g., to increase, decrease, or otherwise alter the amplitude, duration and/or frequency of modulation pulses over the course of a therapy period. Any and all characteristics of a pulse train of a modulation control signal may be altered over the course of therapy period to increase modulation efficacy. As described above, physician monitored therapy periods may be utilized to determine an optimal pattern of alterations to the modulation control signal.

In embodiments involving selective modulation based on the detection of sleep disordered breathing precursors, such optimization may include selecting not only modulation parameters, which may be selected so as to vary with time over the course of a therapy period, but also feedback parameters and thresholds consistent with a sleep disordered breathing determination. For example, a physician may compare indications of tongue movement collected by external unit 120 with extrinsic indicators of sleep disordered breathing from sleep lab equipment. The physician may then correlate observed sleep disordered breathing patterns with detect tongue movement patterns, and program processor 144 to generate a modulation control signal when those tongue movement patterns are detected.

In some embodiments, the actions of the physician as described above may be performed by on a computer running software dedicated to the task. A computer system may be programmed to monitor the sleep breathing patterns of a patient and to program, reprogram, and/or update the programming of processor 144 accordingly.

The present disclosure contemplates several additional embodiments for the updating of modulation parameters. In one embodiment, a patient, utilizing the sleep disordered breathing therapy system at home, may have their equipment updated based on nightly data collection. As described above, communications interface 145 of external unit 120 may transmit information either to a relay station or directly to a final destination on a regular basis, monthly, weekly, daily, and even hourly or constantly. In some embodiments, the communications interface 145 of external unit 120 may be configured to transmit information based on certain thresholds, for example, if a number of sleep disordered breathing occurrences exceeds a predetermined number. At the final destination, which may be a remote location, e.g. a physician's office, or console device in the patient's home, the collected information may be analyzed in any of the ways described above and used to determine new modulation parameters, to be transmitted, via the communications interface 145, back to the patient's external unit 120. Thus, the patient's sleep may be monitored on a regular basis, either through automated software or with the aid of a physician, and the patient's therapy may be updated accordingly.

In some embodiments, the information may be transferred to a relay station device or to a final destination when the patient places external unit 120 in a charging device.

Figure 9:
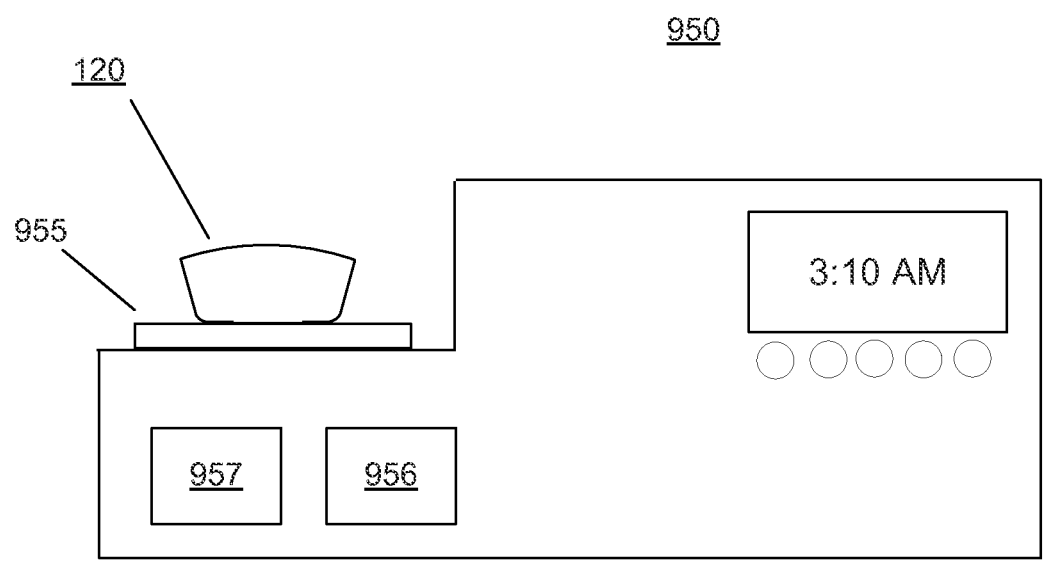
FIG. 9 illustrates a medical device console unit of an exemplary embodiment of the present disclosure.

For example, a medical console device, illustrated in FIG. 9, may be provided with an electrical interface 955 configured to receive therapy information from a patient's external unit 120. Medical console device 950 may further include a data storage unit 956 for storing the therapy information and at least one processing device 957 for analyzing the therapy information and determining updated control parameters for external unit 120. Medical console device 950 may transmit updated control parameters to communications interface 145 of external unit 120 via electrical interface 955. Such communication may be wired, or may be wireless transmission through any known means, such as wi-fi, bluetooth, RFID, etc. The information may then be processed by the console, or transmitted to a final destination for processing. Transmission to a final destination may be accomplished, for example, via the internet, wireless connection, cellular connection, or any other suitable transmission means. The information may be used to determine updated modulation parameters for processor 144, either by the medical console device 950 or by a different final destination. In some embodiments, external unit 120 may be disposable. In such embodiments, processor 144 may be programmed with a patient's particular therapy regime through connection, wireless or wired, to the medical console device 950 prior to therapy. In some embodiments, a medical console device may be configured to transmit modulation parameters to several disposable external units 120 at the same time. In some embodiments, external unit 120 may be recharged via electrical interface 955, in either a wired or wireless fashion. In some embodiments, medical console device 950 may be configured for bedside use, and may include, for example, all of the functions of a standard alarm clock/radio.

In some embodiments, information collected and transmitted by external control unit 120 may be used to monitor patient compliance. For example, by monitoring information such as battery depletion, modulation frequency, and any other parameter discussed herein, a physician may be able to determine whether or not a patient is complying with a therapy regime. Physicians may use this information to follow up with patient's and alter therapy regimes if necessary. In some embodiments, information collected and transmitted by external control unit 120 may be used to monitor system efficacy. For example, it may be difficult for a patient to determine how successful therapy is, as they sleep during therapy periods. The equipment and components described herein may be used to provide information to a patient and/or their physician about the effectiveness of treatment. Such information may also be used to determine effectiveness of the implant unit 110 specifically. For example, if levels of nightly battery depletion increase without a corresponding increase in the frequency of modulation, it may be indicative of a problem with implant unit 110 or its implantation.

Figure 10:
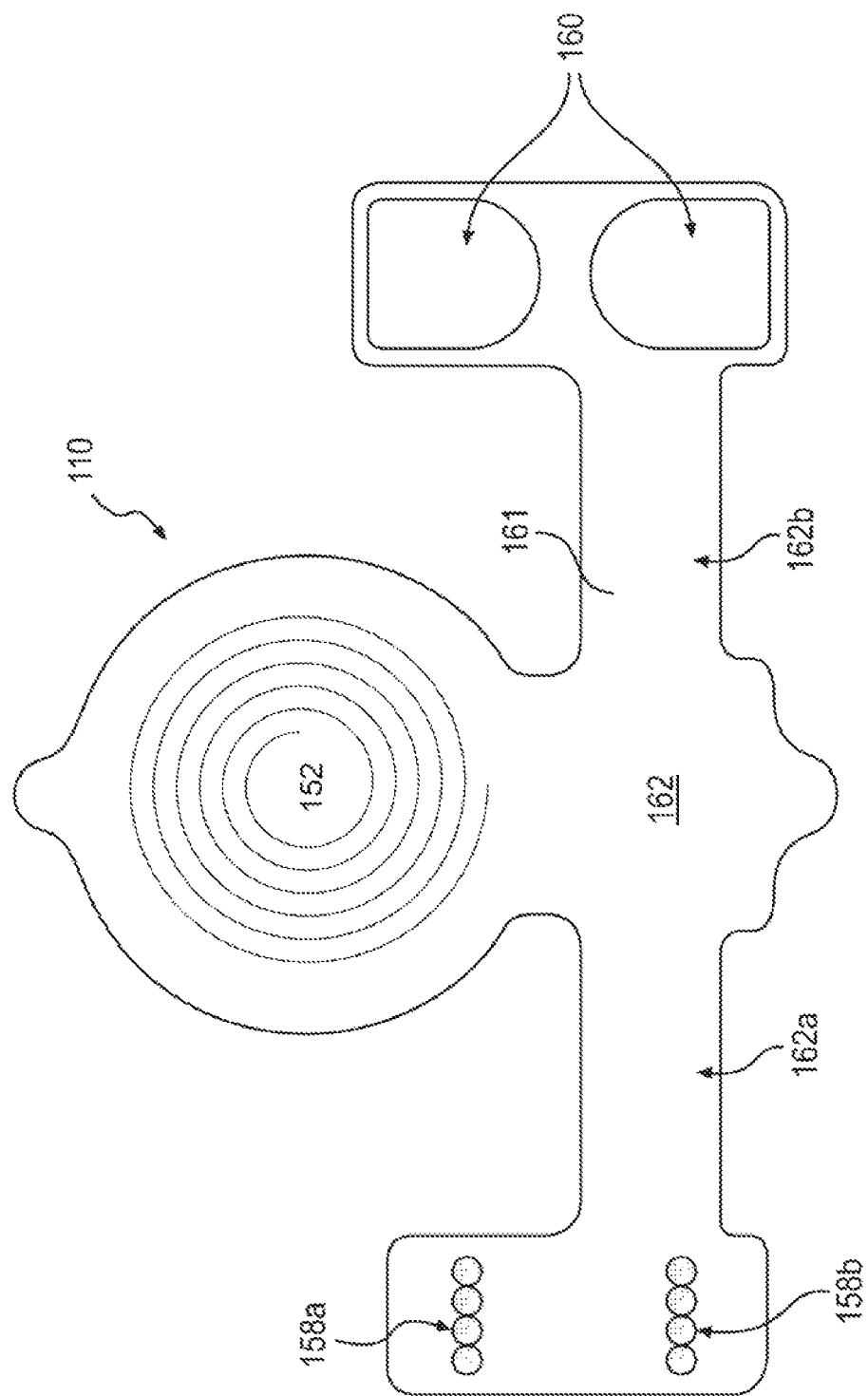
FIG. 10 is a top view of an implant unit, according to an exemplary embodiment of the present disclosure.

Implant unit 110 may additionally include a plurality of field-generating implant electrodes 158a, 158b. The electrodes may include any suitable shape and/or orientation on the implant unit so long as the electrodes may be configured to generate an electric field in the body of a patient. Implant electrodes 158a and 158b may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, circular electrodes, and/or circular pairs of electrodes. As shown in FIG. 10, electrodes 158a and 158b may be located on an end of a first extension 162a of an elongate arm 162. The electrodes, however, may be located on any portion of implant unit 110. Additionally, implant unit 110 may include electrodes located at a plurality of locations, for example on an end of both a first extension 162a and a second extension 162b of elongate arm 162, as illustrated, for example, in FIG. 11a. Positioning electrodes on two extensions of elongate arm 162 may permit bilateral hypoglossal nerve stimulation, as discussed further below. Implant electrodes may have a thickness between about 200 nanometers and 1 millimeter. Anode and cathode electrode pairs may be spaced apart by about a distance of about 0.2 mm to 25 mm. In additional embodiments, anode and cathode electrode pairs may be spaced apart by a distance of about 1 mm to 10 mm, or between 4 mm and 7 mm. Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm and 1 mm.

FIG. 10 provides a schematic representation of an exemplary configuration of implant unit 110. As illustrated in FIG. 10, in one embodiment, the field-generating electrodes 158a and 158b may include two sets of four circular electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include, for example, elongated arms, suture holes, polymeric surgical mesh, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body. For example, in some embodiments, implant unit 110 may include an elongate arm 162 having a first extension 162a and, optionally, a second extension 162b. Extensions 162a and 162b may aid in orienting implant unit 110 with respect to a particular muscle (e.g., the genioglossus muscle), a nerve within a patient's body, or a surface within a body above a nerve. For example, first and second extensions 162a, 162b may be configured to enable the implant unit to conform at least partially around soft or hard tissue (e.g., nerve, bone, or muscle, etc.) beneath a patient's skin. Further, implant unit 110 may also include one or more suture holes 160 located anywhere on flexible carrier 161. For example, in some embodiments, suture holes 160 may be placed on second extension 162b of elongate arm 162 and/or on first extension 162a of elongate arm 162. Implant unit 110 may be constructed in various shapes. Additionally, or alternatively, implant unit 110 may include surgical mesh 1050 or other perforatable material, described in greater detail below with respect to FIG. 12. In some embodiments, implant unit may appear substantially as illustrated in FIG. 10. In other embodiments, implant unit 110 may lack illustrated structures such as second extension 162b, or may have additional or different structures in different orientations. Additionally, implant unit 110 may be formed with a generally triangular, circular, or rectangular shape, as an alternative to the winged shape shown in FIG. 10. In some embodiments, the shape of implant unit 110 (e.g., as shown in FIG. 10) may facilitate orientation of implant unit 110 with respect to a particular nerve to be modulated. Thus, other regular or irregular shapes may be adopted in order to facilitate implantation in differing parts of the body.

As illustrated in FIG. 10, secondary antenna 152 and electrodes 158a, 158b may be mounted on or integrated with flexible carrier 161. Various circuit components and connecting wires may be used to connect secondary antenna with implant electrodes 158a and 158b. To protect the antenna, electrodes, and implantable circuit components from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include a plurality of layers, including different materials or combinations of materials in different layers.

In some embodiments of the present disclosure, the encapsulation structure of implanted unit may include two layers. For example, a first layer may be disposed over at least a portion of the implantable circuit arranged on the substrate, and a second layer may be disposed over the first layer. In some embodiments, the first layer may be disposed directly over the implantable circuit, but in other embodiments, the first layer may be disposed over an intervening material between the first layer and the implantable circuit. In some embodiments, the first layer may provide a moisture barrier and the second layer may provide a mechanical protection (e.g., at least some protection from physical damage that may be caused by scratching, impacts, bending, etc.) for the implant unit. The terms "encapsulation" and "encapsulate" as used herein may refer to complete or partial covering of a component. In some embodiments component may refer to a substrate, implantable circuit, antenna, electrodes, any parts thereof, etc. The term "layer" as used herein may refer to a thickness of material covering a surface or forming an overlying part or segment. The layer thickness can be different from layer to layer and may depend on the covering material and the method of forming the layer. For example, a layer disposed by chemical vapor may be thinner than a layer disposed through other methods.

Other configurations may also be employed. For example, another moisture barrier may be formed over the outer mechanical protection layer. In such embodiments, a first moisture barrier layer (e.g., parylene) may be disposed over (e.g., directly over or with intervening layers) the implantable circuit, a mechanical protection layer (e.g., silicone) may be formed over the first moisture barrier, and second moisture barrier (e.g., parylene) may be disposed over the mechanical protection layer.

Figure 11A:
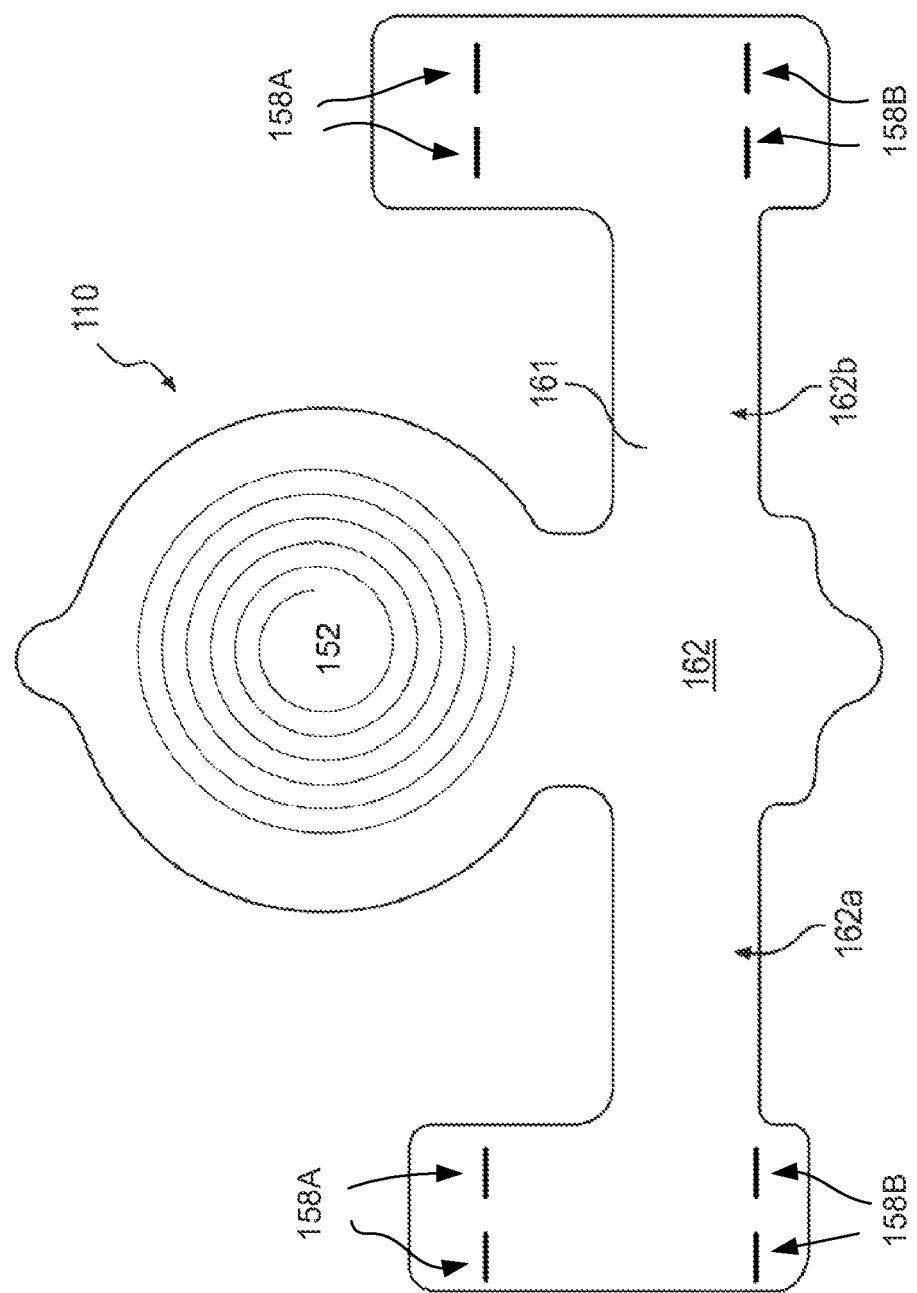
FIGS. 11a-b are top views of alternate embodiments of implant unit, according to an exemplary embodiment of the present disclosure.

FIG. 11a is a perspective view of an alternate embodiment of an implant unit 110, according to an exemplary embodiment of the present disclosure. As illustrated in FIG. 11a, implant unit 110 may include a plurality of electrodes, located, for example, at the ends of first extension 162a and second extension 162b. FIG. 11a illustrates an embodiment wherein implant electrodes 158a and 158b include short line electrodes.

Figure 11B:
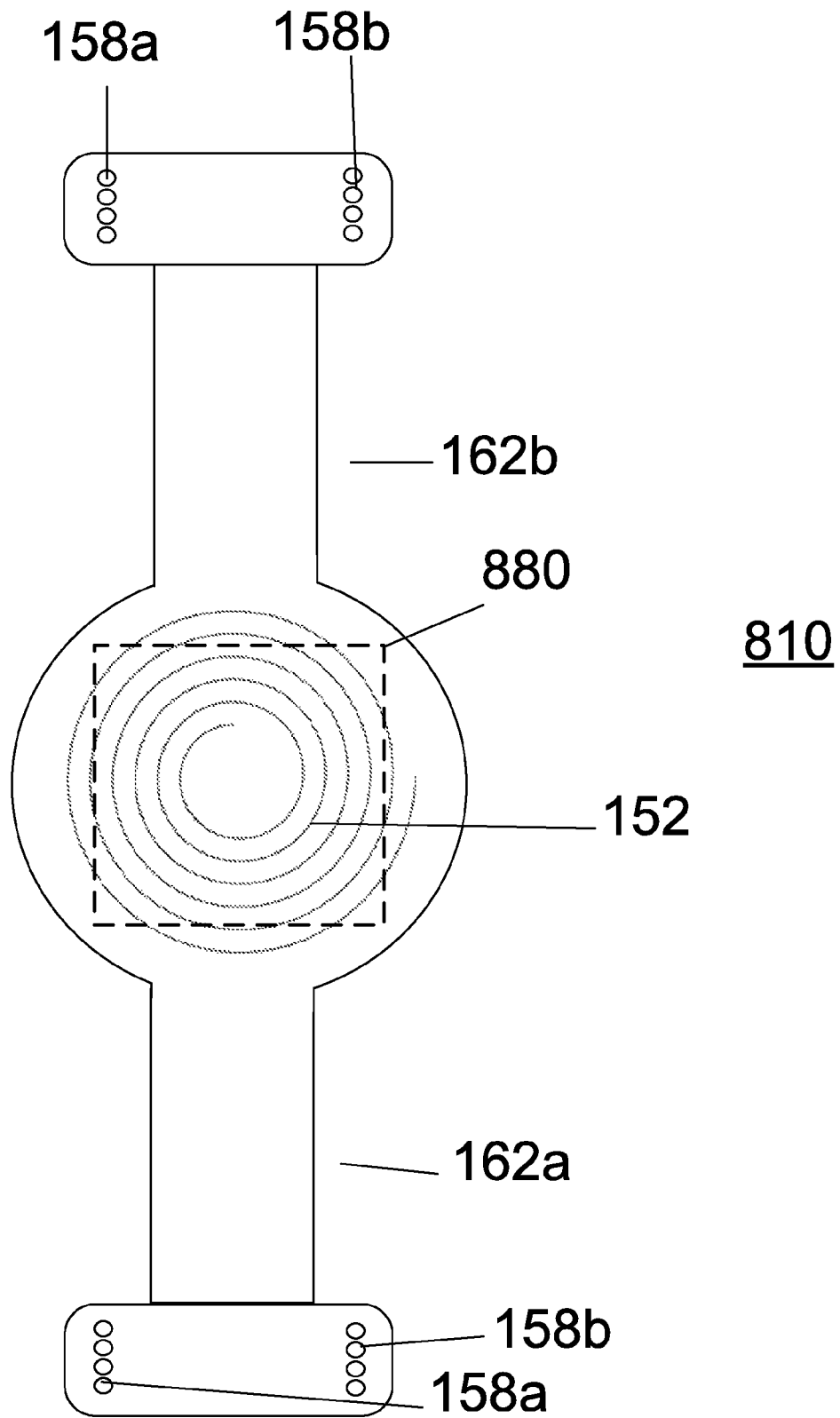

FIG. 11b illustrates another alternate embodiment of implant unit 810, according to an exemplary embodiment of the present disclosure. Implant unit 810 is configured such that circuitry 880 is located in a vertical arrangement with secondary antenna 852. Implant unit 810 may include first extension 162a and second extension 162b, wherein one or both of the extensions accommodate electrodes 158a and 158b.

Figure 12:
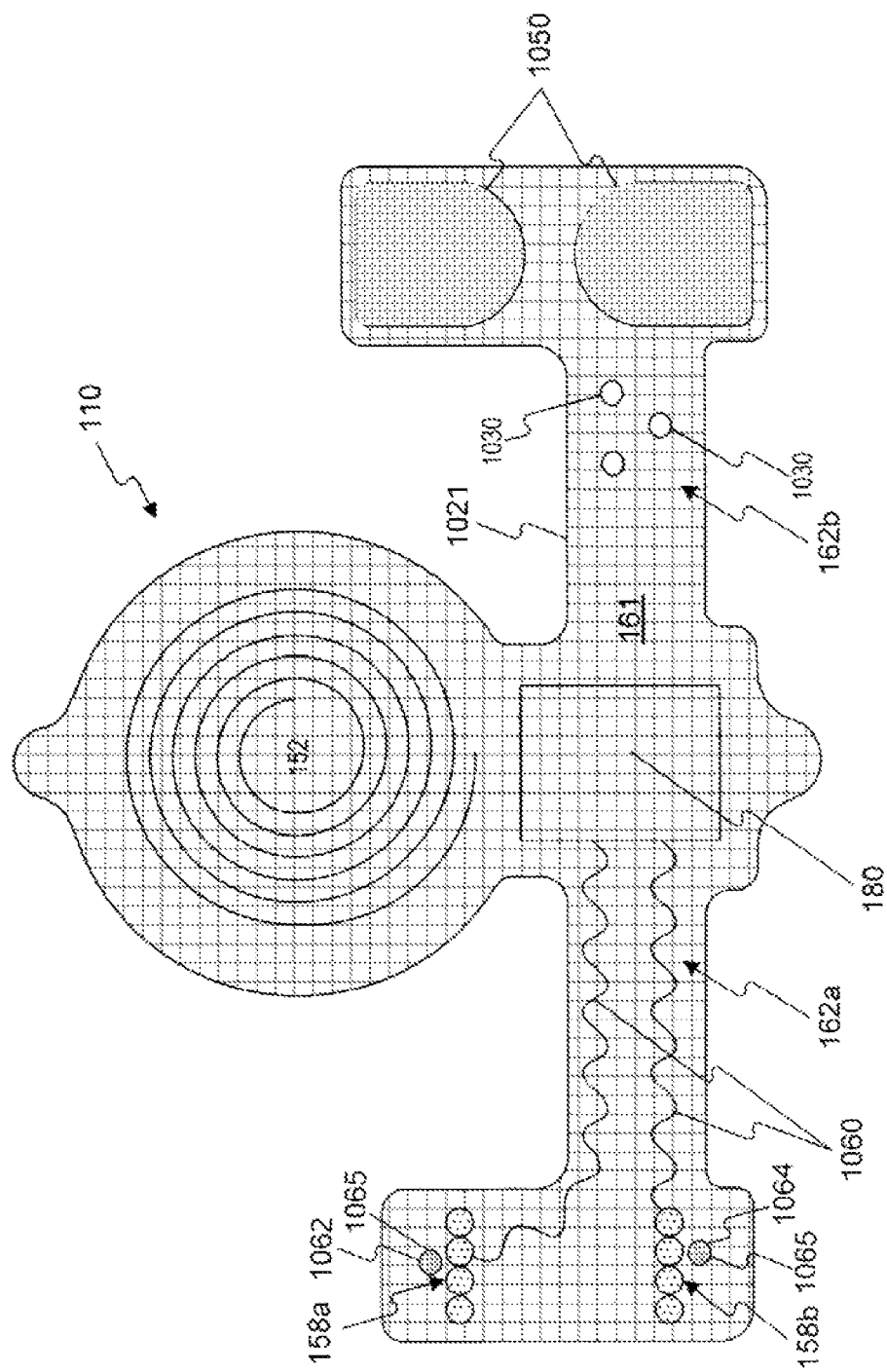
FIG. 12 illustrates additional features of an exemplary embodiment of an implant unit according to the present disclosure

FIG. 12 illustrates another exemplary embodiment of encapsulated implant unit 110. Exemplary embodiments may incorporate some or all of the features illustrated in FIG. 10 as well as additional features. A protective coating of implant unit 110 may include a primary capsule 1021. Primary capsule 1021 may encapsulate the implant unit 110 and may provide mechanical protection for the implant unit 110. For example, the components of implant unit 110 may be delicate, and the need to handle the implant unit 110 prior to implantation may require additional protection for the components of implant unit 110, and primary capsule 1021 may provide such protection. Primary capsule 1021 may encapsulate all or some of the components of implant unit 110. For example, primary capsule 1021 may encapsulate antenna 152, flexible carrier 161, and implantable circuit 180. The primary capsule may leave part or all of electrodes 158a, 158b exposed enabling them to deliver energy for modulating a nerve unimpeded by material of the primary capsule. In alternative embodiments, different combinations of components may be encapsulated or exposed.

Primary capsule 1021 may be fashioned of a material and thickness such that implant unit 110 remains flexible after encapsulation. Primary capsule 1021 may include any suitable bio-compatible material, such as silicone, or polyimides, phenyltrimethoxysilane (PTMS), polymethyl methacrylate (PMMA), Parylene C, liquid polyimide, laminated polyimide, polyimide, Kapton, black epoxy, polyether ketone (PEEK), Liquid Crystal Polymer (LCP), or any other suitable biocompatible coating.

Figure 13A:
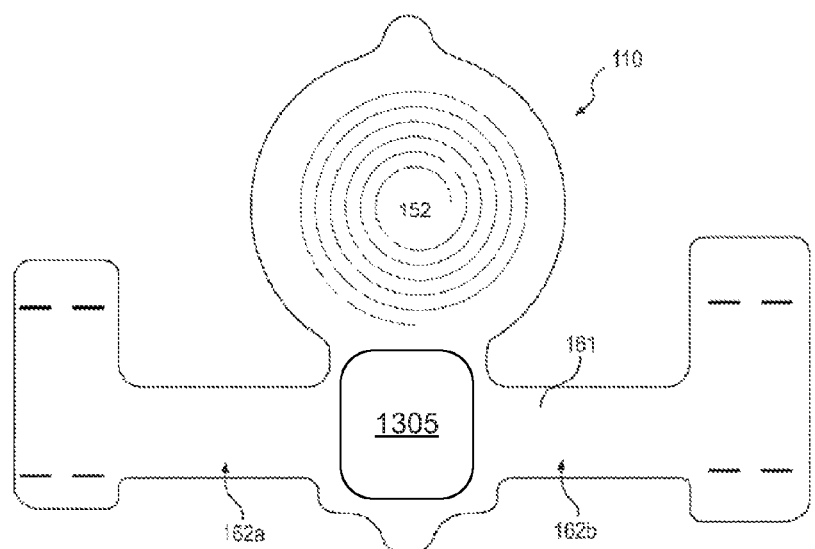
FIGS. 13a-13b illustrates a ceramic implant housing of an exemplary embodiment of the present disclosure.
Figure 13B:
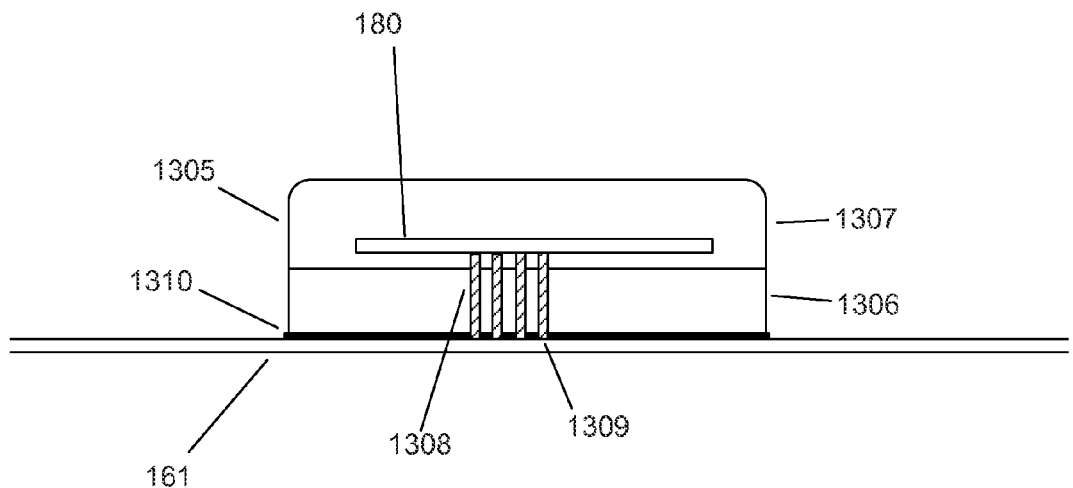

In some embodiments, all or some of the circuitry components included in implant 110 may be housed in a rigid housing, as illustrated in FIGS. 13a-b. Rigid housing 1305 may provide the components of implant 110 with additional mechanical and environmental protections. A rigid housing may protect the components of implant 110 from physical trauma during implantation or from physical trauma caused by the tissue movement at an implantation site. Rigid housing may also provide additional environmental protections from the corrosive environment within the body. Furthermore, the use of a rigid housing may simplify a process for manufacturing implant unit 110.

FIGS. 13a-b illustrates an embodiment including an implant unit 110 with a rigid housing. As shown in FIGS. 13a-b, implant unit 110 may include all of the components of implant unit 110, e.g. modulation electrodes 158a, 158b, secondary antenna 152, flexible carrier 161, extension arms 162a, 162b, as well as circuitry 180 and any other component described herein. Some, or all, of these components, e.g. circuitry 180, may be included inside rigid housing 1305.

Rigid housing 130 may be constructed, for example, of ceramic, glass, and/or titanium, and may include a ceramic clamshell. Rigid housing 130 may, for example be welded closed with a biocompatible metal such as gold or titanium, or closed with any other suitable methods. Such a housing may also include a ceramic bottom portion 1306 and a titanium or ceramic upper portion 1307. Rigid housing 1305 may include one or more conductive feedthroughs 1308 to make contact with circuitry on flexible carrier 161. Inside the housing, conductive feedthroughs 1308 may be soldered, welded, or glued to circuitry 180, or any other internal component, through traditional soldering techniques. Conductive feedthroughs 1308 may comprise gold, platinum, or any other suitable conductive material. In one embodiment, rigid housing 1305 may include four feedthroughs 1308 comprising positive and negative connections for the modulation electrodes 158a, 158b, and the secondary antenna 152. Of course, any suitable number of feedthroughs 1308 may be provided.

Rigid housing 1308 may be mounted to flexible carrier 161 through controlled collapse chip connection, or C4 manufacturing. Using this technique, external portions 1309 of each conductive feedthrough 1308, which extend beyond the surface of rigid housing 1308, may be aligned with solder bumps on flexible carrier 161. Solder bumps may, in turn, connected to the electrical traces of flexible carrier 161. Once aligned, the solder is caused to reflow, creating an electrical connection between the electrical traces of flexible carrier 161 and the internal components of rigid housing 1305 via feedthroughs 1308. Once the electrical connection has been made, a non-conductive, or insulative, adhesive 1310 may be used to fill the gaps between the rigid housing and the flexible carrier in and around the soldered connections. The insulative adhesive 1310 may provide both mechanical protection to ensure that rigid housing 1305 does not separate from flexible carrier 161, as well as electrical protection to ensure that the feedthroughs 1308 do not short to each other.

Once mounted to flexible carrier 161, rigid housing 1305 and flexible carrier 161 may be encapsulated together via a multi-layer encapsulation structure described above.

Returning now to FIG. 12, also illustrated is encapsulated surgical mesh 1050. Surgical mesh 1050 may provide a larger target area for surgeons to use when suturing implant unit 110 into place during implantation. The entire surgical mesh 1050 may be encapsulated by primary capsule 1021, permitting a surgeon to pass a needle through any portion of the mesh without compromising the integrity of implant unit 110. Surgical mesh 1050 may additionally be used to cover suture holes 160, permitting larger suture holes 160 that may provide surgeons with a greater target area. Surgical mesh 1050 may also encourage surrounding tissue to bond with implant unit 110. In some embodiments, a surgeon may pass a surgical suture needle through suture holes 160, located on one extension 162a of an elongate arm 162 of implant unit 110, through tissue of the subject, and through surgical mesh 1050 provided on a second extension 162b of elongate arm 162 of implant unit 110. In this embodiment, the larger target area provided by surgical mesh 1050 may facilitate the suturing process because it may be more difficult to precisely locate a suture needle after passing it through tissue. Implantation and suturing procedures may be further facilitated through the use of a delivery tool, described in greater detail below.

Returning to FIGS. 2 and 3, external unit 120 may be configured to communicate with implant unit 110. For example, in some embodiments, a primary signal may be generated on primary antenna 150, using, e.g., processor 144, signal source 142, and amplifier 146. More specifically, in one embodiment, power source 140 may be configured to provide power to one or both of the processor 144 and the signal source 142. The processor 144 may be configured to cause signal source 142 to generate a signal (e.g., an RF energy signal). Signal source 142 may be configured to output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), a desired magnitude of electric field to be generated by implant electrodes 158a, 158b, etc. Amplifier 146 may output the amplified signal to primary antenna 150.

External unit 120 may communicate a primary signal on primary antenna to the secondary antenna 152 of implant unit 110. This communication may result from coupling between primary antenna 150 and secondary antenna 152. Such coupling of the primary antenna and the secondary antenna may include any interaction between the primary antenna and the secondary antenna that causes a signal on the secondary antenna in response to a signal applied to the primary antenna. In some embodiments, coupling between the primary and secondary antennas may include capacitive coupling, inductive coupling, radiofrequency coupling, etc. and any combinations thereof.

Coupling between primary antenna 150 and secondary antenna 152 may depend on the proximity of the primary antenna relative to the secondary antenna. That is, in some embodiments, an efficiency or degree of coupling between primary antenna 150 and secondary antenna 152 may depend on the proximity of the primary antenna to the secondary antenna. The proximity of the primary and secondary antennas may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of a primary signal on primary antenna 150 may cause or induce a secondary signal on secondary antenna 152, the coupling between the two antennas may also lead to a coupled signal or signal components on the primary antenna 150 as a result of the secondary signal present on secondary antenna 152. A signal on primary antenna 150 induced by a secondary signal on secondary antenna 152 may be referred to as a primary coupled signal component. The primary signal may refer to any and all signals or signal components present on primary antenna 150, regardless of source, and the primary coupled signal component may refer to any signal or signal component arising on the primary antenna as a result of coupling with signals present on secondary antenna 152. Thus, in some embodiments, the primary coupled signal component may contribute to the primary signal on primary antenna 150.

Implant unit 110 may be configured to respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158a and 158b.

FIG. 14 illustrates circuitry 170 that may be included in external unit 120 and circuitry 180 that may be included in implant unit 110. Additional, different, or fewer circuit components may be included in either or both of circuitry 170 and circuitry 180. As shown in FIG. 14, secondary antenna 152 may be arranged in electrical communication with implant electrodes 158a, 158b. In some embodiments, circuitry connecting secondary antenna 152 with implant electrodes 158a and 158b may cause a voltage potential across implant electrodes 158a and 158b in the presence of a secondary signal on secondary antenna 152. This voltage potential may be referred to as a field inducing signal, as this voltage potential may generate an electric field between implant electrodes 158a and 158b. More broadly, the field inducing signal may include any signal (e.g., voltage potential) applied to electrodes associated with the implant unit that may result in an electric field being generated between the electrodes.

The field inducing signal may be generated as a result of conditioning of the secondary signal by circuitry 180. As shown in FIG. 6, circuitry 170 of external unit 120 may be configured to generate an AC primary signal on primary antenna 150 that may cause an AC secondary signal on secondary antenna 152. In certain embodiments, however, it may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158a and 158b.

As noted above, the field inducing signal may be configured to generate an electric field between implant electrodes 158a and 158b. In some instances, the magnitude and/or duration of the generated electric field resulting from the field inducing signal may be sufficient to modulate one or more nerves in the vicinity of electrodes 158a and 158b. In such cases, the field inducing signal may be referred to as a modulation signal. In other instances, the magnitude and/or duration of the field inducing signal may generate an electric field that does not result in nerve modulation. In such cases, the field inducing signal may be referred to as a sub-modulation signal.

Various types of field inducing signals may constitute modulation signals. For example, in some embodiments, a modulation signal may include a moderate amplitude and moderate duration, while in other embodiments, a modulation signal may include a higher amplitude and a shorter duration. Various amplitudes and/or durations of field-inducing signals across electrodes 158a, 158b may result in modulation signals, and whether a field-inducing signal rises to the level of a modulation signal can depend on many factors (e.g., distance from a particular nerve to be stimulated; whether the nerve is branched; orientation of the induced electric field with respect to the nerve; type of tissue present between the electrodes and the nerve; etc.).

In some embodiments, the electrodes 158a and 158b may generate an electric field configured to penetrate intervening tissue 111 between the electrodes and one or more nerves. The intervening tissue 111 may include muscle tissue, bone, connective tissue, adipose tissue, organ tissue, or any combination thereof. For subjects suffering with obstructive sleep apnea, for instance, the intervening tissue may include the genioglossus muscle.

The generation of electric fields configured to penetrate intervening tissue is now discussed with respect to FIGS. 15a, 15b, 15c, and 16. In response to a field inducing signal, implant electrodes 158a and 158b may be configured to generate an electric field with field lines extending generally in the longitudinal direction of one or more nerves to be modulated. In some embodiments, implant electrodes 158a and 158b may be spaced apart from one another along the longitudinal direction of a nerve to facilitate generation of such an electric field. The electric field may also be configured to extend in a direction substantially parallel to a longitudinal direction of at least some portion of the nerve to be modulated. For example, a substantially parallel field may include field lines that extend more in a longitudinal direction than a transverse direction compared to the nerve. Orienting the electric field in this way may facilitate electrical current flow through a nerve or tissue, thereby increasing the likelihood of eliciting an action potential to induce modulation.

Figure 15A:
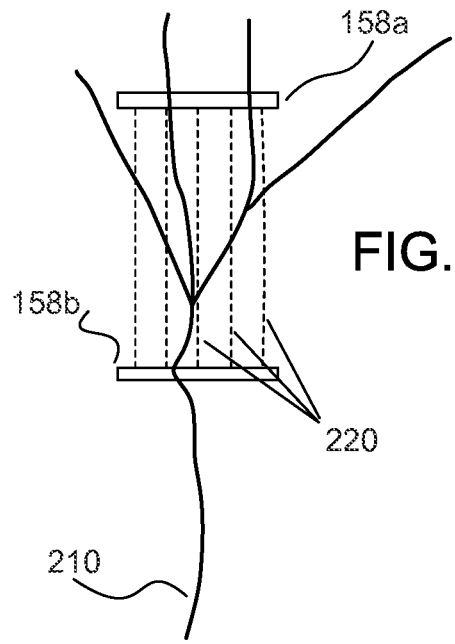
FIG. 15a illustrates a pair of electrodes spaced apart from one another along the longitudinal direction of nerve to facilitate generation of an electric field having field lines substantially parallel to the longitudinal direction of nerve.

FIG. 15a illustrates a pair of electrodes 158a, 158b spaced apart from one another along the longitudinal direction of nerve 210 to facilitate generation of an electric field having field lines 220 substantially parallel to the longitudinal direction of nerve 210. In FIG. 15a, modulation electrodes 158a, 158b are illustrated as line electrodes, although the generation of substantially parallel electric fields may be accomplished through the use of other types of electrodes, for example, a series of point electrodes. Utilizing an electric field having field lines 220 extending in a longitudinal direction of nerve 210 may serve to reduce the amount of energy required to achieve neural modulation.

Naturally functioning neurons function by transmitting action potentials along their length. Structurally, neurons include multiple ion channels along their length that serve to maintain a voltage potential gradient across a plasma membrane between the interior and exterior of the neuron. Ion channels operate by maintaining an appropriate balance between positively charged sodium ions on one side of the plasma membrane and negatively charged potassium ions on the other side of the plasma membrane. A sufficiently high voltage potential difference created near an ion channel may exceed a membrane threshold potential of the ion channel. The ion channel may then be induced to activate, pumping the sodium and potassium ions across the plasma membrane to switch places in the vicinity of the activated ion channel. This, in turn, further alters the potential difference in the vicinity of the ion channel, which may serve to activate a neighboring ion channel. The cascading activation of adjacent ion channels may serve to propagate an action potential along the length of the neuron. Further, the activation of an ion channel in an individual neuron may induce the activation of ion channels in neighboring neurons that, bundled together, form nerve tissue. The activation of a single ion channel in a single neuron, however, may not be sufficient to induce the cascading activation of neighboring ion channels necessary to permit the propagation of an action potential. Thus, the more ion channels in a locality that may be recruited by an initial potential difference, caused through natural means such as the action of nerve endings or through artificial means, such as the application of electric fields, the more likely the propagation of an action potential may be. The process of artificially inducing the propagation of action potentials along the length of a nerve may be referred to as stimulation, or up modulation.

Neurons may also be prevented from functioning naturally through constant or substantially constant application of a voltage potential difference. After activation, each ion channel experiences a refractory period, during which it "resets" the sodium and potassium concentrations across the plasma membrane back to an initial state. Resetting the sodium and potassium concentrations causes the membrane threshold potential to return to an initial state. Until the ion channel restores an appropriate concentration of sodium and potassium across the plasma membrane, the membrane threshold potential will remain elevated, thus requiring a higher voltage potential to cause activation of the ion channel. If the membrane threshold potential is maintained at a high enough level, action potentials propagated by neighboring ion channels may not create a large enough voltage potential difference to surpass the membrane threshold potential and activate the ion channel. Thus, by maintaining a sufficient voltage potential difference in the vicinity of a particular ion channel, that ion channel may serve to block further signal transmission. The membrane threshold potential may also be raised without eliciting an initial activation of the ion channel. If an ion channel (or a plurality of ion channels) are subjected to an elevated voltage potential difference that is not high enough to surpass the membrane threshold potential, it may serve to raise the membrane threshold potential over time, thus having a similar effect to an ion channel that has not been permitted to properly restore ion concentrations. Thus, an ion channel may be recruited as a block without actually causing an initial action potential to propagate. This method may be valuable, for example, in pain management, where the propagation of pain signals is undesired. As described above with respect to stimulation, the larger the number of ion channels in a locality that may be recruited to serve as blocks, the more likely the chance that an action potential propagating along the length of the nerve will be blocked by the recruited ion channels, rather than traveling through neighboring, unblocked channels.

The number of ion channels recruited by a voltage potential difference may be increased in at least two ways. First, more ion channels may be recruited by utilizing a larger voltage potential difference in a local area. Second, more ion channels may be recruited by expanding the area affected by the voltage potential difference.

Figure 15B:
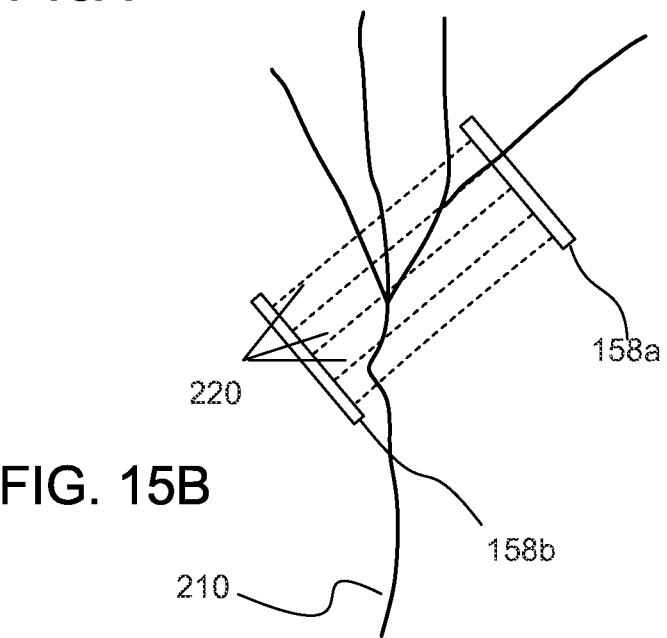
FIG. 15b illustrates an embodiment wherein electrodes are spaced apart from one another in a longitudinal direction of at least a portion of nerve.
Figure 15C:
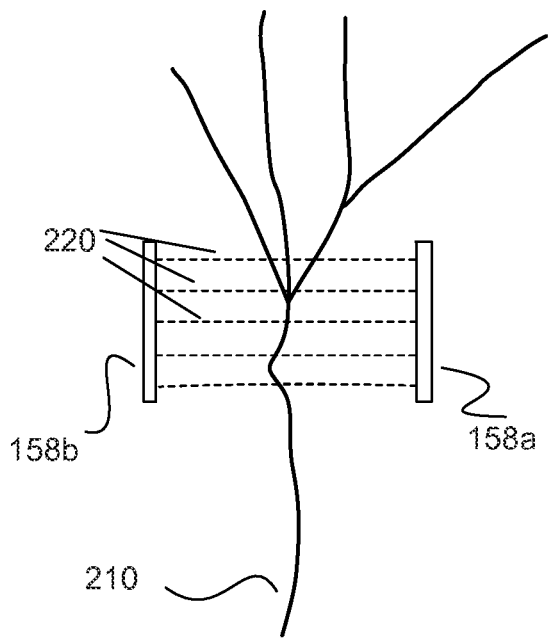
FIG. 15c illustrates a situation wherein electrodes are spaced apart from one another in a transverse direction of nerve.

Returning to FIG. 15a, it can be seen that, due to the electric field lines 220 running in a direction substantially parallel to the longitudinal direction of the nerve 210, a large portion of nerve 210 may encounter the field. Thus, more ion channels from the neurons that make up nerve 210 may be recruited without using a larger voltage potential difference. In this way, modulation of nerve 210 may be achieved with a lower current and less power usage. FIG. 15b illustrates an embodiment wherein electrodes 158a and 158 are still spaced apart from one another in a longitudinal direction of at least a portion of nerve 210. A significant portion of nerve 210 remains inside of the electric field. FIG. 15c illustrates a situation wherein electrodes 158a and 158b are spaced apart from one another in a transverse direction of nerve 210. In this illustration, it can be seen that a significantly smaller portion of nerve 210 will be affected by electric field lines 220.

Figure 16:
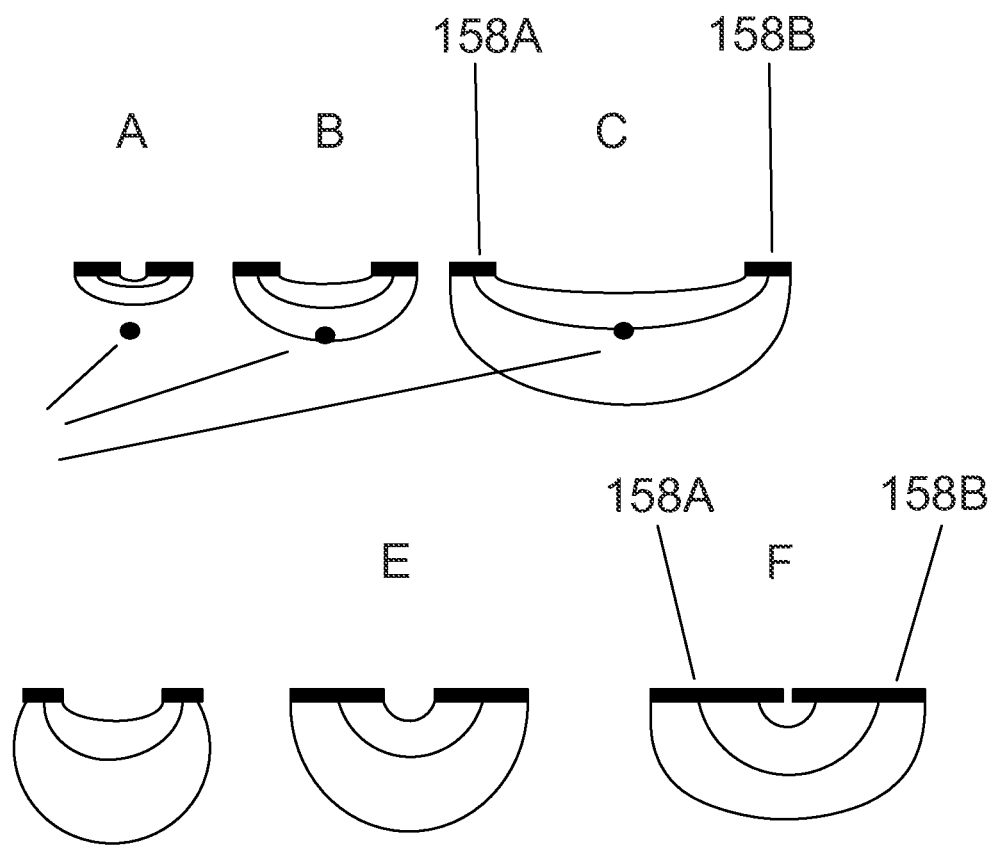
FIG. 16 illustrates effects of electrode configuration on the shape of a generated electric field.

FIG. 16 illustrates potential effects of electrode configuration on the shape of a generated electric field. The top row of electrode configurations, e.g. A, B, and C, illustrates the effects on the electric field shape when a distance between electrodes of a constant size is adjusted. The bottom row of electrode configurations, e.g. D, E, and F illustrates the effects on the electric field shape when the size of electrodes of constant distance is adjusted.

In embodiments consistent with the present disclosure, modulation electrodes 158a, 158b may be arranged on the surface of a muscle or other tissue, in order to modulate a nerve embedded within the muscle or other tissue. Thus, tissue may be interposed between modulation electrodes 158a, 158b and a nerve to be modulated. Modulation electrodes 158a, 158b may be spaced away from a nerve to be modulated. The structure and configuration of modulation electrodes 158a, 158b may play an important role in determining whether modulation of a nerve, which is spaced a certain distance away from the electrodes, may be achieved.

Electrode configurations A, B, and C show that when modulation electrodes 158a, 158b of a constant size are moved further apart, the depth of the electric field facilitated by the electrodes increases. The strength of the electric field for a given configuration may vary significantly depending on a location within the field. If a constant level of current is passed between modulation electrodes 158a and 158b, however, the larger field area of configuration C may exhibit a lower overall current density than the smaller field area of configuration A. A lower current density, in turn, implies a lower voltage potential difference between two points spaced equidistant from each other in the field facilitated by configuration C relative to that of the field facilitated by configuration A. Thus, while moving modulation electrodes 158a and 158b farther from each other increases the depth of the field, it also decreases the strength of the field. In order to modulate a nerve spaced away from modulation electrodes 158a, 158b, a distance between the electrodes may be selected in order to facilitate an electric field of strength sufficient to surpass a membrane threshold potential of the nerve (and thereby modulate it) at the depth of the nerve. If modulation electrodes 158a, 158b are too close together, the electric field may not extend deep enough into the tissue in order to modulate a nerve located therein. If modulation electrodes 158a, 158b are too far apart, the electric field may be too weak to modulate the nerve at the appropriate depth.

Appropriate distances between modulation electrodes 158a, 158b, may depend on an implant location and a nerve to be stimulated. For example, modulation point 901 is located at the same depth equidistant from the centers of modulation electrodes 158a, 158b in each of configurations A, B, and C. The figures illustrate that, in this example, configuration B is most likely to achieve the highest possible current density, and therefore voltage potential, at modulation point 901. The field of configuration A may not extend deeply enough, and the field of configuration C may be too weak at that depth.

In some embodiments, modulation electrodes 158a, 158b may be spaced apart by about a distance of about 0.2 mm to 25 mm. In additional embodiments, modulation electrodes 158a, 158b may be spaced apart by a distance of about 1 mm to 10 mm, or between 4 mm and 7 mm. In other embodiments modulation electrodes 158a, 158b may be spaced apart by between approximately 6 mm and 7 mm.

Electrode configurations D, E, and F show that when modulation electrodes 158a, 158b of a constant distance are changed in size, the shape of the electric field facilitated by the electrodes changes. If a constant level of current is passed between when modulation electrodes 158a and 158b, the smaller electrodes of configuration D may facilitate a deeper field than that of configurations E and F, although the effect is less significant relative to changes in distance between the electrodes. As noted above, the facilitated electric fields are not of uniform strength throughout, and thus the voltage potential at seemingly similar locations within each of the electric fields of configurations D, E, and, F may vary considerably. Appropriate sizes of modulation electrodes 158a, 158b, may therefore depend on an implant location and a nerve to be stimulated.

In some embodiments, modulation electrodes 158a, 158b may have a surface area between approximately 0.01 mm$^2$ and 80 mm$^2$. In additional embodiments, modulation electrodes 158a, 158b may have a surface area between approximately 0.1 mm$^2$ and 4 mm$^2$. In other embodiments modulation electrodes 158a, 158b may have a surface area of between approximately 0.25 mm$^2$ and 0.35 mm$^2$.

In some embodiments, modulation electrodes 158a, 158b may be arranged such that the electrodes are exposed on a single side of carrier 161. In such an embodiment, an electric field is generated only on the side of carrier 161 with exposed electrical contacts. Such a configuration may serve to reduce the amount of energy required to achieve neural modulation, because the entire electric field is generated on the same side of the carrier as the nerve, and little or no current is wasted traveling through tissue away from the nerve to be modulated. Such a configuration may also serve to make the modulation more selective. That is, by generating an electric field on the side of the carrier where there is a nerve to be modulated, nerves located in other areas of tissue (e.g. on the other side of the carrier from the nerve to be modulated), may avoid being accidentally modulated.

As discussed above, the utilization of electric fields having electrical field lines extending in a direction substantially parallel to the longitudinal direction of a nerve to be modulated may serve to lower the power requirements of modulation. This reduction in power requirements may permit the modulation of a nerve using less than 1.6 mA of current, less than 1.4 mA of current, less than 1.2 mA of current, less than 1 mA of current, less than 0.8 mA of current, less than 0.6 mA of current, less than 0.4 mA of current, and even less than 0.2 mA of current passed between modulation electrodes 158a, 158b.

Reducing the current flow required may have additional effects on the configuration of implant unit 110 and external unit 120. For example, the reduced current requirement may enable implant unit 110 to modulate a nerve without a requirement for a power storage unit, such as a battery or capacitor, to be implanted in conjunction with implant unit 110. For example, implant unit 110 may be capable of modulating a nerve using only the energy received via secondary antenna 152. Implant unit 110 may be configured to serve as a pass through that directs substantially all received energy to modulation electrodes 158a and 158b for nerve modulation. Substantially all received energy may refer to that portion of energy that is not dissipated or otherwise lost to the internal components of implant unit 110. Finally, the reduction in required current may also serve to reduce the amount of energy required by external unit 120. External unit 120 may be configured to operate successfully for an entire treatment session lasting from one to ten hours by utilizing a battery having a capacity of less than 240 mAh, less than 120 mAh, and even less than 60 mAh.

As discussed above, utilization of parallel fields may enable implant unit 110 to modulate nerves in a non-contacting fashion. Contactless neuromodulation may increase the efficacy of an implanted implant unit 110 over time compared to modulation techniques requiring contact with a nerve or muscle to be modulated. Over time, implantable devices may migrate within the body. Thus, an implantable device requiring nerve contact to initiate neural modulation may lose efficacy as the device moves within the body and loses contact with the nerve to be modulated. In contrast, implant unit 110, utilizing contactless modulation, may still effectively modulate a nerve even if it moves toward, away, or to another location relative to an initial implant location. Additionally, tissue growth and/or fibrosis may develop around an implantable device. This growth may serve to lessen or even eliminate the contact between a device designed for contact modulation and a nerve to be modulated. In contrast, implant unit 110, utilizing contactless modulation, may continue to effectively modulate a nerve if additional tissue forms between it and a nerve to be modulated.

Another feature enabled through the use of parallel fields is the ability to modulate nerves of extremely small diameter. As the diameter of a nerve decreases, the electrical resistance of the nerve increases, causing the voltage required to induce an action potential to rise. As described above, the utilization of parallel electric fields permits the application of larger voltage potentials across nerves. This, in turn, may permit the modulation of smaller diameter nerves, requiring larger voltage potentials to induce action potentials. Nerves typically have reduced diameters at their terminal fibers, e.g. the distal ends, as they extend away from the nerve trunk. Modulating these narrower terminal fibers may permit more selective modulation. Larger nerve trunks typically carry many nerve fibers that may innervate several different muscles, and so inducing modulation of a nerve trunk may cause to the modulation of unintended nerve fibers, and thus the innervation and contraction of unintended muscles. Selective modulation of terminal fibers may prevent such unintended muscle activity. In some embodiments, implant unit 110 may be configured to modulate nerves having diameters of less than 2 mm, less than 1 mm, less than 500 microns, less than 200 microns, less than 100 microns, less than 50 microns, and even less than 25 microns.

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158a and 158b).

Processor 144 may be configured to limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. Processor 144 may be configured to account for such limitations when setting the magnitude and/or duration of a primary signal to be applied to primary antenna 150.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals).

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also be configured to cause application of sub-modulation control signals to primary antenna 150. Such sub-modulation control signals may include an amplitude and/or duration that result in a sub-modulation signal at electrodes 158a, 158b. While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, induces a primary coupled signal component on primary antenna 150.

To analyze the primary coupled signal component induced on primary antenna 150, external unit 120 may include a feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary coupled signal component on primary antenna 150.

The primary coupled signal component may be fed to processor 144 by feedback circuit 148 and may be used as a basis for determining a degree of coupling between primary antenna 150 and secondary antenna 152. The degree of coupling may enable determination of the efficacy of the energy transfer between two antennas. Processor 144 may also use the determined degree of coupling in regulating delivery of power to implant unit 110.

Processor 144 may be configured with any suitable logic for determining how to regulate power transfer to implant unit 110 based on the determined degree of coupling. For example, where the primary coupled signal component indicates that a degree of coupling has changed from a baseline coupling level, processor 144 may determine that secondary antenna 152 has moved with respect to primary antenna 150 (either in coaxial offset, lateral offset, or angular offset, or any combination). Such movement, for example, may be associated with a movement of the implant unit 110, and the tissue that it is associated with based on its implant location. Thus, in such situations, processor 144 may determine that modulation of a nerve in the patient's body is appropriate. More particularly, in response to an indication of a change in coupling, processor 144, in some embodiments, may cause application of a modulation control signal to primary antenna 150 in order to generate a modulation signal at implant electrodes 158a, 158b, e.g., to cause modulation of a nerve of the patient.

In an embodiment for the treatment of a sleep breathing disorder, movement of an implant unit 110 may be associated with movement of the tongue, which may indicate snoring, the onset of a sleep apnea event or a sleep apnea precursor. Each of these conditions may require the stimulation of the genioglossus muscle of the patient to relieve or avert the event. Such stimulation may result in contraction of the muscle and movement of the patient's tongue away from the patient's airway.

In embodiments for the treatment of head pain, including migraines, processor 144 may be configured to generate a modulation control signal based on a signal from a user, for example, or a detected level of neural activity in a sensory neuron (e.g. the greater occipital nerve or trigeminal nerve) associated with head pain. A modulation control signal generated by the processor and applied to the primary antenna 150 may generate a modulation signal at implant electrodes 158a, 158b, e.g., to cause inhibition or blocking of a sensory nerve of the patient. Such inhibition or blocking may decrease or eliminate the sensation of pain for the patient.

In embodiments for the treatment of hypertension, processor 144 may be configured to generate a modulation control signal based on, for example, pre-programmed instructions and/or signals from an implant indicative of blood pressure. A modulation control signal generated by the processor and applied to the primary antenna 150 may generate a modulation signal at implant electrodes 158a, 158b, e.g., to cause either inhibition or stimulation of nerve of a patient, depending on the requirements. For example, a neuromodulator placed in a carotid artery or jugular artery (i.e. in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator place in a renal artery may receive a modulation control signal tailored to cause an inhibiting or blocking signal at the electrodes, thereby inhibiting a signal to raise blood pressure carried from the renal nerves to the kidneys.

Modulation control signals may include stimulation control signals, and sub-modulation control signals may include sub-stimulation control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

Figure 17:
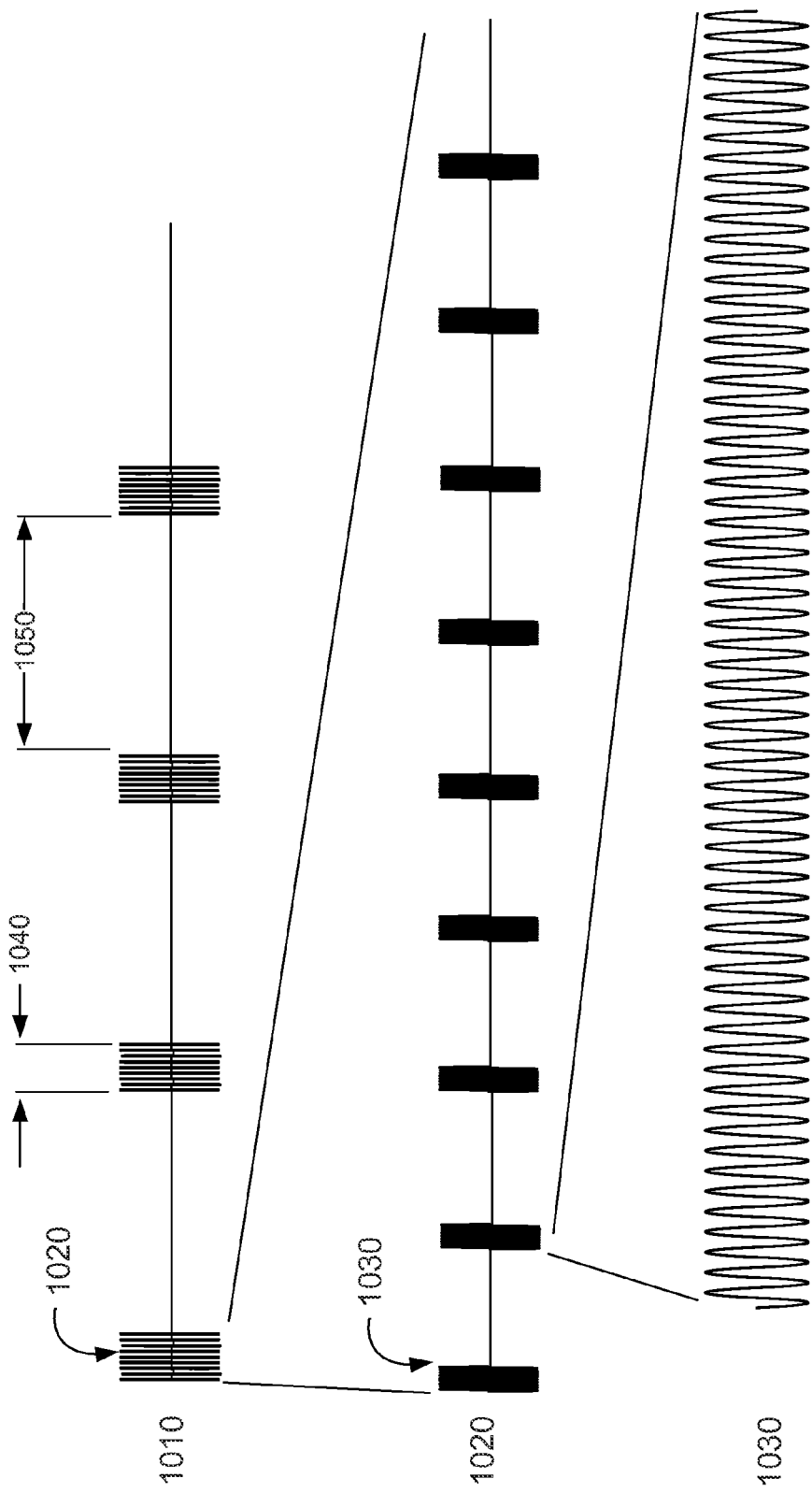
FIG. 17 depicts the composition of an exemplary modulation pulse train.

In some embodiments, stimulation control signals may include a pulse train, wherein each pulse includes a plurality of sub-pulses. FIG. 17 depicts the composition of an exemplary modulation pulse train. Such a pulse train 1010 may include a plurality of modulation pulses 1020, wherein each modulation pulse 1020 may include a plurality of modulation sub-pulses 1030. FIG. 10 is exemplary only, at a scale appropriate for illustration, and is not intended to encompass all of the various possible embodiments of a modulation pulse train, discussed in greater detail below. An alternating current signal (e.g., at a frequency of between about 6.5-13.6 MHz) may be used to generate a pulse train 1010, as follows. A sub-pulse 1030 may have a pulse duration of between 50-250 microseconds, or a pulse duration of between 1 microsecond and 2 milliseconds, during which an alternating current signal is turned on. For example, a 200 microsecond sub-pulse 1030 of a 10 MHz alternating current signal will include approximately 2000 periods. Each modulation pulse 1020 may, in turn, have a pulse duration 1040 of between 100 and 500 milliseconds, during which sub-pulses 1030 occur at a frequency of between 25 and 100 Hz. Thus, a modulation pulse 1020 may include between about 2.5 and 50 modulation sub-pulses 1030. In some embodiments, a modulation 1020 pulse may include between about 5 and 15 modulation sub-pulses 1030. For example, a 200 millisecond modulation pulse 1020 of 50 Hz modulation sub-pulses 1030 will include approximately 10 modulation sub-pulses 1030. Finally, in a modulation pulse train 1010, each modulation pulse 1020 may be separated from the next by a temporal spacing 1050 of between 0.2 and 2 seconds. For example, in a pulse train 1010 of 200 millisecond pulse duration 1040 modulation pulses 1020, each separated by a 1.3 second temporal spacing 1050 from the next, a new modulation pulse 1020 will occur every 1.5 seconds. The frequency of modulation pulses 1020 may also be timed in accordance with physiological events of the subject. For example, modulation pulses 1020 may occur at a frequency chosen from among any multiple of a breathing frequency, such as four, eight, or sixteen. In another example, modulation pulses 1020 may be temporally spaced so as not to permit a complete relaxation of a muscle after causing a muscular contraction. The pulse duration 1040 of modulation pulses 1020 and the temporal spacing 1050 between modulation pulses 1020 in a pulse train 1010 may be maintained for a majority of the modulation pulses 1020, or may be varied over the course of a treatment session according to a subject's need. Such variations may also be implemented for the modulation sub-pulse duration and temporal spacing.

Pulse train 1010 depicts a primary signal pulse train, as generated by external unit 120. In some embodiments, the primary signal may result in a secondary signal on the secondary antenna 152 of implant unit 110. This signal may be converted to a direct current signal for delivery to modulation electrodes 158a, 158b. In this situation, the generation of modulation sub-pulse 1030 may result in the generation and delivery of a square wave of a similar duration as modulation sub-pulse 1030 to modulation electrodes 158a, 158b.

In an embodiment for the treatment of sleep disordered breathing, modulation pulses 1020 and modulation sub-pulses 1030 may include stimulation pulses and stimulation sub-pulses adapted to cause neural stimulation. A pulse train 1010 of this embodiment may be utilized, for example, to provide ongoing stimulation during a treatment session. Ongoing stimulation during a treatment session may include transmission of the pulse train for at least 70%, at least 80%, at least 90%, and at least 99% of the treatment session. In the context of sleep disordered breathing, a treatment session may be a period of time during which a subject is asleep and in need of treatment to prevent sleep disordered breathing. Such a treatment session may last anywhere from about three to ten hours. A treatment session may include as few as approximately 4,000 and as many as approximately 120,000 modulation pulses 1020. In some embodiments, a pulse train 1010 may include at least 5,000, at least 10,000, and at least 100,000 modulation pulses 1020. In the context of other conditions to which neural modulators of the present disclosure are applied, a treatment session may be of varying length according to the duration of the treated condition.

Processor 144 may be configured to determine a degree of coupling between primary antenna 150 and secondary antenna 152 by monitoring one or more aspects of the primary coupled signal component received through feedback circuit 148. In some embodiments, processor 144 may determine a degree of coupling between primary antenna 150 and secondary antenna 152 by monitoring a voltage level associated with the primary coupled signal component, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary coupled signal component. This baseline voltage level, for example, may be associated with a range of movement of the patient's tongue when a sleep apnea event or its precursor is not occurring, e.g. during normal breathing. As the patient's tongue moves toward a position associated with a sleep apnea event or its precursor, the coaxial, lateral, or angular offset between primary antenna 150 and secondary antenna 152 may change. As a result, the degree of coupling between primary antenna 150 and secondary antenna 152 may change, and the voltage level or current level of the primary coupled signal component on primary antenna 150 may also change. Processor 144 may be configured to recognize a sleep apnea event or its precursor when a voltage level, current level, or other electrical characteristic associated with the primary coupled signal component changes by a predetermined amount or reaches a predetermined absolute value.

Figure 18:
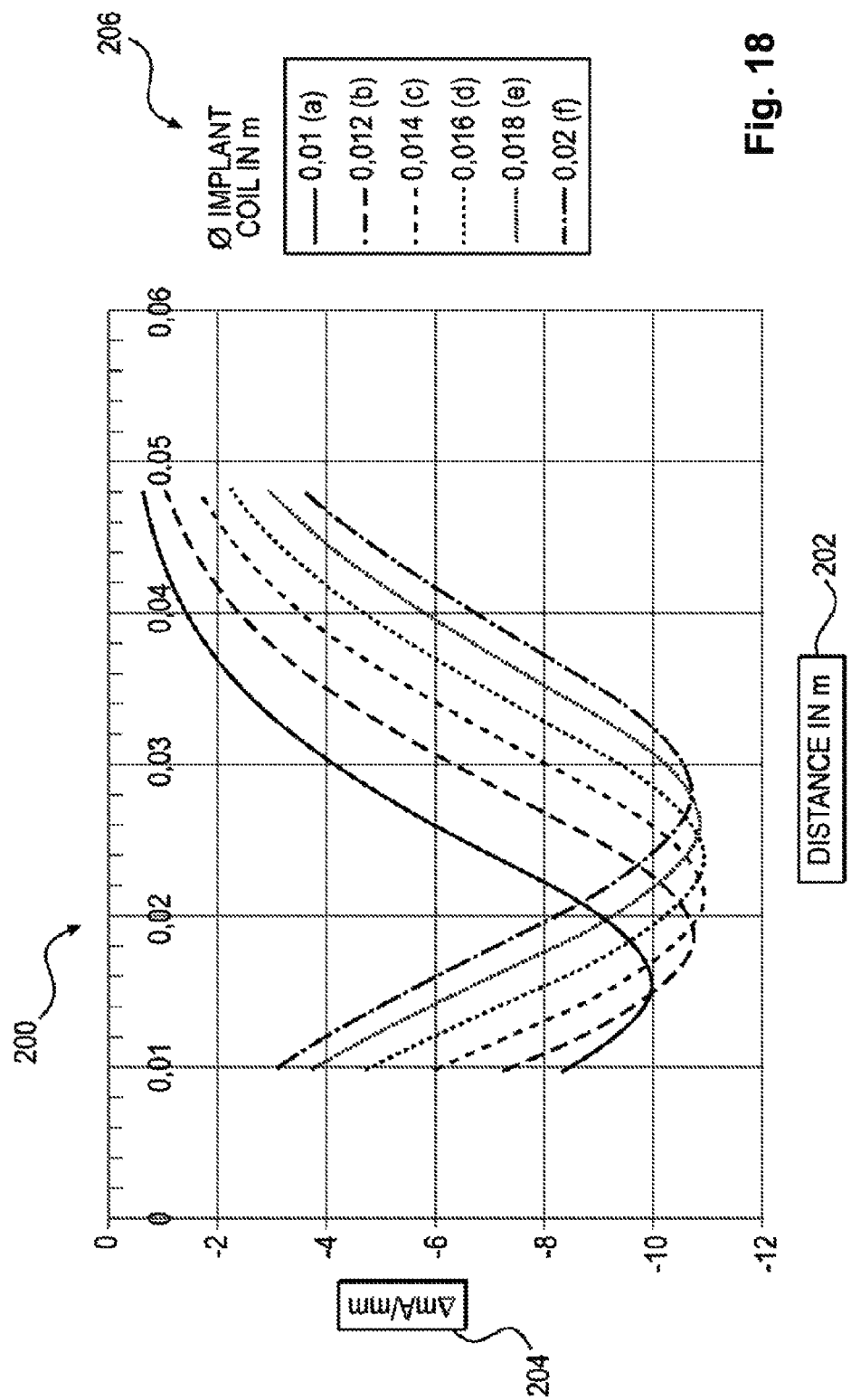
FIG. 18 illustrates a graph of quantities that may be used in determining energy delivery as a function coupling, according to an exemplary disclosed embodiment.

FIG. 18 provides a graph that illustrates this principle in more detail. For a two-coil system where one coil receives a radio frequency (RF) drive signal, graph 200 plots a rate of change in induced current in the receiving coil as a function of coaxial distance between the coils. For various coil diameters and initial displacements, graph 200 illustrates the sensitivity of the induced current to further displacement between the coils, moving them either closer together or further apart. It also indicates that, overall, the induced current in the secondary coil will decrease as the secondary coil is moved away from the primary, drive coil, i.e. the rate of change of induced current, in mA/mm, is consistently negative. The sensitivity of the induced current to further displacement between the coils varies with distance. For example, at a separation distance of 10 mm, the rate of change in current as a function of additional displacement in a 14 mm coil is approximately −6 mA/mm. If the displacement of the coils is approximately 22 mm, the rate of change in the induced current in response to additional displacement is approximately −11 mA/mm, which corresponds to a local maximum in the rate of change of the induced current. Increasing the separation distance beyond 22 mm continues to result in a decline in the induced current in the secondary coil, but the rate of change decreases. For example, at a separation distance of about 30 mm, the 14 mm coil experiences a rate of change in the induced current in response to additional displacement of about −8 mA/mm. With this type of information, processor 144 may be able to determine a particular degree of coupling between primary antenna 150 and secondary antenna 152, at any given time, by observing the magnitude and/or rate of change in the magnitude of the current associated with the primary coupled signal component on primary antenna 150.

Processor 144 may be configured to determine a degree of coupling between primary antenna 150 and secondary antenna 152 by monitoring other aspects of the primary coupled signal component. For example, in some embodiments, a residual signal, or an echo signal, may be monitored. As shown in FIG. 14, circuitry 180 in implant unit 110 may include inductors, capacitors, and resistors, and thus may constitute an LRC circuit. As described in greater detail above, when external unit 120 transmits a modulation (or sub-modulation) control signal, a corresponding signal is developed on secondary antenna 152. The signal developed on secondary antenna 152 causes current to flow in circuitry 180 of implant unit 110, exciting the LRC circuit. When excited the LRC circuit may oscillate at its resonant frequency, related to the values of the L (inductance), R (resistance), and C (capacitance values in the circuit). When processor 144 discontinues generating the control signal, both the oscillating signal on primary antenna 150 and the oscillating signal on secondary antenna 152 may decay over a period of time as the current is dissipated. As the oscillating signal on the secondary antenna 152 decays, so too does the coupled feedback signal received by primary antenna 150. Thus, the decaying signal in circuitry 180 of implant unit 110 may be monitored by processor 144 of external unit 120. This monitoring may be further facilitated by configuring the circuitry 170 of external unit 120 to allow the control signal generated in primary antenna 150 to dissipate faster than the signal in the implant unit 110. Monitoring the residual signal and comparing it to expect values of a residual signal may provide processor 144 with an indication of a degree of coupling between primary antenna 150 and secondary antenna 152.

Monitoring the decaying oscillating signal in the implant unit 110 may also provide processor 144 information about the performance of implant unit 110. Processor 144 may be configured to compare the parameters of the control signal with the parameters of the detected decaying implant signal. For example, an amplitude of the decaying signal is proportional to the amount of energy remaining in implant unit 110; by comparing an amount of energy transmitted in the control signal with an amount of energy remaining in the implant, processor 144 may determine a level of power consumption in the implant. Further, by comparing a level of power consumption in the implant to a detected amount of tongue movement, processor 144 may determine an efficacy level of transmitted modulation signals. Monitoring the residual, or echo signals, in implant unit 110 may permit the implementation of several different features. Thus, processor 144 may be able to determine information including power consumption in implant unit 110, current delivery to the tissue by implant unit 110, energy delivery to implant unit 110, functionality of implant unit 110, and other parameters determinable through residual signal analysis Processor 144 may be configured to monitor the residual implant signal in a diagnostic mode. For example, if processor 144 detects no residual signal in implant unit 110 after transmission of a control signal, it may determine that implant unit 110 is unable to receive any type of transmission, and is not functioning. In such a case, processor 144 may cause a response that includes an indication to a user that implant unit 110 is not functioning properly. Such an indication may be in the form of, e.g., an audible or visual alarm. In another potential malfunction, if processor 144 detects a residual signal in the implant that is higher than expected, it may determine that, while implant unit is receiving a transmitted control signal, the transmitted energy is not being transferred to the tissue by electrodes 158a, 158b, at an appropriate rate.

Processor 144 may also be configured to implement a treatment protocol including the application of a desired target current level to be applied by the modulation electrodes (e.g., 1 mA). Even if the modulation control signal delivers a signal of constant amplitude, the delivered current may not remain stable. The coupled feedback signal detected by primary antenna 150 may be used as the basis for feedback control of the implant unit to ensure that the implant delivers a stable 1 mA current during each application of a modulation control signal. Processor 144, by analyzing the residual signal in the implant, may determine an amount of current delivered during the application of a modulation control signal. Processor 144 may then increase or decrease the amplitude of the modulation control signal based on the determined information about the delivered current. Thus, the modulation control signal applied to primary antenna 150 may be adjusted until the observed amplitude of the echo signal indicates that the target current level has been achieved.

In some embodiments, processor 144 may be configured to alter a treatment protocol based on detected efficacy during a therapy period. As described above, processor 144 may be configured, through residual signal analysis, to determine the amount of current, power, or energy delivered to the tissue through electrodes 158*a*, 158*b*. Processor 144 may be configured to correlate the detected amount of tongue movement as a result of a modulation control signal with the amount of power ultimately delivered to the tissue. Thus, rather than comparing the effects of signal transmission with the amount of power or energy transmitted (which processor 144 may also be configured to do), processor 144 may compare the effects of signal transmission with the amount of power delivered. By comparing modulating effects with power delivered, processor 144 may be able to more accurately optimize a modulation signal.

The residual signal feedback methods discussed above may be applied to any of several other embodiments of the disclosure as appropriate. For example, information gathered through residual signal feedback analysis may be included in the information stored in memory unit 143 and transmitted to a relay or final destination via communications interface 145 of external unit 120. In another example, the above described residual signal feedback analysis may be incorporated into methods detecting tongue movement and tongue vibration.

In some embodiments, an initially detected coupling degree may establish a baseline range when the patient attaches external unit 120 to the skin. Presumably, while the patient is awake, the tongue is not blocking the patient's airway and moves with the patients breathing in a natural range, where coupling between primary antenna 150 and secondary antenna 152 may be within a baseline range. A baseline coupling range may encompass a maximum coupling between primary antenna 150 and secondary antenna 152. A baseline coupling range may also encompass a range that does not include a maximum coupling level between primary antenna 150 and secondary antenna 152. Thus, the initially determined coupling may be fairly representative of a non-sleep apnea condition and may be used by processor 144 as a baseline in determining a degree of coupling between primary antenna 150 and secondary antenna 152.

As the patient wears external unit 120, processor 144 may periodically scan over a range of primary signal amplitudes to determine current values of coupling. If a periodic scan results in determination of a degree of coupling different from the baseline coupling, processor 144 may determine that there has been a change from the baseline initial conditions.

By periodically determining a degree of coupling value, processor 144 may be configured to determine, in situ, appropriate parameter values for the modulation control signal that will ultimately result in nerve modulation. For example, by determining the degree of coupling between primary antenna 150 and secondary antenna 152, processor 144 may be configured to select characteristics of the modulation control signal (e.g., amplitude, pulse duration, frequency, etc.) that may provide a modulation signal at electrodes 158*a*, 158*b* in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

Additionally or alternatively, processor 144 may be configured to determine the degree of coupling between primary antenna 150 and secondary antenna 152 during modulation. The tongue, or other structure on or near which the implant is located, and thus implant unit 110, may move as a result of modulation. Thus, the degree of coupling may change during modulation. Processor 144 may be configured to determine the degree of coupling as it changes during modulation, in order to dynamically adjust characteristics of the modulation control signal according to the changing degree of coupling. This adjustment may permit processor 144 to cause implant unit 110 to provide an appropriate modulation signal at electrodes 158*a*, 158*b* throughout a modulation event. For example, processor 144 may alter the primary signal in accordance with the changing degree of coupling in order to maintain a constant modulation signal, or to cause the modulation signal to be reduced in a controlled manner according to patient needs.

More particularly, the response of processor 144 may be correlated to the determined degree of coupling. In situations where processor 144 determines that the degree of coupling between primary antenna 150 and secondary antenna has fallen only slightly below a predetermined coupling threshold (e.g., during snoring or during a small vibration of the tongue or other sleep apnea event precursor), processor 144 may determine that only a small response is necessary. Thus, processor 144 may select modulation control signal parameters that will result in a relatively small response (e.g., a short stimulation of a nerve, small muscle contraction, etc.). Where, however, processor 144 determines that the degree of coupling has fallen substantially below the predetermined coupling threshold (e.g., where the tongue has moved enough to cause a sleep apnea event), processor 144 may determine that a larger response is required. As a result, processor 144 may select modulation control signal parameters that will result in a larger response. In some embodiments, only enough power may be transmitted to implant unit 110 to cause the desired level of response. In other words, processor 144 may be configured to cause a metered response based on the determined degree of coupling between primary antenna 150 and secondary antenna 152. As the determined degree of coupling decreases, processor 144 may cause transfer of power in increasing amounts. Such an approach may preserve battery life in the external unit 120, may protect circuitry 170 and circuitry 180, may increase effectiveness in addressing the type of detected condition (e.g., sleep apnea, snoring, tongue movement, etc.), and may be more comfortable for the patient.

In some embodiments, processor 144 may employ an iterative process in order to select modulation control signal parameters that result in a desired response level. For example, upon determining that a modulation control signal should be generated, processor 144 may cause generation of an initial modulation control signal based on a set of predetermined parameter values. If feedback from feedback circuit 148 indicates that a nerve has been modulated (e.g., if an increase in a degree of coupling is observed), then processor 144 may return to a monitoring mode by issuing sub-modulation control signals. If, on the other hand, the feedback suggests that the intended nerve modulation did not occur as a result of the intended modulation control signal or that modulation of the nerve occurred but only partially provided the desired result (e.g., movement of the tongue only partially away from the airway), processor 144 may change one or more parameter values associated with the modulation control signal (e.g., the amplitude, pulse duration, etc.).

Where no nerve modulation occurred, processor 144 may increase one or more parameters of the modulation control signal periodically until the feedback indicates that nerve modulation has occurred. Where nerve modulation occurred, but did not produce the desired result, processor 144 may re-evaluate the degree of coupling between primary antenna 150 and secondary antenna 152 and select new parameters for the modulation control signal targeted toward achieving a desired result. For example, where stimulation of a nerve causes the tongue to move only partially away from the patient's airway, additional stimulation may be desired. Because the tongue has moved away from the airway, however, implant unit 110 may be closer to external unit 120 and, therefore, the degree of coupling may have increased. As a result, to move the tongue a remaining distance to a desired location may require transfer to implant unit 110 of a smaller amount of power than what was supplied prior to the last stimulation-induced movement of the tongue. Thus, based on a newly determined degree of coupling, processor 144 can select new parameters for the stimulation control signal aimed at moving the tongue the remaining distance to the desired location.

In one mode of operation, processor 144 may be configured to sweep over a range of parameter values until nerve modulation is achieved. For example, in circumstances where an applied sub-modulation control signal results in feedback indicating that nerve modulation is appropriate, processor 144 may use the last applied sub-modulation control signal as a starting point for generation of the modulation control signal. The amplitude and/or pulse duration (or other parameters) associated with the signal applied to primary antenna 150 may be iteratively increased by predetermined amounts and at a predetermined rate until the feedback indicates that nerve modulation has occurred.

Processor 144 may be configured to determine or derive various physiologic data based on the determined degree of coupling between primary antenna 150 and secondary antenna 152. For example, in some embodiments the degree of coupling may indicate a distance between external unit 120 and implant unit 110, which processor 144 may use to determine a position of external unit 120 or a relative position of a patient's tongue. Monitoring the degree of coupling can also provide such physiologic data as whether a patient's tongue is moving or vibrating (e.g., whether the patient is snoring), by how much the tongue is moving or vibrating, the direction of motion of the tongue, the rate of motion of the tongue, etc.

In response to any of these determined physiologic data, processor 144 may regulate delivery of power to implant unit 110 based on the determined physiologic data. For example, processor 144 may select parameters for a particular modulation control signal or series of modulation control signals for addressing a specific condition relating to the determined physiologic data. If the physiologic data indicates that the tongue is vibrating, for example, processor 144 may determine that a sleep apnea event is likely to occur and may issue a response by delivering power to implant unit 110 in an amount selected to address the particular situation. If the tongue is in a position blocking the patient's airway (or partially blocking a patient's airway), but the physiologic data indicates that the tongue is moving away from the airway, processor 144 may opt to not deliver power and wait to determine if the tongue clears on its own. Alternatively, processor 144 may deliver a small amount of power to implant unit 110 (e.g., especially where a determined rate of movement indicates that the tongue is moving slowly away from the patient's airway) to encourage the tongue to continue moving away from the patient's airway or to speed its progression away from the airway.

In an embodiment for the treatment of snoring, processor 144 may be configured to determine when a subject is snoring based on a feedback signal that varies based on a breathing pattern of the subject. The feedback signal, may include, for example, the signal induced in the primary antenna as a result of a sub-modulating signal transmitted to the secondary antenna. In an embodiment for determining whether a subject is snoring, in addition to a tongue location, tongue movement may be detected through a degree of coupling. Tongue movement, which may include tongue velocity, tongue displacement, and tongue vibration, may be indicative of snoring. Processor 144 may be configured to detect a tongue movement pattern and compare the detected movement pattern to known patterns indicative of snoring. For example, when a patient snores, the tongue may vibrate in a range between 60-100 Hz, such vibration may be detected by monitoring the coupling signal for a signal at a similar frequency. Such changes in the coupling signal may be relatively small compared to changes associated with larger movements of the tongue. Thus, snoring detection methods may be optimized to identify low amplitude signals. A low amplitude signal between 60-100 Hz may thus constitute a tongue movement pattern indicative of snoring. Additional patterns may also be detected.

Another exemplary feedback signal may include a signal obtained by external unit 120 about a snoring condition. For example, audio sensors, microphones, and/or piezoelectric devices may be incorporated into external unit 120 to gather data about a potential snoring condition. Such sensors may detect sound vibrations traveling through the air and may detect vibrations of the subject's body near the location of the external unit's contact with the skin. In still another embodiment, the feedback signal may be provided by a thermistor, or other temperature measuring device, positioned so as to measure a temperature in the airway.

In yet another embodiment, a feedback signal that varies based upon a breathing pattern of the subject may be provided by electromyography electrodes. Electromyography electrodes may detect electrical activity in muscles. Interpretation of this electrical activity may provide information about muscular contraction and muscle tone. During normal breathing, subjects typically exhibit a pattern of muscular contractions that may be associated with the normal breathing, as muscles from the face, chin, neck, ribs, and diaphragm experience contractions in sequence. Electromyography electrodes may be used to measure both the strength and the pattern of muscular contractions during breathing.

In still another embodiment, an accelerometer located on, or otherwise associated with external unit 120 may be utilized as the feedback signal to detect snoring. Located on the neck, ribs, or diaphragm, an accelerometer, by measuring external body movements, may detect a subject's breathing patterns. The accelerometer-detected breathing patterns may be analyzed to detect deviations from a normal breathing pattern, such as breathing patterns indicating heightened or otherwise altered effort.

In additional embodiments, multiple feedback signals may be utilized to detect snoring in various combinations. For example, processor 144 may be configured such that, when a tongue movement pattern indicative of snoring is detected, sensors incorporated into external unit 120 are then monitored for confirmation that a snoring condition is occurring. In another example, processor 144 may be configured to utilize sensors in external unit 120 and/or an airway temperature measuring device to detect the presence of snoring, and then to detect and record the tongue movement pattern associated with the snoring. In this way, processor 144 may be configured to learn a tongue movement pattern associated with snoring individual to a particular user.

Snoring may be correlated with heightened or otherwise altered breathing effort. Any or all of the previously described feedback methods may be used to determine or detect a heightened or otherwise altered breathing effort. Detection of such heightened or otherwise altered breathing effort may be used by processor 144 to determine that snoring is occurring.

If snoring is detected, processor 144 may be configured to cause a hypoglossal nerve modulation control signal to be applied to the primary antenna in order to wirelessly transmit the hypoglossal nerve modulation control signal to the secondary antenna of implant unit 110. Thus, in response to a detection of snoring, the processor may cause the hypoglossal nerve to be modulated. Hypoglossal nerve modulation may cause a muscular contraction of the genioglossus muscle, which may in turn alleviate the snoring condition.

The scenarios described are exemplary only. Processor 144 may be configured with software and/or logic enabling it to address a variety of different physiologic scenarios with particularity. In each case, processor 144 may be configured to use the physiologic data to determine an amount of power to be delivered to implant unit 110 in order to modulate nerves associated with the tongue with the appropriate amount of energy.

The disclosed embodiments may be used in conjunction with a method for regulating delivery of power to an implant unit. The method may include determining a degree of coupling between primary antenna 150 associated with external unit 120 and secondary antenna 152 associated with implant unit 110, implanted in the body of a patient. Determining the degree of coupling may be accomplished by processor 144 located external to implant unit 110 and that may be associated with external unit 120. Processor 144 may be configured to regulate delivery of power from the external unit to the implant unit based on the determined degree of coupling.

As previously discussed, the degree of coupling determination may enable the processor to further determine a location of the implant unit. The motion of the implant unit may correspond to motion of the body part where the implant unit may be attached. This may be considered physiologic data received by the processor. The processor may, accordingly, be configured to regulate delivery of power from the power source to the implant unit based on the physiologic data. In alternative embodiments, the degree of coupling determination may enable the processor to determine information pertaining to a condition of the implant unit. Such a condition may include location as well as information pertaining to an internal state of the implant unit. The processor may, according to the condition of the implant unit, be configured to regulate delivery of power from the power source to the implant unit based on the condition data.

In some embodiments, implant unit 110 may include a processor located on the implant. A processor located on implant unit 110 may perform all or some of the processes described with respect to the at least one processor associated with an external unit. For example, a processor associated with implant unit 110 may be configured to receive a control signal prompting the implant controller to turn on and cause a modulation signal to be applied to the implant electrodes for modulating a nerve. Such a processor may also be configured to monitor various sensors associated with the implant unit and to transmit this information back to and external unit. Power for the processor unit may be supplied by an onboard power source or received via transmissions from an external unit.

In other embodiments, implant unit 110 may be self-sufficient, including its own power source and a processor configured to operate the implant unit 110 with no external interaction. For example, with a suitable power source, the processor of implant unit 110 could be configured to monitor conditions in the body of a subject (via one or more sensors or other means), determining when those conditions warrant modulation of a nerve, and generate a signal to the electrodes to modulate a nerve. The power source could be regenerative based on movement or biological function; or the power sources could be periodically rechargeable from an external location, such as, for example, through induction.

Figure 19:
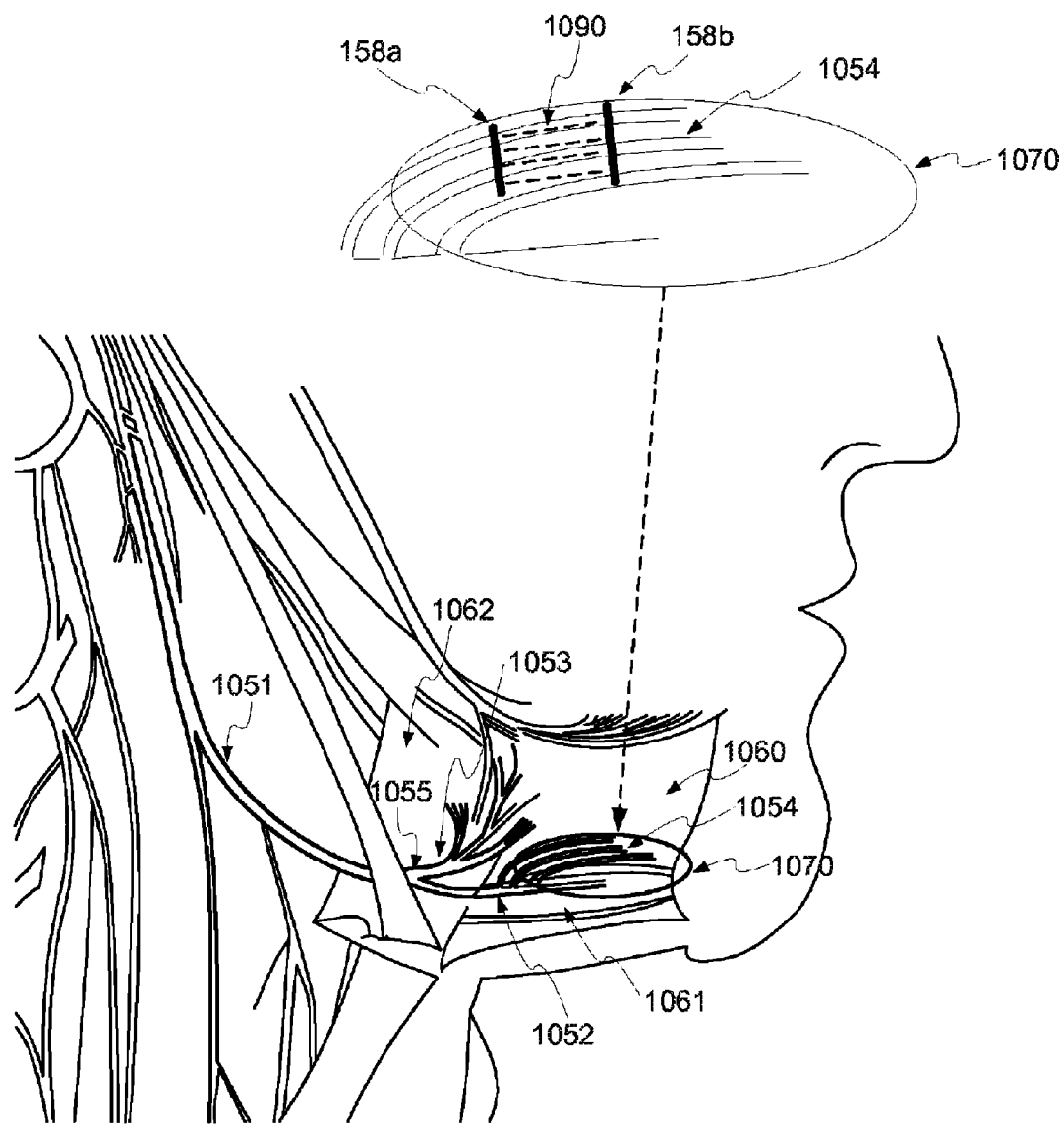
FIG. 19 depicts anatomy of the tongue and associated muscles and nerves.

FIG. 19 illustrates an exemplary implantation location for implant unit 110. FIG. 19 depicts an implantation location in the vicinity of a genioglossus muscle 1060 that may be accessed through derma on an underside of a subject's chin. FIG. 19 depicts hypoglossal nerve (i.e. cranial nerve XII). The hypoglossal nerve 1051, through its lateral branch 1053 and medial branch 1052, innervates the muscles of the tongue and other glossal muscles, including the genioglossus 1060, the hyoglossus, 1062, myelohyoid (not shown) and the geniohyoid 1061 muscles. The myelohyoid muscle, not pictured in FIG. 19, forms the floor of the oral cavity, and wraps around the sides of the genioglossus muscle 1060. The horizontal compartment of the genioglossus 1060 is mainly innervated by the medial terminal fibers 1054 of the medial branch 1052, which diverges from the lateral branch 1053 at terminal bifurcation 1055. The distal portion of medial branch 1052 then variegates into the medial terminal fibers 1054. Contraction of the horizontal compartment of the genioglossus muscle 1060 may serve to open or maintain a subject's airway. Contraction of other glossal muscles may assist in other functions, such as swallowing, articulation, and opening or closing the airway. Because the hypoglossal nerve 1051 innervates several glossal muscles, it may be advantageous, for OSA treatment, to confine modulation of the hypoglossal nerve 1051 to the medial branch 1052 or even the medial terminal fibers 1054 of the hypoglossal nerve 1051. In this way, the genioglossus muscle, most responsible for tongue movement and airway maintenance, may be selectively targeted for contraction inducing neuromodulation. Alternatively, the horizontal compartment of the genioglossus muscle may be selectively targeted. The medial terminal fibers 1054 may, however, be difficult to affect with neuromodulation, as they are located within the fibers of the genioglossus muscle 1061. Embodiments of the present invention facilitate modulation the medial terminal fibers 1054, as discussed further below.

In some embodiments, implant unit 110, including at least one pair of modulation electrodes, e.g. electrodes 158*a*, 158*b*, and at least one circuit may be configured for implantation through derma (i.e. skin) on an underside of a subject's chin. When implanted through derma on an underside of a subject's chin, an implant unit 110 may be located proximate to medial terminal fibers 1054 of the medial branch 1052 of a subject's hypoglossal nerve 1051. An exemplary implant location 1070 is depicted in FIG. 19.

In some embodiments, implant unit 110 may be configured such that the electrodes 158*a*, 158*b* cause modulation of at least a portion of the subject's hypoglossal nerve through application of an electric field to a section of the hypoglossal nerve 1051 distal of a terminal bifurcation 1055 to lateral and medial branches 1053, 1052 of the hypoglossal nerve 1051. In additional or alternative embodiments, implant unit 110 may be located such that an electric field extending from the modulation electrodes 158*a*, 158*b* can modulate one or more of the medial terminal fibers 1054 of the medial branch 1052 of the hypoglossal nerve 1051. Thus, the medial branch 1053 or the medial terminal fibers 1054 may be modulated so as to cause a contraction of the genioglossus muscle 1060, which may be sufficient to either open or maintain a patient's airway. When implant unit 110 is located proximate to the medial terminal fibers 1054, the electric field may be configured so as to cause substantially no modulation of the lateral branch of the subject's hypoglossal nerve 1051. This may have the advantage of providing selective modulation targeting of the genioglossus muscle 1060.

As noted above, it may be difficult to modulate the medial terminal fibers 1054 of the hypoglossal nerve 1051 because of their location within the genioglossus muscle 1060. Implant unit 110 may be configured for location on a surface of the genioglossus muscle 1060. Electrodes 158a, 158b, of implant unit 110 may be configured to generate a parallel electric field 1090, sufficient to cause modulation of the medial terminal branches 1054 even when electrodes 158a, 158b are not in contact with the fibers of the nerve. That is, the anodes and the cathodes of the implant may be configured such that, when energized via a circuit associated with the implant 110 and electrodes 158a, 158b, the electric field 1090 extending between electrodes 158a, 158b may be in the form of a series of substantially parallel arcs extending through and into the muscle tissue on which the implant is located. A pair of parallel line electrodes or two series of circular electrodes may be suitable configurations for producing the appropriate parallel electric field lines. Thus, when suitably implanted, the electrodes of implant unit 110 may modulate a nerve in a contactless fashion, through the generation of parallel electric field lines.

Furthermore, the efficacy of modulation may be increased by an electrode configuration suitable for generating parallel electric field lines that run partially or substantially parallel to nerve fibers to be modulated. In some embodiments, the current induced by parallel electric field lines may have a greater modulation effect on a nerve fiber if the electric field lines 1090 and the nerve fibers to be modulated are partially or substantially parallel. The inset illustration of FIG. 19 depicts electrodes 158a and 158b generating electric field lines 1090 (shown as dashed lines) substantially parallel to medial terminal fibers 1054.

Figure 20:
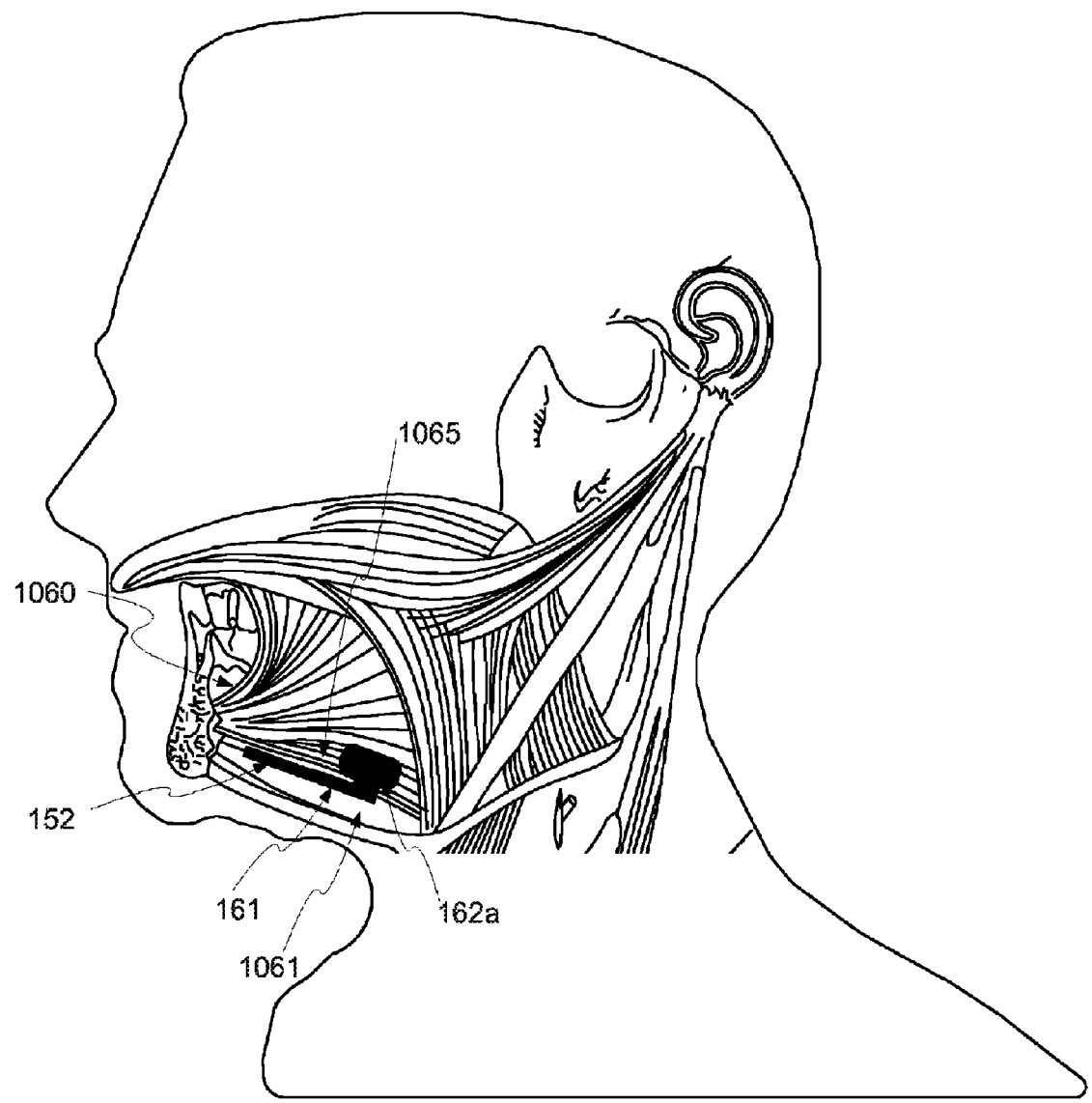
FIG. 20 illustrates an exemplary implantation position for an implant unit.

In order to facilitate the modulation of the medial terminal fibers 1054, implant unit 110 may be designed or configured to ensure the appropriate location of electrodes when implanted. An exemplary implantation is depicted in FIG. 20.

For example, a flexible carrier 161 of the implant may be configured such that at least a portion of a flexible carrier 161 of the implant is located at a position between the genioglossus muscle 1060 and the geniohyoid muscle 1061. Flexible carrier 161 may be further configured to permit at least one pair of electrodes arranged on flexible carrier 161 to lie between the genioglossus muscle 1060 and the myelohyoid muscle. Either or both of the extensions 162a and 162b of elongate arm 161 may be configured adapt to a contour of the genioglossus muscle. Either or both of the extensions 162a and 162b of elongate arm 161 may be configured to extend away from the underside of the subject's chin along a contour of the genioglossus muscle 1060. Either or both of extension arms 162a, 162b may be configured to wrap around the genioglossus muscle when an antenna 152 is located between the genioglossus 1060 and geniohyoid muscle 1061. In such a configuration, antenna 152 may be located in a plane substantially parallel with a plane defined by the underside of a subject's chin, as shown in FIG. 20.

Flexible carrier 161 may be configured such that the at least one pair of spaced-apart electrodes can be located in a space between the subject's genioglossus muscle and an adjacent muscle. Flexible carrier 161 may be configured such that at least one pair of modulation electrodes 158a, 158b is configured for implantation adjacent to a horizontal compartment 1065 of the genioglossus muscle 1060. The horizontal compartment 1065 of the genioglossus 1060 is depicted in FIG. 20 and is the portion of the muscle in which the muscle fibers run in a substantially horizontal, rather than vertical, oblique, or transverse direction. At this location, the hypoglossal nerve fibers run between and in parallel to the genioglossus muscle fibers. In such a location, implant unit 110 may be configured such that the modulation electrodes generate an electric field substantially parallel to the direction of the muscle fibers, and thus, the medial terminal fibers 1054 of the hypoglossal nerve in the horizontal compartment.

As described above, implant unit 110 may include electrodes 158a, 158b on both extensions 162a, 162b, of extension arm 162. In such a configuration, implant unit 110 may be configured for bilateral hypoglossal nerve stimulation. The above discussion has focused on a single hypoglossal nerve 1051. The body contains a pair of hypoglossal nerves 1051, on the left and right sides, each innervating muscles on its side. When a single hypoglossal nerve 1051 is modulated, it may cause stronger muscular contractions on the side of the body with which the modulated hypoglossal nerve is associated. This may result in asymmetrical movement of the tongue. When configured for bilateral stimulation, implant unit 110 may be able to stimulate both a left and a right hypoglossal nerve 1051, causing more symmetric movement of the tongue and more symmetric airway dilation. As illustrated in FIGS. 11a and 11b, flexible carrier 161 may be sized and shaped for implantation in a vicinity of a hypoglossal nerve to be modulated such that the first pair of modulation electrodes is located to modulate a first hypoglossal nerve on a first side of the subject and the second pair of modulation electrodes is located to modulate a second hypoglossal nerve on a second side of the subject.

Bilateral stimulation protocols may include various sequences of modulation. For example, both pairs of modulation electrodes may be activated together to provide a stronger muscular response in the subject. In another example, the modulation electrodes may be activated in an alternating sequence, first one, and then the other. Such a sequence may reduce muscle or neuronal fatigue during a therapy period, and may reduce the diminishment of sensitivity that can occur in a neuron subject to a constant modulation signal. In still another example, the modulation electrodes may be activated in an alternating sequence that includes polarity reversals of the electric field. In such an embodiment, one pair of electrodes may be activated with a neuromuscular modulating electric field having a polarity configured to cause a muscular contraction, while the other pair of electrodes may be activated with a field having a reversed polarity. By alternating the polarity, it may be possible to reduce short term neuronal fatigue and possible to minimize or eliminate long term neuronal damage. In some configurations, extensions 162a and 162b may act as elongated arms extending from a central portion of flexible carrier 161 of implant unit 110. The elongated arms may be configured to form an open ended curvature around a muscle, with a nerve to be stimulated, e.g. a hypoglossal nerve, located within the curvature formed by the elongated arms. Such a configuration may also include a stiffening portion located on or within flexible carrier 161. Such a stiffening portion may comprise a material that is stiffer than a material of flexible carrier 161. The stiffening portion may be preformed in a shape to better accommodate conforming flexible carrier 161 to a muscle of the subject—such as a genioglossus muscle. The stiffening portion may also be capable of plastic deformation, so as to permit a surgeon to modify the curvature of the flexible carrier 161 prior to implantation.

The diameter of the curvature of the elongated arms may be significantly larger than the diameter of the nerve to be stimulated, for example, 2, 5, 10, 20, or more times larger. In some embodiments, a plurality of nerves to be stimulated, for example a left hypoglossal nerve and a right hypoglossal nerve, may be located within the arc of curvature formed by the elongated arms.

Other embodiments of the present disclosure will be apparent to those skilled in the art from consideration of the specification and practice of the present disclosure.

While this disclosure provides examples of the neuromodulation devices employed for the treatment of certain conditions, usage of the disclosed neuromodulation devices is not limited to the disclosed examples. The disclosure of uses of embodiments of the invention for neuromodulation are to be considered exemplary only. In its broadest sense, the invention may be used in connection with the treatment of any physiological condition through neuromodulation. Alternative embodiments will become apparent to those skilled in the art to which the present invention pertains without departing from its spirit and scope. Accordingly, the scope of the present invention is defined by the appended claims rather than the foregoing description.

What is claimed is:

1. A device, comprising:
    a flexible substrate configured for removable attachment to a subject's skin;
    a primary antenna disposed on the flexible substrate;
    an interface configured to receive a feedback signal that varies based upon a breathing pattern of the subject; and
    at least one processing device configured to:
    analyze the feedback signal and determine whether the subject is snoring based on the analysis of the feedback signal; and
    if snoring is detected, cause a hypoglossal nerve modulation control signal to be applied to the primary antenna in order to wirelessly transmit the hypoglossal nerve modulation control signal to a secondary antenna associated with an implant unit configured for location in a body of the subject.

2. The device of claim 1, wherein the interface is configured to receive from the primary antenna a feedback signal that varies based upon a degree of coupling with the secondary antenna.

3. The device of claim 2, wherein the degree of coupling is indicative of tongue movement, tongue movement including at least one of tongue velocity, tongue displacement, and tongue vibration.

4. The device of claim 1, wherein the processing device is configured to compare the feedback signal to a predetermined snoring signal to detect snoring.

5. The device of claim 1, further comprising a snoring sensor configured to provide the feedback signal.

6. The device of claim 5, wherein the snoring sensor includes at least one of an audio sensor, a piezoelectric sensor, a thermistor, electromyography electrodes, and an accelerometer.

7. The device of claim 2, wherein the processing device is further configured to detect a tongue movement pattern based on the degree of coupling and to compare the detected tongue movement pattern to a predetermined tongue movement pattern in order to make a snoring determination.

8. The device of claim 7, wherein the predetermined tongue movement pattern is specific to a particular user.

9. The device of claim 1, wherein the detection of snoring is determined by a level of breathing effort.

10. A device, comprising:
    a flexible substrate configured for removable attachment to a subject's skin;
    a primary antenna disposed on the flexible substrate;
    an interface configured to receive a feedback signal that varies based on movements of the subjects tongue associated with a breathing pattern of the subject causing changes in a degree of coupling between an implanted secondary antenna and the primary antenna; and
    at least one processing device configured to:
    analyze the feedback signal and determine whether the subject is snoring based on the analysis of the feedback signal; and
    if snoring is detected, cause a hypoglossal nerve modulation control signal to be applied to the primary antenna in order to wirelessly transmit the hypoglossal nerve modulation control signal to the secondary antenna associated with an implant unit configured for location in a body of the subject.

* * * * *